United States Patent
Bedworth et al.

(10) Patent No.: US 10,653,824 B2
(45) Date of Patent: May 19, 2020

(54) TWO-DIMENSIONAL MATERIALS AND USES THEREOF

(71) Applicant: Lockheed Martin Corporation, Bethesda, MD (US)

(72) Inventors: Peter V. Bedworth, Los Gatos, CA (US); Steven Edward Bullock, Canton, GA (US); Sarah M. Simon, Baltimore, MD (US); Steven W. Sinton, Palo Alto, CA (US); John B. Stetson, Jr., New Hope, PA (US); Jacob L. Swett, Redwood City, CA (US); Scott E. Heise, San Jose, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 293 days.

(21) Appl. No.: 15/099,588

(22) Filed: Apr. 14, 2016

(65) Prior Publication Data

US 2016/0339160 A1 Nov. 24, 2016

Related U.S. Application Data

(63) Continuation-in-part of application No. 14/610,770, filed on Jan. 30, 2015, now Pat. No. 9,870,895, which
(Continued)

(51) Int. Cl.
*A61M 1/16* (2006.01)
*H01J 37/305* (2006.01)
(Continued)

(52) U.S. Cl.
CPC ........ *A61M 1/1623* (2014.02); *A61M 1/1621* (2014.02); *A61M 1/1631* (2014.02);
(Continued)

(58) Field of Classification Search
None
See application file for complete search history.

(56) References Cited

U.S. PATENT DOCUMENTS

| | | | |
|---|---|---|---|
| 2,187,417 A | 1/1940 | Doble | |
| 3,024,153 A | 3/1962 | Kennedy | |

(Continued)

FOREIGN PATENT DOCUMENTS

| | | |
|---|---|---|
| CA | 2037988 | 9/1992 |
| CA | 2411935 | 12/2002 |

(Continued)

OTHER PUBLICATIONS

AE Search and Examination Report for United Arab Emirates Application No. P186/13 dated Oct. 4, 2016.

(Continued)

*Primary Examiner* — Ana M Fortuna
(74) *Attorney, Agent, or Firm* — Foley & Lardner LLP

(57) ABSTRACT

Various systems and methods relating to two-dimensional materials such as graphene. A membrane include a cross-linked graphene platelet polymer that includes a plurality of cross-linked graphene platelets. The cross-linked graphene platelets include a graphene portion and a cross-linking portion. The cross-linking portion contains a 4 to 10 atom link. The cross-linked graphene platelet polymer is produced by reaction of an epoxide functionalized graphene platelet and a (meth)acrylate or (meth)acrylamide functionalized cross-linker.

15 Claims, 28 Drawing Sheets

Related U.S. Application Data is a continuation-in-part of application No. 14/609,325, filed on Jan. 29, 2015, now Pat. No. 10,500,546, application No. 15/099,588, which is a continuation-in-part of application No. 14/656,580, filed on Mar. 12, 2015, now Pat. No. 9,844,757, application No. 15/099,588, which is a continuation-in-part of application No. 14/656,190, filed on Mar. 12, 2015, now abandoned, application No. 15/099,588, which is a continuation-in-part of application No. 14/656,657, filed on Mar. 12, 2015, application No. 15/099,588, which is a continuation-in-part of application No. PCT/US2015/028948, filed on May 1, 2015, and a continuation of application No. PCT/US2015/018114, filed on Feb. 27, 2015, which is a continuation of application No. 14/193,007, filed on Feb. 28, 2014, now Pat. No. 9,834,809, application No. 15/099,588, which is a continuation-in-part of application No. 14/707,808, filed on May 8, 2015, now abandoned, application No. 15/099,588, which is a continuation-in-part of application No. 14/754,531, filed on Jun. 29, 2015, now abandoned, which is a continuation-in-part of application No. 13/480,569, filed on May 25, 2012, now Pat. No. 9,067,811, application No. 15/099,588, which is a continuation-in-part of application No. 14/819,273, filed on Aug. 5, 2015, now Pat. No. 9,744,617, which is a continuation-in-part of application No. 14/610,770, application No. 15/099,588, which is a continuation-in-part of application No. 14/843,944, filed on Sep. 2, 2015, now Pat. No. 10,005,038, application No. 15/099,588, which is a continuation-in-part of application No. 14/856,471, filed on Sep. 16, 2015, now abandoned, which is a continuation-in-part of application No. 14/656,190, which is a continuation-in-part of application No. 14/856,198, filed on Sep. 16, 2015, now Pat. No. 9,610,546, which is a continuation-in-part of application No. 14/656,580, application No. 15/099,588, which is a continuation-in-part of application No. 15/099,295, filed on Apr. 14, 2016, now abandoned, and a continuation-in-part of application No. 15/099,482, filed on Apr. 14, 2016, and a continuation-in-part of application No. 15/099,239, filed on Apr. 14, 2016, application No. 15/099,588, which is a continuation-in-part of application No. 15/099,447, filed on Apr. 14, 2016, now abandoned, and a continuation-in-part of application No. 15/099,269, filed on Apr. 14, 2016, now Pat. No. 10,418,143, application No. 15/099,588, which is a continuation-in-part of application No. 15/099,304, filed on Apr. 14, 2016, and a continuation-in-part of application No. 15/099,193, filed on Apr. 14, 2016, application No. 15/099,588, which is a continuation-in-part of application No. 15/099,464, filed on Apr. 14, 2016, now Pat. No. 10,017,852, and a continuation-in-part of application No. 15/099,289, filed on Apr. 14, 2016, now Pat. No. 10,376,845, and a continuation-in-part of application No. 15/099,410, filed on Apr. 14, 2016, now Pat. No. 10,213,746, and a continuation-in-part of application No. 15/099,099, filed on Apr. 14, 2016, application No. 15/099,588, which is a continuation-in-part of application No. 15/099,420, filed on Apr. 14, 2016, now Pat. No. 10,118,130, and a continuation-in-part of application No. 15/099,056, filed on Apr. 14, 2016, now Pat. No. 10,203,295, and a continuation-in-part of application No. 15/099,276, filed on Apr. 14, 2016, now abandoned.

(60) Provisional application No. 62/313,581, filed on Mar. 25, 2016, provisional application No. 61/934,537, filed on Jan. 31, 2014, provisional application No. 61/934,530, filed on Jan. 31, 2014, provisional application No. 61/951,930, filed on Mar. 12, 2014, provisional application No. 61/951,926, filed on Mar. 12, 2014, provisional application No. 61/951,660, filed on Mar. 12, 2014, provisional application No. 61/987,410, filed on May 1, 2014, provisional application No. 61/990,561, filed on May 8, 2014, provisional application No. 61/990,204, filed on May 8, 2014, provisional application No. 62/039,856, filed on Aug. 20, 2014, provisional application No. 62/044,877, filed on Sep. 2, 2014, provisional application No. 62/201,539, filed on Aug. 5, 2015, provisional application No. 62/201,527, filed on Aug. 5, 2015, provisional application No. 62/202,056, filed on Aug. 6, 2015, provisional application No. 62/202,122, filed on Aug. 6, 2015.

(51) Int. Cl.
 *B01D 61/24* (2006.01)
 *B01D 71/02* (2006.01)
 *B01D 67/00* (2006.01)
 *B01D 69/10* (2006.01)

(52) U.S. Cl.
 CPC ....... *B01D 61/243* (2013.01); *B01D 67/0062* (2013.01); *B01D 67/0069* (2013.01); *B01D 67/0072* (2013.01); *B01D 69/10* (2013.01); *B01D 71/021* (2013.01); *H01J 37/3056* (2013.01); *A61M 2207/00* (2013.01); *H01J 2237/3174* (2013.01)

(56) References Cited

U.S. PATENT DOCUMENTS

| | | |
|---|---|---|
| 3,303,085 A | 2/1967 | Price et al. |
| 3,501,831 A | 3/1970 | Gordon |
| 3,593,854 A | 7/1971 | Swank |
| 3,692,059 A | 9/1972 | Ice, Jr. |
| 3,701,433 A | 10/1972 | Krakauer et al. |
| 3,802,972 A | 4/1974 | Fleischer et al. |
| 3,896,733 A | 7/1975 | Rosenberg |
| 4,043,331 A | 8/1977 | Martin et al. |
| 4,073,732 A | 2/1978 | Lauer et al. |
| 4,159,954 A | 7/1979 | Gangemi |
| 4,162,220 A | 7/1979 | Servas |
| 4,277,344 A | 7/1981 | Cadotte |
| 4,303,530 A | 12/1981 | Shah et al. |
| 4,457,747 A | 7/1984 | Tu |
| 4,743,371 A | 5/1988 | Servas et al. |
| 4,804,363 A | 2/1989 | Valeri |
| 4,855,058 A | 8/1989 | Holland et al. |
| 4,880,440 A | 11/1989 | Perrin |
| 4,889,626 A | 12/1989 | Browne |
| 4,891,134 A | 1/1990 | Vcelka |
| 4,925,560 A | 5/1990 | Sorrick |
| 4,935,207 A | 6/1990 | Stanbro et al. |
| 4,976,858 A | 12/1990 | Kadoya |
| 5,052,444 A | 10/1991 | Messerly et al. |
| 5,080,770 A | 1/1992 | Culkin |
| 5,082,476 A | 1/1992 | Kahlbaugh et al. |
| 5,156,628 A | 10/1992 | Kranz |
| 5,182,111 A | 1/1993 | Aebischer et al. |
| 5,185,086 A | 2/1993 | Kaali et al. |
| 5,201,767 A | 4/1993 | Caldarise et al. |
| 5,244,981 A | 9/1993 | Seidner et al. |
| 5,277,748 A | 1/1994 | Sakaguchi et al. |

(56) References Cited

U.S. PATENT DOCUMENTS

| | | |
|---|---|---|
| 5,314,492 A | 5/1994 | Hamilton et al. |
| 5,314,960 A | 5/1994 | Spinelli et al. |
| 5,314,961 A | 5/1994 | Anton et al. |
| 5,331,067 A | 7/1994 | Seidner et al. |
| 5,344,454 A | 9/1994 | Clarke et al. |
| 5,371,147 A | 12/1994 | Spinelli et al. |
| 5,425,858 A | 6/1995 | Farmer |
| 5,480,449 A | 1/1996 | Hamilton et al. |
| 5,514,181 A | 5/1996 | Light et al. |
| 5,516,522 A | 5/1996 | Peyman et al. |
| 5,549,697 A | 8/1996 | Caldarise |
| 5,562,944 A | 10/1996 | Kafravvy |
| 5,565,210 A | 10/1996 | Rosenthal et al. |
| 5,580,530 A | 12/1996 | Kowatsch et al. |
| 5,595,621 A | 1/1997 | Light et al. |
| 5,636,437 A | 6/1997 | Kaschmitter et al. |
| 5,639,275 A | 6/1997 | Baetge et al. |
| 5,641,323 A | 6/1997 | Caldarise |
| 5,658,334 A | 8/1997 | Caldarise et al. |
| 5,662,158 A | 9/1997 | Caldarise |
| 5,665,118 A | 9/1997 | Lasalle et al. |
| 5,671,897 A | 9/1997 | Ogg et al. |
| 5,679,232 A | 10/1997 | Fedor et al. |
| 5,679,249 A | 10/1997 | Fendya et al. |
| 5,687,788 A | 11/1997 | Caldarise et al. |
| 5,700,477 A | 12/1997 | Rosenthal et al. |
| 5,713,410 A | 2/1998 | Lasalle et al. |
| 5,716,412 A | 2/1998 | Decarlo et al. |
| 5,716,414 A | 2/1998 | Caldarise |
| 5,725,586 A | 3/1998 | Sommerich |
| 5,725,775 A | 3/1998 | Bene et al. |
| 5,731,360 A | 3/1998 | Pekala et al. |
| 5,733,503 A | 3/1998 | Kowatsch et al. |
| 5,746,272 A | 5/1998 | Mastrorio et al. |
| 5,782,286 A | 7/1998 | Sommerich |
| 5,782,289 A | 7/1998 | Mastrorio et al. |
| 5,788,916 A | 8/1998 | Caldarise |
| 5,800,828 A | 9/1998 | Dionne et al. |
| 5,808,312 A | 9/1998 | Fukuda |
| 5,868,727 A | 2/1999 | Barr et al. |
| 5,897,592 A | 4/1999 | Caldarise et al. |
| 5,902,762 A | 5/1999 | Mercuri et al. |
| 5,906,234 A | 5/1999 | Mastrorio et al. |
| 5,910,172 A | 6/1999 | Penenberg |
| 5,910,173 A | 6/1999 | Decarlo et al. |
| 5,913,998 A | 6/1999 | Butler et al. |
| 5,922,304 A | 7/1999 | Unger |
| 5,925,247 A | 7/1999 | Huebbel |
| 5,932,185 A | 8/1999 | Pekala et al. |
| 5,935,084 A | 8/1999 | Southworth |
| 5,935,172 A | 8/1999 | Ochoa et al. |
| 5,954,937 A | 9/1999 | Farmer |
| 5,974,973 A | 11/1999 | Tittgemeyer |
| 5,976,555 A | 11/1999 | Liu et al. |
| 5,980,718 A | 11/1999 | Van Konynenburg et al. |
| 6,008,431 A | 12/1999 | Caldarise et al. |
| 6,013,080 A | 1/2000 | Khalili |
| 6,022,509 A | 2/2000 | Matthews et al. |
| 6,052,608 A | 4/2000 | Young et al. |
| 6,080,393 A | 6/2000 | Liu et al. |
| 6,093,209 A | 7/2000 | Sanders |
| 6,139,585 A | 10/2000 | Li |
| 6,152,882 A | 11/2000 | Prutchi |
| 6,156,323 A | 12/2000 | Verdicchio et al. |
| 6,193,956 B1 | 2/2001 | Liu et al. |
| 6,209,621 B1 | 4/2001 | Treacy |
| 6,213,124 B1 | 4/2001 | Butterworth |
| 6,228,123 B1 | 5/2001 | Dezzani |
| 6,264,699 B1 | 7/2001 | Noiles et al. |
| 6,292,704 B1 | 9/2001 | Malonek et al. |
| 6,309,532 B1 | 10/2001 | Tran et al. |
| 6,346,187 B1 | 2/2002 | Tran et al. |
| 6,375,014 B1 | 4/2002 | Garcera et al. |
| 6,423,022 B1 | 7/2002 | Roeher et al. |
| 6,426,214 B1 | 7/2002 | Butler et al. |
| 6,454,095 B1 | 9/2002 | Brisebois et al. |
| 6,455,115 B1 | 9/2002 | Demeyer |
| 6,461,622 B2 | 10/2002 | Liu et al. |
| 6,462,935 B1 | 10/2002 | Shiue et al. |
| 6,521,865 B1 | 2/2003 | Jones et al. |
| 6,532,386 B2 | 3/2003 | Sun et al. |
| 6,544,316 B2 | 4/2003 | Baker et al. |
| 6,580,598 B2 | 6/2003 | Shiue et al. |
| 6,654,229 B2 | 11/2003 | Yanagisawa et al. |
| 6,659,298 B2 | 12/2003 | Wong |
| 6,660,150 B2 | 12/2003 | Conlan et al. |
| 6,661,643 B2 | 12/2003 | Shiue et al. |
| 6,686,437 B2 | 2/2004 | Buchman et al. |
| 6,692,627 B1 | 2/2004 | Russell et al. |
| 6,695,880 B1 | 2/2004 | Roffman et al. |
| 6,699,684 B2 | 3/2004 | Ho et al. |
| 6,719,740 B2 | 4/2004 | Burnett et al. |
| 6,905,612 B2 | 6/2005 | Dorian et al. |
| 6,924,190 B2 | 8/2005 | Dennison |
| 7,014,829 B2 | 3/2006 | Yanagisawa et al. |
| 7,071,406 B2 | 7/2006 | Smalley et al. |
| 7,092,753 B2 | 8/2006 | Darvish et al. |
| 7,138,042 B2 | 11/2006 | Tran et al. |
| 7,171,263 B2 | 1/2007 | Darvish et al. |
| 7,175,783 B2 | 2/2007 | Curran |
| 7,179,419 B2 | 2/2007 | Lin et al. |
| 7,190,997 B1 | 3/2007 | Darvish et al. |
| 7,267,753 B2 | 9/2007 | Anex et al. |
| 7,306,768 B2 | 12/2007 | Chiga |
| 7,357,255 B2 | 4/2008 | Ginsberg et al. |
| 7,374,677 B2 | 5/2008 | McLaughlin et al. |
| 7,381,707 B2 | 6/2008 | Lin et al. |
| 7,382,601 B2 | 6/2008 | Yoshimitsu |
| 7,434,692 B2 | 10/2008 | Ginsberg et al. |
| 7,452,547 B2 | 11/2008 | Lambino et al. |
| 7,459,121 B2 | 12/2008 | Liang et al. |
| 7,460,907 B1 | 12/2008 | Darvish et al. |
| 7,476,222 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,505,250 B2 | 3/2009 | Cho et al. |
| 7,531,094 B2 | 5/2009 | McLaughlin et al. |
| 7,600,567 B2 | 10/2009 | Christopher et al. |
| 7,631,764 B2 | 12/2009 | Ginsberg et al. |
| 7,650,805 B2 | 1/2010 | Nauseda et al. |
| 7,674,477 B1 | 3/2010 | Schmid et al. |
| 7,706,128 B2 | 4/2010 | Bourcier |
| 7,732,301 B1 | 6/2010 | Pinnington et al. |
| 7,761,809 B2 | 7/2010 | Bukovec et al. |
| 7,786,086 B2 | 8/2010 | Reches et al. |
| 7,866,475 B2 | 1/2011 | Doskoczynski et al. |
| 7,875,293 B2 | 1/2011 | Shults et al. |
| 7,935,331 B2 | 5/2011 | Lin |
| 7,935,416 B2 | 5/2011 | Yang et al. |
| 7,943,167 B2 | 5/2011 | Kulkarni et al. |
| 7,960,708 B2 | 6/2011 | Wolfe et al. |
| 7,998,246 B2 | 8/2011 | Liu et al. |
| 8,109,893 B2 | 2/2012 | Lande |
| 8,147,599 B2 | 4/2012 | McAlister |
| 8,262,943 B2 | 9/2012 | Meng et al. |
| 8,278,106 B2 | 10/2012 | Martinson et al. |
| 8,308,702 B2 | 11/2012 | Batchvarova et al. |
| 8,316,865 B2 | 11/2012 | Ochs et al. |
| 8,329,476 B2 | 12/2012 | Pitkanen et al. |
| 8,354,296 B2 | 1/2013 | Dimitrakopoulos et al. |
| 8,361,321 B2 | 1/2013 | Stetson et al. |
| 8,449,504 B2 | 5/2013 | Carter et al. |
| 8,471,562 B2 | 6/2013 | Knizhnik |
| 8,475,689 B2 | 7/2013 | Sun et al. |
| 8,506,807 B2 | 8/2013 | Lee et al. |
| 8,512,669 B2 | 8/2013 | Hauck |
| 8,513,324 B2 | 8/2013 | Scales et al. |
| 8,535,726 B2 | 9/2013 | Dai et al. |
| 8,592,291 B2 | 11/2013 | Shi et al. |
| 8,617,411 B2 | 12/2013 | Singh |
| 8,666,471 B2 | 3/2014 | Rogers et al. |
| 8,686,249 B1 | 4/2014 | Whitaker et al. |

(56) References Cited

U.S. PATENT DOCUMENTS

| | | |
|---|---|---|
| 8,697,230 B2 | 4/2014 | Ago et al. |
| 8,698,481 B2 | 4/2014 | Lieber et al. |
| 8,715,329 B2 | 5/2014 | Robinson et al. |
| 8,721,074 B2 | 5/2014 | Pugh et al. |
| 8,734,421 B2 | 5/2014 | Sun et al. |
| 8,744,567 B2 | 6/2014 | Fassih et al. |
| 8,751,015 B2 | 6/2014 | Frewin et al. |
| 8,753,468 B2 | 6/2014 | Caldwell et al. |
| 8,759,153 B2 | 6/2014 | Elian et al. |
| 8,808,257 B2 | 8/2014 | Pugh et al. |
| 8,828,211 B2 | 9/2014 | Garaj et al. |
| 8,840,552 B2 | 9/2014 | Brauker et al. |
| 8,857,983 B2 | 10/2014 | Pugh et al. |
| 8,861,821 B2 | 10/2014 | Osumi |
| 8,894,201 B2 | 11/2014 | Pugh et al. |
| 8,940,552 B2 | 1/2015 | Pugh et al. |
| 8,950,862 B2 | 2/2015 | Pugh et al. |
| 8,974,055 B2 | 3/2015 | Pugh et al. |
| 8,975,121 B2 | 3/2015 | Pugh et al. |
| 8,979,978 B2 | 3/2015 | Miller et al. |
| 8,986,932 B2 | 3/2015 | Turner et al. |
| 8,993,234 B2 | 3/2015 | Turner et al. |
| 8,993,327 B2 | 3/2015 | McKnight et al. |
| 9,014,639 B2 | 4/2015 | Pugh et al. |
| 9,017,937 B1 | 4/2015 | Turner et al. |
| 9,023,220 B2 | 5/2015 | Zurutuza Elorza et al. |
| 9,028,663 B2 | 5/2015 | Stetson et al. |
| 9,035,282 B2 | 5/2015 | Dimitrakopoulos et al. |
| 9,045,847 B2 | 6/2015 | Batchvarova et al. |
| 9,050,452 B2 | 6/2015 | Sun et al. |
| 9,052,533 B2 | 6/2015 | Pugh et al. |
| 9,056,282 B2 | 6/2015 | Miller et al. |
| 9,062,180 B2 | 6/2015 | Scales et al. |
| 9,067,811 B1 | 6/2015 | Bennett et al. |
| 9,070,615 B2 | 6/2015 | Elian et al. |
| 9,075,009 B2 | 7/2015 | Kim et al. |
| 9,080,267 B2 | 7/2015 | Batchvarova et al. |
| 9,095,821 B1 | 8/2015 | Ratto et al. |
| 9,095,823 B2 | 8/2015 | Fleming |
| 9,096,050 B2 | 8/2015 | Bedell et al. |
| 9,096,437 B2 | 8/2015 | Tour et al. |
| 9,102,111 B2 | 8/2015 | Pugh et al. |
| 9,108,158 B2 | 8/2015 | Yu et al. |
| 9,110,310 B2 | 8/2015 | Pugh et al. |
| 9,125,715 B2 | 9/2015 | Pugh et al. |
| 9,134,546 B2 | 9/2015 | Pugh et al. |
| 9,156,700 B2 | 10/2015 | Zhamu et al. |
| 9,170,646 B2 | 10/2015 | Toner et al. |
| 9,185,486 B2 | 11/2015 | Pugh |
| 9,193,587 B2 | 11/2015 | Bennett |
| 9,195,075 B2 | 11/2015 | Pugh et al. |
| 9,225,375 B2 | 12/2015 | Pugh et al. |
| 9,388,048 B1 | 7/2016 | Zhou et al. |
| 9,425,709 B2 | 8/2016 | Hayashi et al. |
| 9,437,370 B2 * | 9/2016 | Chen ............ B82Y 30/00 |
| 9,463,421 B2 | 10/2016 | Fleming |
| 9,475,709 B2 | 10/2016 | Stetson et al. |
| 9,505,192 B2 | 11/2016 | Stoltenberg et al. |
| 9,545,600 B2 | 1/2017 | Miller et al. |
| 9,567,224 B2 | 2/2017 | Bedworth |
| 9,572,918 B2 * | 2/2017 | Bachmann ............ B01D 69/02 |
| 9,592,475 B2 * | 3/2017 | Stoltenberg ............ B01D 69/02 |
| 9,610,546 B2 | 4/2017 | Sinton et al. |
| 9,656,214 B2 | 5/2017 | Miller et al. |
| 9,708,640 B2 | 7/2017 | Wu et al. |
| 9,713,794 B2 | 7/2017 | Choi et al. |
| 9,742,001 B2 | 8/2017 | Zhamu et al. |
| 9,744,617 B2 | 8/2017 | Bedworth et al. |
| 9,870,895 B2 | 1/2018 | Bedworth |
| 10,005,038 B2 | 6/2018 | Stetson, Jr. et al. |
| 10,017,852 B2 | 7/2018 | Heise |
| 10,096,679 B1 | 10/2018 | Antunez et al. |
| 10,118,130 B2 | 11/2018 | Swett |
| 10,124,299 B2 | 11/2018 | Kim et al. |
| 10,130,919 B1 | 11/2018 | Saleh |
| 10,293,295 B2 * | 5/2019 | Wang ............ B01D 46/0075 |
| 10,376,845 B2 * | 8/2019 | Swett ............ B32B 5/16 |
| 2001/0036556 A1 | 11/2001 | Jen |
| 2001/0047157 A1 | 11/2001 | Burnett et al. |
| 2001/0055597 A1 | 12/2001 | Liu et al. |
| 2002/0079004 A1 | 6/2002 | Sato et al. |
| 2002/0079054 A1 | 6/2002 | Nakatani |
| 2002/0104435 A1 | 8/2002 | Baker et al. |
| 2002/0115957 A1 | 8/2002 | Sun et al. |
| 2002/0117659 A1 | 8/2002 | Lieber et al. |
| 2002/0183682 A1 | 12/2002 | Darvish et al. |
| 2002/0183686 A1 | 12/2002 | Darvish et al. |
| 2003/0052354 A1 | 3/2003 | Dennison |
| 2003/0134281 A1 | 7/2003 | Evans |
| 2003/0138777 A1 | 7/2003 | Evans |
| 2003/0146221 A1 | 8/2003 | Lauer et al. |
| 2003/0159985 A1 | 8/2003 | Siwy et al. |
| 2003/0171053 A1 | 9/2003 | Sanders |
| 2004/0018583 A1 | 1/2004 | Ho et al. |
| 2004/0035787 A1 | 2/2004 | Tanga et al. |
| 2004/0061253 A1 | 4/2004 | Kleinmeyer et al. |
| 2004/0063097 A1 | 4/2004 | Evans |
| 2004/0099324 A1 | 5/2004 | Fraser et al. |
| 2004/0111968 A1 | 6/2004 | Day et al. |
| 2004/0112865 A1 | 6/2004 | McCullough et al. |
| 2004/0121488 A1 | 6/2004 | Chang et al. |
| 2004/0140041 A1 | 7/2004 | Glick |
| 2004/0142463 A1 | 7/2004 | Walker et al. |
| 2004/0185730 A1 | 9/2004 | Lambino et al. |
| 2004/0193043 A1 | 9/2004 | Duchon et al. |
| 2004/0199243 A1 | 10/2004 | Yodfat |
| 2004/0208796 A1 | 10/2004 | Chiga |
| 2004/0217036 A1 | 11/2004 | Ginsberg et al. |
| 2004/0241214 A1 | 12/2004 | Kirkwood et al. |
| 2004/0251136 A1 | 12/2004 | Lean et al. |
| 2005/0004508 A1 | 1/2005 | Sun et al. |
| 2005/0004509 A1 | 1/2005 | Sun et al. |
| 2005/0004550 A1 | 1/2005 | Sun et al. |
| 2005/0010161 A1 | 1/2005 | Sun et al. |
| 2005/0010192 A1 | 1/2005 | Sun et al. |
| 2005/0015042 A1 | 1/2005 | Sun et al. |
| 2005/0053563 A1 | 3/2005 | Manissier et al. |
| 2005/0112078 A1 | 5/2005 | Boddupalli et al. |
| 2005/0126966 A1 | 6/2005 | Tanida et al. |
| 2005/0129633 A1 | 6/2005 | Lin |
| 2005/0148996 A1 | 7/2005 | Sun et al. |
| 2005/0170089 A1 | 8/2005 | Lashmore et al. |
| 2005/0189673 A1 | 9/2005 | Klug et al. |
| 2005/0226834 A1 | 10/2005 | Lambino et al. |
| 2005/0238730 A1 | 10/2005 | Le Fur et al. |
| 2006/0005381 A1 | 1/2006 | Nishi et al. |
| 2006/0036332 A1 | 2/2006 | Jennings |
| 2006/0073370 A1 | 4/2006 | Krusic et al. |
| 2006/0093885 A1 | 5/2006 | Krusic et al. |
| 2006/0121279 A1 | 6/2006 | Petrik |
| 2006/0151382 A1 | 7/2006 | Petrik |
| 2006/0166347 A1 | 7/2006 | Faulstich et al. |
| 2006/0180604 A1 | 8/2006 | Ginsberg et al. |
| 2006/0222701 A1 | 10/2006 | Kulkarni et al. |
| 2006/0253078 A1 | 11/2006 | Wu et al. |
| 2007/0004640 A1 | 1/2007 | Lin et al. |
| 2007/0032054 A1 | 2/2007 | Ramaswamy et al. |
| 2007/0056894 A1 | 3/2007 | Connors, Jr. |
| 2007/0060862 A1 | 3/2007 | Sun et al. |
| 2007/0062856 A1 | 3/2007 | Pahl et al. |
| 2007/0099813 A1 | 5/2007 | Luizzi et al. |
| 2007/0131646 A1 | 6/2007 | Donnelly et al. |
| 2007/0284279 A1 | 12/2007 | Doskoczynski et al. |
| 2008/0017564 A1 | 1/2008 | Hammond |
| 2008/0035484 A1 | 2/2008 | Wu et al. |
| 2008/0035541 A1 | 2/2008 | Franzreb et al. |
| 2008/0045877 A1 | 2/2008 | Levin et al. |
| 2008/0061477 A1 | 3/2008 | Capizzo |
| 2008/0063585 A1 | 3/2008 | Smalley et al. |
| 2008/0081323 A1 | 4/2008 | Keeley et al. |
| 2008/0081362 A1 | 4/2008 | Keeley et al. |
| 2008/0149561 A1 | 6/2008 | Chu et al. |
| 2008/0156648 A1 | 7/2008 | Dudziak et al. |
| 2008/0170982 A1 | 7/2008 | Zhang et al. |

(56) References Cited

U.S. PATENT DOCUMENTS

| | | |
|---|---|---|
| 2008/0185293 A1 | 8/2008 | Klose et al. |
| 2008/0188836 A1 | 8/2008 | Weber et al. |
| 2008/0190508 A1 | 8/2008 | Booth et al. |
| 2008/0241085 A1 | 10/2008 | Lin et al. |
| 2008/0268016 A1 | 10/2008 | Fang et al. |
| 2008/0290020 A1 | 11/2008 | Marand et al. |
| 2008/0290111 A1 | 11/2008 | Ginsberg et al. |
| 2009/0023572 A1 | 1/2009 | Backes et al. |
| 2009/0032475 A1 | 2/2009 | Ferrer et al. |
| 2009/0039019 A1 | 2/2009 | Raman |
| 2009/0048685 A1 | 2/2009 | Frigstad et al. |
| 2009/0075371 A1 | 3/2009 | Keeley et al. |
| 2009/0078640 A1 | 3/2009 | Chu et al. |
| 2009/0087395 A1 | 4/2009 | Lin et al. |
| 2009/0117335 A1 | 5/2009 | Iyoda et al. |
| 2009/0120873 A1 | 5/2009 | Becker et al. |
| 2009/0148495 A1 | 6/2009 | Hammer et al. |
| 2009/0176159 A1 | 7/2009 | Zhamu et al. |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0098741 A1 | 4/2010 | Ranade |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209330 A1 | 8/2010 | Golzhauser et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0027599 A1 | 2/2011 | Hoek et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1 | 5/2011 | Heinrich |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0132834 A1 | 6/2011 | Tomioka et al. |
| 2011/0139707 A1 | 6/2011 | Siwy et al. |
| 2011/0152795 A1 | 6/2011 | Aledo et al. |
| 2011/0186449 A1 | 8/2011 | Clochard et al. |
| 2011/0189440 A1 | 8/2011 | Appleby et al. |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0000845 A1 | 1/2012 | Park et al. |
| 2012/0031833 A1 | 2/2012 | Ho et al. |
| 2012/0048804 A1 | 3/2012 | Stetson et al. |
| 2012/0115243 A1 | 5/2012 | Pitkanen et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0219203 A1 | 8/2012 | Adachi |
| 2012/0220053 A1 | 8/2012 | Lee et al. |
| 2012/0234453 A1 | 9/2012 | Pugh et al. |
| 2012/0234679 A1 | 9/2012 | Garaj et al. |
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0294793 A1 | 11/2012 | Chen et al. |
| 2012/0298396 A1 | 11/2012 | Hong et al. |
| 2012/0301707 A1 | 11/2012 | Kinloch et al. |
| 2013/0015136 A1 | 1/2013 | Bennett |
| 2013/0034760 A1 | 2/2013 | Otts et al. |
| 2013/0045523 A1 | 2/2013 | Leach et al. |
| 2013/0056367 A1 | 3/2013 | Martinez et al. |
| 2013/0071941 A1 | 3/2013 | Miller |
| 2013/0096292 A1 | 4/2013 | Brahmasandra et al. |
| 2013/0100436 A1 | 4/2013 | Jackson et al. |
| 2013/0105417 A1 | 5/2013 | Stetson et al. |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |
| 2013/0146221 A1 | 6/2013 | Kolmakov et al. |
| 2013/0146480 A1 | 6/2013 | Garaj et al. |
| 2013/0152386 A1 | 6/2013 | Pandojirao-S et al. |
| 2013/0174968 A1 | 7/2013 | Vlassiouk et al. |
| 2013/0174978 A1 | 7/2013 | Pugh et al. |
| 2013/0176030 A1 | 7/2013 | Simon |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1* | 9/2013 | Bedworth ............ C01B 31/0484 264/483 |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |
| 2013/0270188 A1* | 10/2013 | Karnik ................ B01D 53/228 210/650 |
| 2013/0273288 A1 | 10/2013 | Luo et al. |
| 2013/0277305 A1 | 10/2013 | Stetson et al. |
| 2013/0277573 A1 | 10/2013 | Miller et al. |

(56) References Cited

U.S. PATENT DOCUMENTS

| | | |
|---|---|---|
| 2013/0284665 A1 | 10/2013 | Lee et al. |
| 2013/0295150 A1 | 11/2013 | Chantalat et al. |
| 2013/0295374 A1 | 11/2013 | Tang et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0330833 A1 | 12/2013 | Ruiz et al. |
| 2013/0335092 A1 | 12/2013 | Wu |
| 2013/0338611 A1 | 12/2013 | Pugh et al. |
| 2013/0338744 A1 | 12/2013 | Frewin et al. |
| 2014/0002788 A1 | 1/2014 | Otts et al. |
| 2014/0005514 A1 | 1/2014 | Pugh et al. |
| 2014/0015160 A1 | 1/2014 | Kung et al. |
| 2014/0017322 A1 | 1/2014 | Dai et al. |
| 2014/0021133 A1 | 1/2014 | Siwy et al. |
| 2014/0030482 A1 | 1/2014 | Miller et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |
| 2014/0174927 A1 | 6/2014 | Bashir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0253131 A1 | 9/2014 | Liu et al. |
| 2014/0257348 A1 | 9/2014 | Priewe et al. |
| 2014/0257515 A1 | 9/2014 | So et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1* | 9/2014 | Stoltenberg ............ B01D 69/02 210/500.25 |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1 | 9/2014 | Stoltenberg et al. |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0311967 A1 | 10/2014 | Grossman et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0346631 A1 | 11/2014 | Karim et al. |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0050734 A1 | 2/2015 | Liedtke et al. |
| 2015/0053627 A1 | 2/2015 | Silin et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0076056 A1 | 3/2015 | Iyuke et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0137817 A1 | 5/2015 | Wilson et al. |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0151254 A1 | 6/2015 | Perez |
| 2015/0170788 A1 | 6/2015 | Miller et al. |
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0196879 A1 | 7/2015 | Brinke-Seiferth et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |
| 2015/0221474 A1 | 8/2015 | Bedworth |
| 2015/0231557 A1 | 8/2015 | Miller et al. |
| 2015/0231577 A1 | 8/2015 | Nair et al. |
| 2015/0247178 A1 | 9/2015 | Mountcastle et al. |
| 2015/0248972 A1 | 9/2015 | Tang et al. |
| 2015/0258254 A1 | 9/2015 | Simon et al. |
| 2015/0258498 A1 | 9/2015 | Simon et al. |
| 2015/0258502 A1 | 9/2015 | Turowski |
| 2015/0258503 A1 | 9/2015 | Sinton et al. |
| 2015/0258506 A1 | 9/2015 | Mi et al. |
| 2015/0258525 A1 | 9/2015 | Westman et al. |
| 2015/0268150 A1 | 9/2015 | Newkirk et al. |
| 2015/0272834 A1 | 10/2015 | Sun et al. |
| 2015/0272896 A1 | 10/2015 | Sun et al. |
| 2015/0273401 A1 | 10/2015 | Miller et al. |
| 2015/0309337 A1 | 10/2015 | Flitsch et al. |
| 2015/0321147 A1 | 11/2015 | Fleming et al. |
| 2015/0321149 A1 | 11/2015 | McGinnis |
| 2015/0323811 A1 | 11/2015 | Flitsch et al. |
| 2015/0336202 A1 | 11/2015 | Bedworth et al. |
| 2015/0342900 A1 | 12/2015 | Putnins |
| 2015/0346382 A1 | 12/2015 | Bliven et al. |
| 2015/0351887 A1 | 12/2015 | Peters |
| 2015/0359742 A1 | 12/2015 | Fassih et al. |
| 2015/0376448 A1 | 12/2015 | Urs |
| 2015/0378176 A1 | 12/2015 | Flitsch et al. |
| 2016/0009049 A1 | 1/2016 | Stoltenberg et al. |
| 2016/0038885 A1 | 2/2016 | Hogen-Esch et al. |
| 2016/0043384 A1 | 2/2016 | Zhamu et al. |
| 2016/0058932 A1 | 3/2016 | Stetson et al. |
| 2016/0059190 A1 | 3/2016 | Yoo et al. |

(56) References Cited

U.S. PATENT DOCUMENTS

| | | | |
|---|---|---|---|
| 2016/0067390 A1 | 3/2016 | Simon et al. | |
| 2016/0074814 A1 | 3/2016 | Park et al. | |
| 2016/0074815 A1 | 3/2016 | Sinton et al. | |
| 2016/0084008 A1 | 3/2016 | Faircloth et al. | |
| 2016/0084981 A1 | 3/2016 | Kayano et al. | |
| 2016/0116237 A1 | 4/2016 | Alsadah et al. | |
| 2016/0256805 A1 | 9/2016 | Grein et al. | |
| 2016/0272499 A1 | 9/2016 | Zurutuza Elorza et al. | |
| 2016/0282326 A1 | 9/2016 | Waduge et al. | |
| 2016/0284811 A1 | 9/2016 | Yu et al. | |
| 2016/0339160 A1* | 11/2016 | Bedworth | A61M 1/1623 |
| 2017/0000937 A1 | 1/2017 | Gottschalk | |
| 2017/0028640 A1 | 2/2017 | Harrison et al. | |
| 2017/0032962 A1 | 2/2017 | Zurutuza Elorza et al. | |
| 2017/0035943 A1* | 2/2017 | Simon | A61L 31/024 |
| 2017/0036916 A1* | 2/2017 | Bedworth | C01B 31/0484 |
| 2017/0037356 A1 | 2/2017 | Simon et al. | |
| 2017/0057812 A1 | 3/2017 | Zurutuza Elorza et al. | |
| 2017/0065939 A1 | 3/2017 | Kim et al. | |
| 2017/0144107 A1 | 5/2017 | Garaj et al. | |
| 2017/0202885 A1 | 7/2017 | Agulnick | |
| 2017/0216923 A1 | 8/2017 | Babenko et al. | |
| 2017/0217777 A1 | 8/2017 | Hong et al. | |
| 2017/0239623 A1* | 8/2017 | Stoltenberg | B01D 69/02 |
| 2017/0296706 A1 | 10/2017 | Simon et al. | |
| 2017/0296972 A1 | 10/2017 | Sinton et al. | |
| 2017/0296976 A1 | 10/2017 | Liu et al. | |
| 2017/0296979 A1* | 10/2017 | Swett | B01D 69/12 |
| 2018/0147542 A1 | 5/2018 | Jhon et al. | |
| 2018/0207591 A1 | 7/2018 | Yu et al. | |

FOREIGN PATENT DOCUMENTS

| | | |
|---|---|---|
| CN | 1128501 A | 8/1996 |
| CN | 101108194 A | 1/2008 |
| CN | 101243544 | 8/2008 |
| CN | 101428198 A | 5/2009 |
| CN | 101489653 A | 7/2009 |
| CN | 101996853 A | 3/2011 |
| CN | 102242062 A | 11/2011 |
| CN | 102344132 | 2/2012 |
| CN | 102423272 | 4/2012 |
| CN | 102592720 A | 7/2012 |
| CN | 101996853 B | 8/2012 |
| CN | 102637584 A | 8/2012 |
| CN | 103153441 | 6/2013 |
| CN | 103182249 A | 7/2013 |
| CN | 203235358 | 10/2013 |
| CN | 103480281 | 1/2014 |
| CN | 103585891 | 2/2014 |
| CN | 103603706 A | 2/2014 |
| DE | 19536560 | 3/1997 |
| DE | 10 2005 049 388 A1 | 4/2007 |
| EP | 0 364 628 A1 | 4/1990 |
| EP | 1 034 251 | 1/2004 |
| EP | 1 777 250 A1 | 4/2007 |
| EP | 1 872 812 | 1/2008 |
| EP | 2 060 286 | 5/2009 |
| EP | 2 107 120 A1 | 10/2009 |
| EP | 2 230 511 A1 | 9/2010 |
| EP | 1 603 609 | 5/2011 |
| EP | 2 354 272 | 8/2011 |
| EP | 2 450 096 | 5/2012 |
| EP | 2 489 520 | 8/2012 |
| EP | 2 511 002 | 10/2012 |
| EP | 2 586 473 | 5/2013 |
| EP | 2 679 540 | 1/2014 |
| EP | 2 937 313 | 10/2015 |
| EP | 2 995 368 A1 | 3/2016 |
| EP | 3 070 053 | 9/2016 |
| EP | 3 084 398 | 10/2016 |
| EP | 1 538 2430.5 | 3/2017 |
| EP | 3 135 631 | 3/2017 |
| JP | 59-102111 | 7/1984 |
| JP | 10-510471 | 5/1995 |
| JP | 7504120 | 5/1995 |
| JP | 2001-232158 | 8/2001 |
| JP | 2002-126510 | 5/2002 |
| JP | 2004-179014 | 6/2004 |
| JP | 2005-126966 | 5/2005 |
| JP | 2006-188393 | 7/2006 |
| JP | 2006-262891 A | 10/2006 |
| JP | 2009-291777 | 12/2009 |
| JP | 2011-168448 A | 9/2011 |
| JP | 2011-241479 | 12/2011 |
| JP | 2012-500708 | 1/2012 |
| JP | 2013-536077 A | 9/2013 |
| JP | 2004-202480 | 7/2014 |
| JP | 2015-503405 | 2/2015 |
| JP | 2016-175828 | 10/2016 |
| KR | 1020110084110 | 7/2011 |
| KR | 10-2012-022164 A | 3/2012 |
| KR | 1020120022164 A | 3/2012 |
| KR | 1020140002570 | 1/2014 |
| WO | WO-93/33901 | 3/1993 |
| WO | WO-93/12859 | 8/1993 |
| WO | WO-95/00231 | 1/1995 |
| WO | WO-97/12664 A1 | 4/1997 |
| WO | WO-98/30501 A2 | 7/1998 |
| WO | WO-00/70012 | 11/2000 |
| WO | WO-02/055539 A1 | 7/2002 |
| WO | WO-2013/115762 | 8/2003 |
| WO | WO-2004/009840 A1 | 1/2004 |
| WO | WO-2004/082733 | 9/2004 |
| WO | WO-2005/047857 A2 | 5/2005 |
| WO | WO-2007/103411 A2 | 9/2007 |
| WO | WO-2007/140252 A1 | 12/2007 |
| WO | WO-2008/008533 | 1/2008 |
| WO | WO-2009/129984 A1 | 10/2009 |
| WO | WO-2010/006080 | 1/2010 |
| WO | WO-2010/115904 A1 | 10/2010 |
| WO | WO-2011/019686 A1 | 2/2011 |
| WO | WO-2011/046706 A1 | 4/2011 |
| WO | WO-2011/001674 | 6/2011 |
| WO | WO-2011/063458 A1 | 6/2011 |
| WO | WO-2011/075158 | 6/2011 |
| WO | WO-2011/094204 A2 | 8/2011 |
| WO | WO-2011/100458 A2 | 8/2011 |
| WO | WO-2011/138689 A2 | 11/2011 |
| WO | WO-2012/006657 A1 | 1/2012 |
| WO | WO-2012/021801 A2 | 2/2012 |
| WO | WO-2012/027148 A1 | 3/2012 |
| WO | WO-2012/028695 | 3/2012 |
| WO | WO-2012/030368 A1 | 3/2012 |
| WO | WO-2012/073998 A1 | 6/2012 |
| WO | WO-2012/125770 | 9/2012 |
| WO | WO-2012/138671 A2 | 10/2012 |
| WO | WO-2012/142852 A1 | 10/2012 |
| WO | WO-2013/016445 A1 | 1/2013 |
| WO | WO-2013/048063 A1 | 4/2013 |
| WO | WO-2013/138137 A1 | 9/2013 |
| WO | WO-2013/138698 A1 | 9/2013 |
| WO | WO-2013/142133 | 9/2013 |
| WO | WO-2013/142539 | 9/2013 |
| WO | WO-2013/151799 | 10/2013 |
| WO | WO-2013/152179 A1 | 10/2013 |
| WO | WO-2014/038600 A1 | 3/2014 |
| WO | WO-2014/084856 | 6/2014 |
| WO | WO-2014/084861 A1 | 6/2014 |
| WO | WO-2014/149043 | 10/2014 |
| WO | WO-2014/168629 A1 | 10/2014 |
| WO | WO-2014/204722 A1 | 12/2014 |
| WO | WO-2015/030698 A1 | 3/2015 |
| WO | WO-2015/110277 | 7/2015 |
| WO | WO-2015/116857 | 8/2015 |
| WO | WO-2015/116946 | 8/2015 |
| WO | WO-2015/138736 A1 | 9/2015 |
| WO | WO-2015/138752 A1 | 9/2015 |
| WO | WO-2015/1138771 A1 | 9/2015 |
| WO | WO-2015/197217 | 12/2015 |

(56) References Cited

FOREIGN PATENT DOCUMENTS

| WO | WO-2016/036888 A1 | 3/2016 |
|---|---|---|
| WO | WO-2016/102003 | 6/2016 |

OTHER PUBLICATIONS

Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc., "Filmtec Nanofiltration Membrane Elements", Retrieved from appliedmembranes.com/nanofiltration_elements.htm, accessed Apr. 28, 2015 (2 Pages).
Aso et al., "Comparison of serum high-molecular weight (HMW) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
AU Examination Report for Australian Patent Application No. 2013235234, dated Jan. 13, 2017, 4 pages.
AU Notice of Acceptance for Australian Application No. 2011293742 dated Jan. 13, 2016.
Axelsson et al., "Acute hyperglycemia induces rapid, reversible increases in glomerular permeability in nondiabetic rats," AM. J. Physiol. Renal Physiol. 298(6): F1306-F1312 (Jun. 2010) (available online Mar. 17, 2010).
Bains et al., "Novel lectins from rhizomes of two Acorus species with mitogenic activity and inhibitory potential towards murine cancer cell lines," Int'l Immunopharmacol. 5(9): 1470-1478 (Aug. 2005) (available online May 12, 2005).
Baker, "Membrane Technology and Applications", Membrane Technology and Applications; Apr. 14, 2004; pp. 92-94.
Barreiro et al. "Transport properties of graphene in the high-current limit." Physical review letters 103.7 (2009): 076601.
Bazargani et al. "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Bieri et al. "Two-dimensional Polymer Formation on Surfaces: Insight into the Roles of Precursor Mobility and Reactivity" JACS, 2010, vol. 132, pp. 16669-16676.
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Chu Ju, et al. "Modern Biotechnology" East China University of Technology Press, (Sep. 2007), vol. 1; pp. 306-307, ISBN 978-7-5628-2116-8.
Clochard, "Track-Etched Polymer Membranes," Laboratory of Irradiated Solids, Ecole Polytechnique, retrieved from http://www.lsi.polytechnique.fr/home/research/physics-and-chemistry-of-nano-objects/trac . . . , Accessed Jul. 30, 2015 (2 pages).
CN Notification of Grant for Chinese Application No. 201180049184.5 dated Jun. 6, 2016.
CN Office Action for Chinese Application No. 201380014845.X dated Jul. 8, 2016.
CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.
CN Office Action for Chinese Application No. 201180049118.5 dated Jun. 15, 2015.
CN Office Action for Chinese Application No. 201180049184.5 dated Jul. 30, 2014.
CN Office Action for Chinese Application No. 201180049184.5 dated Mar. 4, 2016.
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 dated Oct. 27, 2015.
Corresponding U.S. Appl. No. 13/802,896, filed Mar. 14, 2013.
Corresponding U.S. Appl. No. 13/803,958, filed Mar. 14, 2013.
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).
Edwards, "Large Sheets of Graphene Film Produced for Transparent Electrodes (w/ Video)"; (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
Exhibit A as filed with Preliminary Amendment in corresponding U.S. Appl. No. 12/868,150.
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Georgakilas et al., "Functionalization of Graphene: Covalent and Non-Covalent Approaches, Derivatives and Applications," Chem. Rev., (2012) 112(11), pp. 6156-6214.
Gnudi "Molecular mechanisms of proteinuria in diabetes," Biochem. Soc. Trans. 36(5): 946-949 (Oct. 2008).

(56) References Cited

OTHER PUBLICATIONS

Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).
Harvey "Carbon as conductor: a pragmatic view." Proceedings of the 61st IWCS Conference, http://www.iwcs.org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of Fe3 O4 nanoparticles to graphene oxide by covalent bonding." Carbon 48.11 (2010): 3139-3144.
Hone et al. "Graphene has record-breaking strength" Physicsworld. com, Jul. 17, 2008.
Huang et al., "Gene expression profile in circulating mononuclear cells afterexposure to ultrafine carbon particles," Inhalation Toxicol. 22(10): 835-846 (Aug. 2010).
Humplik, et al. "Nanostructured materials for water desalination." Nanotechnology 22.29 (2011): 292001.
International Preliminary Report on Patentability dated Oct. 1, 2014, for related International Application No. PCT/US2013/033403.
International Preliminary Report on Patentability dated Oct. 15, 2012, for related International Application No. PCT/US11/47800.
International Preliminary Report on Patentability dated Sep. 15, 2015, corresponding to International Application No. PCT/US2014/021677.
International Preliminary Report on Patentability dated Sep. 24, 2015, corresponding to International Patent Application No. PCT/US2014/023043.
International Preliminary Report on Patentability for PCT Application No. PCT/US2014/023027 dated Sep. 15, 2015.
International Preliminary Report on Patentability for PCT Application No. PCT/US2014/041766 dated Dec. 30, 2015.
International Preliminary Report on Patentability for PCT/US15/22300 dated Oct. 6, 2016.
International Preliminary Report on Patentability for PCT/US2013/033035 dated Sep. 23, 2014.
International Preliminary Report on Patentability for PCT/US2013/074942 dated Jun. 22, 2015.
International Preliminary Report on Patentability for PCT/US2015/020287 dated Sep. 22, 2016.
International Preliminary Report on Patentability dated Mar. 22, 2016 for International Application No. PCT/US2014/051011.
International Search Report and Written Opinion dated Jan. 5, 2012 for related International Application No. PCT/US11/47800.
International Search Report and Written Opinion dated Mar. 12, 2014 for International Application No. PCT/US2013/074942.
International Search Report and Written Opinion for International Application No. PCT/US2011/047800 dated Jan. 5, 2012.
International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.
International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2014/041766, dated Sep. 30, 2014.
International Search Report and Written Opinion dated Jun. 5, 2014 in International Application No. PCT/US2014/021677.
International Search Report and Written Opinion dated Jun. 6, 2014 in International Application No. PCT/US2014/023043.
International Search Report and Written Opinion dated Dec. 16, 2014, for International Application No. PCT/US2014/051011.
International Search Report and Written Opinion dated Jun. 19, 2015, in International Application No. PCT/US2015/020287.

Inui et al. "Molecular dynamics simulations of nanopore processing in a graphene sheet by using gas cluster ion beam." Applied Physics A: Materials Science & Processing 98.4 (2010): 787-794.
Israelachvili, "Intermolecular and Surface Forces," 3rd ed., Chap. 7.1, Sizes of Atoms, Molecules, and Ions, 2011, 1 page.
Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).
JP Office Action in Japanese Application No. 2015-501729 dated Dec. 9, 2016 (English translation).
JP Office Action in Japanese Application No. 2015-501867 dated Oct. 11, 2016 (English translation).
JP Office Action in Japanese Application No. 2015-503405 dated Nov. 14, 2016 (English translation).
JP Office Action in Japanese Application No. 2015-503406 dated Dec. 6, 2016(English translation).
Kang et al., "Effect of eplerenone, enalapril and their combination treatment on diabetic nephropathy in type II diabetic rats," Nephrol. Dialysis Transplant. 24(1): 73-84 (Jan. 2009).
Kang et al., "Efficient Transfer of Large-Area Graphene Films onto Rigid Substrates by Hot Pressing," American Chemical Society Nano, 6(6): 5360-5365(May 28, 2012).
Kar et al., "Effect of glycation of hemoglobin on its interaction with trifluoperazine," Protein J. 25(3): 202-211 (Apr. 2006) (available online Jun. 6, 2006).
Kawamoto et al., "Serum high molecular weight adiponectin is associated with mild renal dysfunction in Japanese adults," J. Atherosclerosis Thrombosis 17(11): 1141-1148 (Nov. 27, 2011).
Khun et al. "From Microporous Regular Frameworks to Mesoporous Materials with Ultrahigh Surface Area: Dynamic reorganization of Porous Polymer Network" JACS, 2008; vol. 130; pp. 13333-13337.
Krupka et al., "Measurements of the Sheet Resistance and Conductivity of Thin Epitaxial Graphene and SiC Films" Applied Physics Letters 96, 082101-I; Feb. 23, 2010.
Kumar et al., "Modulation of alpha-crystallin chaperone activity in diabetic rat lens by curcumin," Molecular Vision 11: 561-568 (Jul. 26, 2005).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Lucchese et al. "Quantifying ion-induced defects and Raman relaxation length in graphene." Carbon 48.5 (2010): 1592-1597.
Macleod et al. "Supramolecular Orderinng in Oligothiophene-Fullerene Monolayers" JACS, 2009, vol. 131, pp. 16844-16850.
Mattevi et al. "A review of chemical vapour deposition of graphene on copper." Journal of Materials Chemistry 21.10 (2011): 3324-3334.
Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Nafea, et al. "Immunoisolating semi-permeable membranes for cell encapsulation: focus on hydrogels." J Control Release. 154(2): 110-122 (Sep. 5, 2011).
Nezlin, "Circulating non-immune IgG complexes in health and disease," Immunol. Lett. 122(2); 141-144 (Feb. 21, 2009) (available online Feb. 2, 2009).
Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).
Ogawa et al., "Exosome-like vesicles in Gloydius blomhoffii blomhoffii venom," Toxicon 51(6): 984-993 (May 2008) (available online Feb. 19, 2008).

(56) References Cited

OTHER PUBLICATIONS

Ohgawara et al. "Assessment of pore size of semipermeable membrane for immunoisolation on xenoimplatntation of pancreatic B cells using a diffusion chamber." Transplant Proc. (6): 3319-3320. 1995.
Oki et al., "Combined acromegaly and subclinical Cushing disease related to high-molecular-weight adrenocorticotropic hormone," J. Neurosurg. 110(2): 369-73 (Feb. 2009).
Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).
Osorio et al., "Effect of phlorizin on SGLT2 expression in the kidney of diabetic rats," J. Nephrol. 23(5): 541-546 (Sep.-Oct. 2010).
Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).
Pall Corporation, "Pall Water Processing Disc-Tube Filter Technology", Retrieved on Feb. 10, 2015, Retrieved from http://www.pall.com /pdfs/Fuels-and-Chemicals/Disc-Tube_Filter_Technoloqy-DT100b.pdF (15 Pages).
PCT International Preliminary Report on Patentability in corresponding application No. PCT/US2013/033400 dated Oct. 1, 2014.
Plant et al. "Size-dependent propagation of Au nanoclusters through few-layer grapheme," The Royal Society of Chemistry 2013, Nanoscale.
Pollard, "Growing Graphene via Chemical Vapor" Department of Physics, Pomona College; May 2, 2011.
Preliminary Amendment filed in corresponding U.S. Appl. No. 12/868,150.
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1—Expressing Pancreatic Progenitor Cells Accelerates the Maturation of Insulin-Secreting Cells In Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).
Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.
SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Sethna et al., "Serum adiponectin levels and ambulatory blood pressure monitoring in pediatric renal transplant recipients," Transplantation 88(8): 1030-1037 (Oct. 27, 2009).
Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).

Swett et al, "Imagining and Sculpting Graphene on the atomic scale" Oak Ridge National Laboratory's (ORNL) Center for Nanophase Materials Sciences (CNMS) Biannual Review. 1 page.
Swett et al, "Supersonic Nanoparticle Interaction with Suspended CVD Graphene", Microsc. Microanal. 22 (Suppl 3): 1670-1671 (Jul. 25, 2016).
Takata et al., "Hyperresistinemia is associated with coexistence of hypertension and type 2 diabetes," Hypertension 51. 2 (Feb. 2008): 534-9.
Tamborlane et al., "Continuous Glucose Monitoring and Intensive Treatment of Type 1 Diabetes" N Engl J Med 359;14: 1464-1476 (Oct. 2, 2008).
Tanugi et al., "Nanoporous Graphene Could Outperform Best Commercial Water Desalination Techniques,"; ACS 2012; Jun. 25, 2012; Weftec 2012; Sep. 29-Oct. 3.
Totani et al. "Gluten binds cytotoxic compounds generated in heated frying oil." Journal of oleo science 57.12 (2008): 683-690.
Tsukamoto et al. "Purification, characterization and biological activities of a garlic oliqosaccharide," Journal of UOEH 30.2 (Jun. 1, 2008): 147-57.
TW Office Action in Taiwanese Application No. 102146079 dated Apr. 14, 2017. 9 Pages.(English translation).
TW Search Report in Taiwanese Application No. 102146079 dated Apr. 14, 2017. 1 page.
UMEA Universitet "Graphene nanoscrolls are formed by decoration of magnetic nanoparticles." ScienceDaily. Aug. 15, 2013. https://www.sciencedaily.com/releases/2013/08/130815084402.htm (3 pages).
US Corrected Notice of Allowance in U.S. Appl. No. 14/819,273 dated Apr. 12, 2017.
US Notice of Allowance for U.S. Appl. No. 12/868,150 dated Sep. 25, 2012.
US Notice of Allowance for U.S. Appl. No. 13/548,539 dated Aug. 18, 2015.
US Notice of Allowance for U.S. Appl. No. 13/548,539 dated Jul. 23, 2015.
US Notice of Allowance for U.S. Appl. No. 13/719,579 dated May 20, 2016.
US Notice of Allowance for U.S. Appl. No. 13/795,276 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 13/923,503 dated Oct. 14, 2016.
U.S. Notice of Allowance for U.S. Appl. No. 13/923,503 dated Oct. 5, 2016.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/610,770 dated May 5, 2017.
U.S. Notice of Allowance in U.S. Appl. No. 14/656,580 dated May 8, 2017.

(56) References Cited

OTHER PUBLICATIONS

U.S. Notice of Allowance in U.S. Appl. No. 14/819,273 dated Jun. 9, 2017.
U.S. Notice of Allowance in U.S. Appl. No. 15/099,464 dated Jun. 16, 2017.
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.
U.S. Office Action for U.S. Appl. No. 13/923,503 dated Mar. 22, 2016.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016.
U.S. Office Action for U.S. Appl. No. 14/203,655 dated Aug. 10, 2016.
U.S. Office Action for U.S. Appl. No. 14/656,190 dated May 18, 2017.
U.S. Office Action for U.S. Appl. No. 14/686,452 dated Jun. 9, 2017.
U.S. Office Action for U.S. Appl. No. 14/856,471 dated May 31, 2017.
U.S. Office Action for U.S. Appl. No. 14/858,741 dated Dec. 1, 2016.
U.S. Office Action for U.S. Appl. No. 15/289,944 dated Feb. 9, 2017.
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/193,007 dated Apr. 24, 2017.
U.S. Office Action in U.S. Appl. No. 14/656,617 dated Apr. 4, 2017.
U.S. Office Action on U.S. Appl. No. 14/656,335 dated Apr. 25, 2017.
U.S. Office Action on U.S. Appl. No. 15/332,982 dated Jan. 30, 2017.
U.S. Supplemental Notice of Allowance for U.S. Appl. No. 13/795,276 dated Nov. 29, 2016.
Vallon,"Micropuncturing the nephron," Pflugers Archiv : European journal of physiology 458. 1 (May 2009): 189-201.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de CI's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vriens et al. "Methodological considerations in quantification of oncological FDG PET studies." European journal of nuclear medicine and molecular imaging 37.7 (2010): 1408-1425.

Wang et al., "Direct Observation of a Long-Lived Single-Atom Catalyst Chiseling Atomic Structures in Graphene," Nano Lett., 2014, pp. A-F.
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wang et al.,"What is the role of the second "structural " NADP+-binding site in human glucose 6-phosphate dehydrogenase?,"Protein science a publication of the Protein Society 17. 8 (Aug. 2008): 1403-11.
Wei et al., "Synthesis of N-doped graphene by chemical vapor deposition and its electrical properties", Nano Lett. 2009 9 1752-58.
Written Opinion dated Mar. 12, 2014 for related International Application No. PCT/US2013/074942.
Written Opinion for PCT/US11/47800 dated Jan. 5, 2012.
Written Opinion for PCT/US2013/074942 date Mar. 12, 2014.
Written Opinion in corresponding application No. PCT/US2013/030344 dated Jun. 19, 2013.
Written Opinion in corresponding application No. PCT/US2013/033400 dated Jun. 28, 2013.
Written Opinion in corresponding application No. PCT/US2013/033403 dated Jun. 28, 2013.
Written Opinion dated Jun. 5, 2014 in corresponding application No. PCT/US2014/021677.
Written Opinion dated Jun. 6, 2014 in corresponding application No. PCT/US2014/023043.
Written Opinion dated Jun. 19, 2013 in corresponding application No. PCT/US2013/030344.
Written Opinion dated Jun. 26, 2014 in corresponding application No. PCT/US2014/023027.
Written Opinion dated Jun. 28, 2013 in corresponding application No. PCT/US2013/033035.
Written Opinion of the International Searching Authority dated Dec. 16, 2014, for International Application No. PCT/US2014/051011.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie et al., "Fractionation and characterization of biologically-active polysaccharides from Artemisia tripartite," Phytochemistry 69. 6 (Apr. 2008): 1359-71.
Xie, et al. "Controlled fabrication of high-quality carbon nanoscrolls from monolayer graphene." Nano letters 9.7 (2009): 2565-2570.
Yagil et al. "Nonproteinuric diabetes-associated nephropathy in the Cohen rat model of type 2 diabetes" Diabetes 54. 5 (May 2005): 1487-96.
Zan et al. "Interaction of Metals with Suspended Graphene Observed by Transmission Electron Microscopy", J. Phys. Chem. Lett., Mar. 8, 2012, 3, 953-958.
Zhang et al. "Effect of Chemical Oxidation on the Structure of Single-Walled Carbon Nanotubes", J. Phys. Chem., Feb. 12, 2003, B 107 3712-8.
Zhang et al. "Method for anisotropic etching of graphite or graphene" Institute of Physics, Chinese Academy of Sciences; PEOP. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al. "Isolation and activity of an alpha-amylase inhibitor from white kidney beans," Yao xue xue bao =Acta pharmaceutica Sinica 42. 12 (Dec. 2007): 1282-7.
Zhao, et al. "Efficient preparation of large-area graphene oxide sheets for transparent conductive films." ACS nano 4.9 (2010): 5245-5252.
Zhou, K., et al., "One-pot preparation of graphene/ Fe3O4 composites by a solvothermal reaction," New J. Chem., 2010, 34, 2950.
Zhu et al. "Carbon Nanotubes in Biomedicine and Biosensing", Carbon Nanotubes-Growth and Applications, InTech, (Aug. 9, 2011) Chapter 6: pp. 135-162. Available from: https://www.intechopen.com/books/carbon-nanotubes-growth-and-applications/carbon-nanotubes-in-biomedicine-and-biosensing.

(56) References Cited

OTHER PUBLICATIONS

Ziegelmeier et al. "Adipokines influencing metabolic and cardiovascular disease are differentially regulated in maintenance hemodialysis," Metabolism: clinical and experimental 57. 10 (Oct. 2008): 1414-21.
Zirk et al. "A refractometry-based glucose analysis of body fluids," Medical engineering & physics 29. 4 (May 2007): 449-58.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages).
Barreiro et al. "Understanding the catalyst-free transformation of amorphous carbon into graphene by current-induced annealing," Scientific Reports, 3 (Article 1115): 1-6 (Jan. 2013).
Botari et al., "Graphene healing mechanisms: A theoretical investigation," Carbon, 99: 302-309 (Apr. 2016) (published online Dec. 2015).
Chen et al., "Defect Scattering in Graphene," Physical Review Letters, 102: 236805-1-236805-4 (Jun. 2009).
Chen et al., "Self-healing of defected graphene," Applied Physics Letters, 102(10): 103107-1-103107-5 (Mar. 2013).
Cheng et al., "Ion Transport in Complex Layered Graphene-Based Membranes with Tuneable Interlayer Spacing," Science Advances 2(2): 1501272 (Feb. 12, 2016).
Crock et al., "Polymer Nanocomposites with Graphene-Based Hierarchical Fillers as Materials for Multifunctional Water Treatment Membranes." Water Research 47(12): 3984-3996 (Aug. 2013; first published online Mar. 29, 2013).
Han et al., "Ultrathin Graphene Nanofiltration Membrane for Water Purification." Advanced Functional Materials 23(29): 3693-3700 (Aug. 1, 2013).
International Search Report and Written Opinion in PCT/US2016/027583 dated Jan. 13, 2017.
International Search Report and Written Opinion in PCT/US2016/027594 dated Jan. 13, 2017.
International Search Report and Written Opinion in PCT/US2016/027628 dated Jan. 9, 2017.
International Search Report and Written Opinion in PCT/US2016/027631 dated Jan. 13, 2017.
International Search Report and Written Opinion in PCT/US2016/027632 dated Jan. 9, 2017.
International Search Report in PCT/US2016/027629 dated Dec. 8, 2016.
International Search Report in PCT/US2016/052007 dated Dec. 27, 2016.
Kjeldsen, T., "Yeast secretory expression of insulin precursors," Appl Microbiol Biotechnol, 54: 277-286 (May 2000).
Lin et al., "A Direct and Polymer-Free Method for Transferring Graphene Grown by Chemical Vapor Deposition to Any Substrate," ACSNANO, 8(2): 1784-1791 (Jan. 2014).
Liu et al. "Synthesis of high-quality monolayer and bilayer graphene on copper using chemical vapor deposition," Carbon, 49(13): 4122-4130 (Nov. 2011) (published online May 2011).
O'Hern et al., "Nanofiltration across defect-sealed nanoporous monolayer graphene," Nano Letters, 15(5): 3254-3260 (Apr. 2015).
U.S. Corrected Notice of Allowance in U.S. Appl. No. 13/480,569 dated May 26, 2015.
U.S. Notice of Allowance for U.S. Appl. No. 14/610,770 dated Apr. 25, 2016.
U.S. Notice of Allowance in U.S. Appl. No. 14/819,273 dated Dec. 14, 2016.
U.S. Notice of Allowance in U.S. Appl. No. 13/480,569 dated Feb. 27, 2015.
U.S. Office Action in U.S. Appl. No. 13/480,569 dated Jul. 30, 2014.
U.S. Office Action in U.S. Appl. No. 14/856,471 dated Dec. 1, 2016.
U.S. Restriction Requirement in U.S. Appl. No. 14/193,007 dated Jul. 17, 2015.

Wang et al., "Graphene Oxide Membranes with Tunable Permeability due to Embedded Carbon Dots." Chemical Communications 50(86): 13089-13092 (Nov. 2014; first published online Sep. 3, 2014).
Written Opinion in PCT/US2016/027590 dated Jan. 6, 2017.
Written Opinion in PCT/US2016/052010 dated Dec. 20, 2016.
Xu et al., "Graphene Oxide-TiO2 Composite Filtration Membranes and their Potential Application for Water Purification." Carbon 62: 465-471 (Oct. 2013; first published online Jun. 21, 2013).
Zhao et al., "A glucose-responsive controlled release of insulin system based on enzyme multilayers-coated mesoporous silica particles," Chem. Commun., 47: 9459-9461 (Jun. 2011).
International Search Report and Written Opinion dated Jul. 5, 2017 from related PCT application PCT/US2017/024147.
U.S. Office Action for U.S. Appl. No. 14/843,944 dated Jun. 23, 2017.
CN Office Action in Chinese Application No. 201580006829.5 dated Aug. 1, 2017. (English translation) (8 pages).
EP Office Action for European Application No. 15743307.9 dated Aug. 8, 2017. (17 pages).
European Search Report dated Aug. 28, 2017 from related EP application 15743750.0. (7 pages).
International Search Report and Written Opinion dated Aug. 14, 2017 from related PCT application PCT/US2017/031537. (12 pages).
Jiang, L. et al., Design of advanced porous grapheme materials: from grapheme nanomesh to 3D architectures. Nanoscale, Oct. 16, 2013, vol. 6, pp. 1922-1945.
JP Office Action in Japanese Application No. 2015-503405 dated Jun. 28, 2017. (English translation) (6 pages).
JP Office Action in Japanese Application No. 2015-549508 dated Jun. 27, 2017. (English translation) (7 pages).
Li, R.H. "Materials for immunoisolated cell transplantation". Adv. Drug Deliv. Rev. 33, 87-109 (1998). (23 pages).
Schweitzer, Handbook of Separation Techniques for Chemical Engineers, 1979, McGraw-Hill Book Company, pp. 2-5 to 2-8.
Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (Jan. 4, 2010), pp. 127-149.
U.S. Notice of Allowance in U.S. Appl. No. 14/193,007 dated Sep. 6, 2017. (9 pages).
U.S. Notice of Allowance in U.S. Appl. No. 14/656,580 dated Sep. 5, 2017. (8 pages).
U.S. Office Action for U.S. Appl. No. 14/609,325 dated Aug. 25, 2017. (7 pages).
U.S. Office Action for U.S. Appl. No. 15/099,193 dated Jul. 19, 2017. (13 pages).
U.S. Office Action for U.S. Appl. No. 15/289,944 dated Jul. 13, 2017. (18 pages).
U.S. Office Action for U.S. Appl. No. 15/332,982 dated Aug. 18, 2017. (9 pages).
Australian Office Action in Application No. 2013235234 dated Dec. 19, 2017 (5 pages).
Chinese Office Action in Application No. 2017-002652 dated Nov. 24, 2017 (with English translation) (7 pages).
Chu, L., et al., "Porous graphene sandwich/poly(vinylidene fluoride) composites with high dielectric properties," Composites Science and Technology, 86, (2013), pp. 70-75.
European Extended Search Report in Application No. 15743307.9 dated Nov. 15, 2017 (14 pages).
European Extended Search Report in Application No. 15755350.4 dated Oct. 30, 2017 (9 pages).
European Extended Search Report in Application No. 15762019.6 dated Nov. 20, 2017 (12 pages).
European Extended Search Report in Application No. 15762213.5 dated Oct. 10, 2017 (8 pages).
Gu et al., "One-step synthesis of porous graphene-based hydrogels containing oil droplets for drug delivery", Royal Society of Chemistry (RSC), vol. 4, No. 7, Jan. 1, 2014, pp. 3211-3218.

(56) References Cited

OTHER PUBLICATIONS

Japanese Office Action in Application No. 2015-549508 dated Nov. 7, 2017 (with English translation) (2 pages).
Kim et al., "Selective Gas Transport Through Few-Layered Graphene and Graphene Oxide Membranes", Science, vol. 342, Oct. 4, 2013, pp. 91-95 (6 total pages).
Singapore Search Report and Written Opinion in Application No. 11201609272T dated Oct. 5, 2017 (11 pages).
U.S. Notice of Allowance in U.S. Appl. No. 15/099,464 dated Nov. 16, 2017 (5 pages).
U.S. Notice of Allowance in U.S. Appl. No. 15/332,982 dated Nov. 1, 2017 (9 pages).
U.S. Office Action in U.S. Appl. No. 14/707,808 dated Nov. 6, 2017 (27 pages).
U.S. Office Action in U.S. Appl. No. 15/099,193 dated Dec. 28, 2017 (25 pages).
U.S. Office Action in U.S. Appl. No. 15/099,304 dated Nov. 24, 2017 (23 pages).
Wang, M., et al., "Interleaved Porous Laminate Composed of Reduced Graphene Oxide Sheets and Carbon Black Spacers by In-Situ Electrophoretic Deposition," The Royal Society of Chemistry (2014), pp. 1-3.
Wimalasiri, Y., et al., "Carbon nanotube/graphene composite for enhanced capacitive deionization performance," Carbon 59 (2013), pp. 464-471.
EPO Extended Search Report for European Application No. 171684883.5 dated Jul. 25, 2017 (8 pages).
EPO Supplementary Search Report for European Application No. 15762019.6 dated Aug. 9, 2017 (16 pages).
U.S. Notice of Allowance in U.S. Appl. No. 14/610,770 dated Sep. 26, 2017. (12 pages).
U.S. Notice of Allowance in U.S. Appl. No. 15/332,982 dated Sep. 21, 2017. (5 pages).
U.S. Office Action in U.S. Appl. No. 15/099,099 dated Oct. 5, 2017 (11 pages).
U.S. Office Action in U.S. Appl. No. 15/099,447 dated Oct. 3, 2017 (21 pages).
Weisen, et al., "Fabrication of nanopores in a graphene sheet with heavy ions: A molecular dynamics study", Journal of Applied Physics 114, 234304 (2013), pp. 234304-1 to 234304-6.
Notice of Allowance for U.S. Appl. No. 14/819,273 dated Oct. 28, 2016.
U.S. Office Action for U.S. Appl. No. 14/193,007 dated Oct. 21, 2016.
U.S. Office Action for U.S. Appl. No. 14/193,007 dated Dec. 21, 2015.
U.S. Office Action for U.S. Appl. No. 14/193,007 dated Jul. 1, 2016.
Extended European Search Report for Appl. Ser. No. 16833429.0 dated Aug. 9, 2019 (14 pages).
Farah et al., "Long-Term Implant Fibrosis Prevention in Rodents and Non-Human Primates Using Crystallized Drug Formulations", Nature Materials, vol. 18, Aug. 2019, pp. 892-904.
Japanese Office Action for Appl. Ser. No. 2017-511982 dated Jul. 9, 2019 (6 pages).
Raimondo et al., "Functional muscle recovery with nanoparticle-directed M2 macrophage polarization in mice", Proceedings of the National Academy of Sciences of the United States of America (PNAS), Sep. 4, 2018, pp. 1-6.
University of Massachusetts Medical School, "Fibrosis Mitigation Pathway", PowerPoint Presentation, date of presentation unknown (6 pages).
U.S. Non-Final Office Action for U.S. Appl. No. 15/589,135 dated Aug. 1, 2019 (11 pages).
U.S. Notice of Allowance for U.S. Appl. No. 14/609,325 dated Jul. 30, 2019 (7 pages).
U.S. Notice of Allowance for U.S. Appl. No. 15/410,457 dated Aug. 14, 2019 (8 pages).
Yang et al., "Large-area graphene-nanomesh/carbon-nanotube hybrid membranes for ionic and molecular nanofiltration", Science, vol. 364, Jun. 14, 2019, pp. 1057-1062 (7 pages).
Zhang et al., "Rapid and Long-Term Glycemic Regulation with a Balanced Charged Immune-Evasive Hydrogel in T1 DM Mice", Advanced Functional Materials, Advanced Science News, Jan. 30, 2019, pp. 1-9.
Zhang et al., "Rapid and Long-Term Glycemic Regulation with a Balanced Charged Immune-Evasive Hydrogel in T1 DM Mice", Advanced Functional Materials, Advanced Science News, Jan. 30, 2019, Supporting Information (13 pages).
Adiga et al., "Nanoporous Materials for Biomedical Devices," JOM 60: 26-32 (Mar. 25, 2008).
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
Apel, "Track etching technique in membrane technology," Radiation Measurements 34(1-6): 559-566 (Jun. 2001).
Bae et al., "Roll-to-roll production of 30-inch graphene films for transparent electrodes," Nature Nanotechnology 5: 574-578 (Jun. 20, 2010).
Bai et al., "Graphene nanomesh," Nature Nanotechnology 5: 190-194 (Feb. 14, 2010).
Baker. (2004). "Track-etch Membranes." In Membrane Technology and Applications (2nd ed., pp. 92-94). West Sussex, England: John Wiley & Sons.
Butler et al. "Progress, Challenges, and Opportunities in Two-Dimensional Materials Beyond Graphene", Materials Review 7(4): 2898-2926 (Mar. 6, 2013).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13 (Feb. 10, 2011).
Clochard. (undated). Radiografted track-etched polymer membranes for research and application [Scholarly project]. In Laboratoire Des Solides Irradiés. Retrieved Jun. 2, 2016, from http://iramis.cea.fr/radiolyse/5juin2015/Clochard.pdf.
Cohen-Tanugi et al, "Water Desalination across Nanoporous Graphene," ACS Nano Letters 12(7): 3602-3608 (Jun. 5, 2012).
Cohen-Tanugi, "Nanoporous graphene as a water desalination membrane," Thesis: Ph.D., Massachusetts Institute of Technology, Department of Materials Science and Engineering (Jun. 2015).
Colton, "Implantable biohybrid artificial organs," Cell Transplantation 4(4): 415-436 (Jul.-Aug. 1995).
Desai et al., "Nanoporous microsystems for islet cell replacement," Advanced Drug Delivery Reviews 56: 1661-1673 (Jul. 23, 2004).
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 58-63 (Jan. 5, 2009).
Gimi et al., "A Nanoporous, Transparent Microcontainer for Encapsulated Islet Therapy," J. Diabetes Sci. Tech. 3(2): 1-7 (Mar. 2009).
International Search Report dated Dec. 4, 2015, in related international application PCT/US2015/048205.
International Search Report dated Jun. 10, 2015, from related international application PCT/US15/20201.
Jiang et al., "Porous Graphene as the Ultimate Membrane for Gas Separation," Nano Letters 9(12): 4019-4024 (Sep. 23, 2009).
Joshi et al., "Precise and ultrafast molecular sieving through graphene oxide membranes", Science 343(6172): 752-754 (Feb. 14, 2014).
Kanani et al., "Permeability—Selectivity Analysis for Ultrafiltration: Effect of Pore Geometry," NIH-PA Author Manuscript, PMC, (Mar. 1, 2011), also published in J. Memb. Sci. 349(1-2): 405 (Mar. 1, 2010).
Karan et al., "Ultrafast Viscous Permeation of Organic Solvents Through Diamond-Like Carbon Nanosheets," Science 335: 444-447 (Jan. 27, 2012).
Kim et al., "Fabrication and Characterization of Large Area, Semiconducting Nanoperforated Graphene Materials," Nano Letters 10(4): 1125-1131 (Mar. 1, 2010).

(56) References Cited

OTHER PUBLICATIONS

Kim et al., "The structural and electrical evolution of graphene by oxygen plasma-induced disorder," Nanotechnology IOP 20(375703): 1-8 (Aug. 26, 2009).
Koski and Cui, "The New Skinny in Two-Dimensional Nanomaterials", ACS Nano 7(5): 3739-3743 (May 16, 2013).
Liu et al., "Atomically Thin Molybdenum Disulfide Nanopores with High Sensitivity for DNA Translocation," ACS Nano 8(3): 2504-2511 (Feb. 18, 2014).
Liu et al., "Graphene Oxidation: Thickness-Dependent Etching and Strong Chemical Doping," Nano Letters 8(7): 1965-1970 (Jun. 19, 2008).
Mishra et al., "Functionalized Graphene Sheets for Arsenic Removal and Desalination of Sea Water," Desalination 282: 39-45 (Nov. 1, 2011).
Morse, "Scalable Synthesis of Semiconducting Nanopatterned Graphene Materials," InterNano Resources for Nanomanufacturing (undated). Retrieved Jun. 2, 2016 from: http://www.internano.org/node/345.
Nair et al., "Unimpeded Permeation of Water Through Helium-Leak-tight Graphene-Based Membranes," Science 335: 442-444 (Jan. 27, 2012).
O'Hern et al. "Selective Molecular Transport through Intrinsic Defects in a Single Layer of CVD Graphene," ACS Nano, 6(11): 10130-10138 (Oct. 2, 2012).
O'Hern et al., "Selective Ionic Transport through Tunable Subnanometer Pores in Single-Layer Graphene Membranes," Nano Letters 14(3): 1234-1241 (Feb. 3, 2014).
Paul, "Creating New Types of Carbon-Based Membranes," Science 335: 413-414 (Jan. 27, 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sint et al., "Selective Ion Passage through Functionalized Graphene Nanopores," JACS 130: 16448-16449 (Nov. 14, 2008).
Suk et al., "Water Transport Through Ultrathin Graphene," Journal of Physical Chemistry Letters 1(10): 1590-1594 (Apr. 30, 2010).
Tan et al., "Beta-cell regeneration and differentiation: how close are we to the 'holy grail'?" J. Mol. Encodrinol. 53(3): R119-R129 (Dec. 1, 2014).
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East (Jul. 2, 2012). Retrieved Jun. 1, 2016 from: natureasia.com/en/nmiddleeast/article/10.1038/nmiddleeast.2012.92?WT.mc_id=F Bk NatureMEast].
Wikipedia, "Ion track." Jun. 1, 2016. Retrieved Jun. 1, 2016 from: en.wikipedia.org/wiki/ion_track.
Xu et al., "Graphene-like Two-Dimensional Materials", Chemical Reviews 113: 3766-3798 (Jan. 3, 2013).
Zan et al., "Graphene Reknits Its Holes," Nano Lett. 12(8): 3936-3940 (Jul. 5, 2012).
Zhao et al. "Two-Dimensional Material Membranes: An Emerging Platform for Controllable Mass Transport Applications," Small 10(22): 4521-4542 (Sep. 10, 2014).
Dong et al., "Growth of large-sized graphene thin-films by liquid precursor-based chemical vapor deposition under atmospheric pressure," Carbon 49(11): 3672-3678 (May 2011).
Hong et al., "Graphene multilayers as gates for multi-week sequential release of proteins from surfaces," NIH-PA Author Manuscript PMC (Jun. 1, 2014), also published in ACS Nano, Jan. 24, 2012; 6(1): 81-88 (first published online Dec. 29, 2011).
Hu et al., "Enabling graphene oxide nanosheets as water separation membranes," Environmental Science & Technology, 47(8): 3715-3723 (Mar. 14, 2013).
International Search Report and Written Opinion of the International Searching Authority dated Jul. 22, 2016, from related international patent application PCT/US2016/027607.
International Search Report and Written Opinion of the International Searching Authority dated Jul. 22, 2016, from related international patent application PCT/US2016/027616.
International Search Report and Written Opinion of the International Searching Authority dated Jul. 22, 2016, from related PCT application PCT/US2016/027596.
International Search Report and Written Opinion of the International Searching Authority dated Jul. 22, 2016, from related PCT application PCT/US2016/027603.
International Search Report and Written Opinion of the International Searching Authority dated Jul. 22, 2016, from related PCT application PCT/US2016/027610.
International Search Report and Written Opinion of the International Searching Authority dated Jul. 22, 2016, from related PCT application PCT/US2016/027612.
International Search Report and Written Opinion of the International Searching Authority dated Jun. 22, 2016, from related PCT application PCT/US2016/027637.
Kurapati et al., "Graphene oxide based multilayer capsules with unique permeability properties: facile encapsulation of multiple drugs," Chemical Communication 48: 6013-6015 (Apr. 25, 2012).
Li et al., "3D graphene oxide-polymer hydrogel: near-infrared light-triggered active scaffold for reversible cell capture and on-demand release," Advanced Materials 25: 6737-6743 (Oct. 7, 2013).
Marquardt et al., "Hybrid materials of platinum nanoparticles and thiol-functionalized graphene derivatives," Carbon 66: 285-294 (Jan. 2014; first published online Sep. 12, 2013).
Nam et al., "Monodispersed PtCo nanoparticles on hexadecyltrimethylammonium bromide treated graphene as an effective oxygen reduction reaction catalyst for proton exchange membrane fuel cells," Carbon 50: 3739-3747 (Aug. 2012; first published online Apr. 5, 2012).
Nandamuri et al., "Chemical vapor deposition of graphene films," Nanotechnology 21(14): 1-4 (Mar. 10, 2010).
Nayini et al., "Synthesis and characterization of functionalized carbon nanotubes with different wetting behaviors and their influence on the wetting properties of carbon nanotubes/polymethylmethacrylate coatings," Progress in Organic Coatings 77(6): 1007-1014 (Mar. 2014).
Sun et al., "Growth of graphene from solid carbon sources," Nature 468(7323): 549-552 (Nov. 25, 2010; including corrigendum in Nature 471(7336): 124 (Mar. 2011).
Tang et al., "Highly wrinkled cross-linked graphene oxide membranes for biological and charge-storage applications," Small 8(3): 423-431 (Feb. 6, 2012; first published online Dec. 13, 2011).
Allen et al., "Craters on silicon surfaces created by gas cluster ion impacts," Journal of Applied Physics, 92(7): 3671-3678 (Oct. 2002).
Atmeh et al., "Albumin Aggregates: Hydrodynamic Shape and Physico-Chemical Properties," Jordan Journal of Chemistry, 2(2): 169-182 (2007).
Chen et al., "Mechanically Strong, Electrically Conductive, and Biocompatible Graphene Paper," Adv. Mater., 20(18): 3557-3561 (Sep. 2008) (available online Jul. 2008).
CN Office Action in Chinese Application No. 201380013988.9 dated Aug. 18, 2016 (English translation not readily available).
Fuertes, "Carbon composite membranes from Matrimid® and Kapton® polyimides for gas separation," Microporous and Mesoporous Materials, 33: 115-125 (1991).
Galashev, "Computer study of the removal of Cu from the graphene surface using Ar clusters," Computational Materials Science, 98: 123-128 (Feb. 2015) (available online Nov. 2014).
International Search Report and Written Opinion in PCT/US2015/013599 dated Jul. 20, 2015.
International Search Report and Written Opinion in PCT/US2015/013805 dated Apr. 30, 2015.
International Search Report and Written Opinion in PCT/US2015/018114 dated Jun. 3, 2015.
International Search Report and Written Opinion in PCT/US2015/020246 dated Jun. 10, 2015.
International Search Report and Written Opinion in PCT/US2015/020296 dated Jun. 17, 2015.

(56) References Cited

OTHER PUBLICATIONS

International Search Report and Written Opinion in PCT/US2015/028948 dated Jul. 16, 2015.
International Search Report and Written Opinion in PCT/US2015/029932 dated Oct. 6, 2015.
Inui et al., "Molecular dynamics simulations of nanopore processing in a graphene sheet by using gas cluster ion beam," Appl. Phys. A, 98: 787-794 (Mar. 2010) (available online Dec. 2009).
Koh et al., "Sensitive NMR Sensors Detect Antibodies to Influenza," NIH PA Author Manuscript PMC (Apr. 2009), also published in Angew. Chem. Int'l. Engl, 47(22): 4119-4121 (May 2008) (available online Apr. 2008).
Lehtinen et al., "Cutting and controlled modification of graphene with ion beams," Nanotechnology, 22: 175306 (8 pages) (Mar. 2011).
Matteucci et al., "Transport of gases and Vapors in Glass and Rubbery Polymers," in Materials Science of Membranes for Gas and Vapor Separation. (Yampolskii et al., eds. 2006) (available online Jun. 2006).
O'Hern et al., "Development of process to transfer large areas of LPCVD graphene from copper foil to a porous support substrate," 1-62 (M.S. Thesis, Massachusetts Institute of Technology, Thesis) (Sep. 2011).
Plant et al. "Size-dependent propagation of Au nanoclusters through few-layer graphene," Nanoscale, 6: 1258-1263 (2014) (available online Oct. 2013).
Popok. "Cluster Ion Implantation in Graphite and Diamond: Radiation Damage and Stopping of Cluster Constituents," Reviews on Advanced Materials Science, 38(1): 7-16 (2014).
Russo et al., "Atom-by-atom nucleation and growth of graphene nanopores," PNAS 109(16): 5953-5957 (Apr. 2012).
U.S. Notice of Allowance in U.S. Appl. No. 14/610,770 dated Aug. 12, 2016.
U.S. Office Action in U.S. Appl. No. 14/656,190 dated Aug. 29, 2016.
U.S. Office Action for U.S. Appl. No. 14/656,580 dated Jun. 2, 2016.
U.S. Office Action in U.S. Appl. No. 14/819,273 dated Jul. 6, 2016.
U.S. Office Action for U.S. Appl. No. 14/856,198 dated Jun. 3, 2016.
Yoon, "Simulations show how to turn graphene's defects into assets," ScienceDaily (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: (Jan. 2015) (available online Nov. 2014).
Zhang et al. Modern Thin-Film Technology 284-285 (Metallurgical Industry Press, 1st ed. 2009) (English translation not readily available).
Zhao et al. (2012), "Effect of SiO2 substrate on the irradiation-assisted manipulation of supported graphene: a molecular dynamics study," Nanotechnology 23(28): 285703 (Jul. 2012) (available online Jun. 2012).
Zhao et al. (May 2012), "Drilling Nanopores in Graphene with Clusters: A Molecular Dynamics Study," J. Phys. Chem. C, 116(21): 11776-11178 (2012) (available online May 2012).
International Preliminary Report on Patentability for PCT/US2015/013599 dated Aug. 2, 2016.
International Preliminary Report on Patentability for PCT/US2015/013805 dated Aug. 2, 2016.
International Preliminary Report on Patentability for PCT/US2015/018114 dated Sep. 6, 2016.
International Preliminary Report on Patentability for PCT/US2015/020201 dated Sep. 13, 2016.
International Preliminary Report on Patentability for PCT/US2015/020246 dated Sep. 13, 2016.
International Preliminary Report on Patentability for PCT/US2015/020296 dated Sep. 22, 2016.
U.S. Notice of Allowance in U.S. Appl. No. 14/610,770 dated Jan. 23, 2017.
U.S. Notice of Allowance in U.S. Appl. No. 14/856,198 dated Feb. 10, 2017.
U.S. Notice of Allowance in U.S. Appl. No. 14/856,198 dated Mar. 1, 2017.
U.S. Office Action in U.S. Appl. No. 14/609,325 dated Feb. 16, 2017.
U.S. Office Action in U.S. Appl. No. 14/193,007 dated Mar. 23, 2017.
U.S. Office Action in U.S. Appl. No. 14/656,580 dated Feb. 9, 2017.
U.S. Office Action in U.S. Appl. No. 14/843,944 dated Jan. 6, 2017.
U.S. Office Action in U.S. Appl. No. 15/099,464 dated Mar. 10, 2017.
Chen et al., "Hierarchically porous graphene-based hybrid electrodes with excellent electrochemical performance", Journal of Materials Chemistry A: Materials for Energy and Sustainability, vol. 1, No. 33, Jan. 1, 2013, pp. 9409-9413.
Chinese Office Action in Application No. 201580006829.5 dated Jan. 23, 2018 (with English translation) (13 pages).
European Extended Search Report in Application No. 15786691.4 dated Dec. 1, 2017 (10 pages).
European Extended Search Report in Application No. 15789852.9 dated Dec. 6, 2017 (8 pages).
Japanese Office Action in Application No. 2017-042023 dated Jan. 9, 2018 (with English translation) (9 pages).
Singapore Search Report and Written Opinion in Application No. 11201701654U dated Dec. 6, 2017 (6 pages).
Taiwanese Office Action in Application No. 102146079 dated Dec. 12, 2017 (with English translation) (4 pages).
U.S. Notice of Allowance in U.S. Appl. No. 14/843,944 dated Feb. 9, 2018 (9 pages).
U.S. Office Action for U.S. Appl. No. 15/099,482 dated Feb. 23, 2018 (9 pages).
U.S. Office Action in U.S. Appl. No. 14/609,325 dated Jan. 16, 2018 (11 pages).
U.S. Office Action in U.S. Appl. No. 14/656,190 dated Jan. 10, 2018 (14 pages).
U.S. Office Action in U.S. Appl. No. 14/856,471 dated Jan. 11, 2018 (36 pages).
U.S. Office Action in U.S. Appl. No. 15/099,099 dated Feb. 15, 2018 (13 pages).
Wang et al., "Preparation of high-surface-area carbon nanoparticle/graphene composites", Carbon, Elsevier, Oxford, GB, vol. 50, No. 10, Apr. 8, 2012, pp. 3845-3853.
Office Action for Indian Appl. Ser. No. 1566/DELNP/2013 dated Feb. 2, 2018 (7 pages).
Office Action for Japanese Appl. Ser. No. 2016-521448 dated Mar. 16, 2018 (5 pages).
Skrzypek et al., "Pancreatic islet macroencapsulation using microwell porous membranes", Scientific Reports, 7: 9186 | DOI:10.1038/s41598-017-09647-7, Aug. 23, 2017 (12 pages).
U.S. Notice of Allowance for U.S. Appl. No. 15/099,464 dated Feb. 28, 2018 (5 pages).
U.S. Office Action for U.S. Appl. No. 15/099,276 dated Mar. 22, 2018 (13 pages).
U.S. Office Action for U.S. Appl. No. 15/453,441 dated Mar. 22, 2018 (7 pages).
European Extended Search Report in Application No. 15837617.8 dated Mar. 22, 2018 (9 pages).
Singapore Written Opinion for Appl. Ser. No. 11201607584P dated Jun. 8, 2018 (7 pages).
U.S. Non-Final Office Action for U.S. Appl. No. 15/099,410 dated Jun. 13, 2018 (15 pages).
U.S. Notice of Allowance for U.S. Appl. No. 15/453,441 dated Jun. 12, 2018 (8 pages).
U.S. Office Action for U.S. Appl. No. 15/099,056 dated May 29, 2018 (33 pages).
U.S. Office Action for U.S. Appl. No. 15/099,289 dated Jun. 7, 2018 (16 pages).

(56) References Cited

OTHER PUBLICATIONS

Bose et al.,"Microfabricated immune-isolating devices for transplanting therapeutic cells in vivo", Koch Institute of Integrative Cancer Research, Massachusetts Institute of Technology, Undated (1 page).
Indian Office Action for Appl. Ser. No. 7731/DELNP/2014 dated Jul. 26, 2018 (6 pages).
Japanese Office Action for Appl. Ser. No. 2017-002652 dated Jul. 3, 2018 (8 pages).
Linnert, "Welding Metallurgy—Carbon and Alloy Steels", vol. I—Fundamentals (4th Edition), Chapter 2—The Structure of Metals, GML Publications, American Welding Society (AWS), Year: 1994, pp. 17-74. Retrieved from app.knovel.com/hotlink/pdf/id:kt0095RCL3/welding-metallurgy-carbon/structure-metals.
U.S. Final Office Action for U.S. Appl. No. 14/707,808 dated Jun. 27, 2018 (28 pages).
U.S. Final Office Action for U.S. Appl. No. 15/099,482 dated Aug. 27, 2018 (10 pages).
U.S. Non-Final Office Action for U.S. Appl. No. 15/099,239 dated Jul. 12, 2018 (31 pages).
U.S. Non-Final Office Action for U.S. Appl. No. 15/099,304 dated Aug. 27, 2018 (22 pages).
U.S. Notice of Allowance for U.S. Appl. No. 15/099,420 dated Aug. 8, 2018 (8 pages).
Vatanpour et al., "Fabrication and characterization of novel antifouling nanofiltration membrane prepared from oxidized multiwalled carbon nanotube/polyethersulfone nanocomposite", Journal of Membrane Science, vol. 375, Elsevier, Apr. 6, 2011, pp. 284-294.
Zhang et al., "Synergetic effects of oxidized carbon nanotubes and graphene oxide on fouling control and anti-fouling mechanism of polyvinylidene fluoride ultrafiltration membranes", Journal of Membrane Science, vol. 448, Elsevier, Aug. 7, 2013, pp. 81-92.
U.S. Final Office Action for U.S. Appl. No. 14/609,325 dated Sep. 12, 2018 (8 pages).
U.S. Final Office Action for U.S. Appl. No. 15/099,289 dated Oct. 15, 2018 (14 pages).
U.S. Non-Final Office Action for U.S. Appl. No. 14/656,657 dated Oct. 10, 2018 (6 pages).
U.S. Non-Final Office Action for U.S. Appl. No. 14/707,808 dated Nov. 15, 2018 (34 pages).
U.S. Non-Final Office Action for U.S. Appl. No. 15/099,099 dated Sep. 27, 2018 (13 pages).
U.S. Non-Final Office Action for U.S. Appl. No. 15/099,269 dated Oct. 5, 2018 (11 pages).
U.S. Non-Final Office Action for U.S. Appl. No. 15/099,276 dated Nov. 1, 2018 (13 pages).
U.S. Notice of Allowance for U.S. Appl. No. 15/099,056 dated Nov. 16, 2018 (8 pages).
Canadian Office Action for Appl. Ser. No. 2,865,648 dated Jan. 16, 2019 (4 pages).
EPO Office Action for Appl. Ser. No. 13714806.0 dated Dec. 5, 2018 (6 pages).
EPO Office Action for Appl. Ser. No. 15786691.4 dated Dec. 5, 2018 (6 pages).
Extented European Search Report for Appl. Ser. No. 16833431.6 dated Feb. 25, 2019 (16 pages).
Koenig et al., "Selective Molecular Sieving Through Porous Graphene", Nature Nanotechnology, vol. 7, No. 11, pp. 728-732 (Including Supplementary Informaton) (23 pages).
U.S. Advisory Action for U.S. Appl. No. 15/099,289 dated Jan. 8, 2019 (6 pages).
U.S. Final Office Action for U.S. Appl. No. 14/686,452 dated Dec. 13, 2018 (6 pages).
U.S. Final Office Action for U.S. Appl. No. 15/099,099 dated Jan. 2, 2019 (13 pages).
U.S. Final Office Action for U.S. Appl. No. 15/099,239 dated Feb. 21, 2019 (26 pages).
U.S. Non-Final Office Action for U.S. Appl. No. 14/609,325 dated Jan. 14, 2019 (7 pages).
U.S. Non-Final Office Action for U.S. Appl. No. 15/099,482 dated Jan. 31, 2019 (13 pages).
U.S. Notice of Allowance for U.S. Appl. No. 15/099,289 dated Jan. 18, 2019 (7 pages).
U.S. Notice of Allowance for U.S. Appl. No. 15/099,410 dated Jan. 3, 2019 (9 pages).
Anasori et al., "2D metal carbides and nitrides (MXenes) for energy storage", Nature Reviews, vol. 2, Article No. 16098, Jan. 17, 2017, pp. 1-17.
Australian Office Action for Appl. Ser. No. 2018200090 dated Apr. 30, 2019 (4 pages).
Huang et al., "Ultrathin Carbon Molecular Sieve Films and Room-Temperature Oxygen Functionalization for Gas-Sieving", ACS Applied Maters & Interfaces 2019, vol. 11, Apr. 16, 2019, pp. 16729-16736.
Japanese Office Action for Appl. Ser. No. 2016-566751 dated Jun. 7, 2019 (8 pages) .
Mojtabavi et al., "Single-Molecule Sensing Using Nanopores in Two-Dimensional Transition Metal Carbide (MXene) Membranes", American Chemical Society, ACS Nano 2019, vol. 13, Mar. 7, 2019, pp. 3042-3053.
Neumann et al., "Bottom-Up Synthesis of Graphene Monolayers with Tunable Crystallinity and Porosity", American Chemical Society, ACS Nano, May 21, 2019, pp. A-M (13 pages).
Pang et al., "Applications of 2D MXenes in energy conversion and storage systems", Chemical Society Review, 2019, vol. 48, No. 1, Jun. 25, 2018, pp. 72-133.
U.S. Advisory Action for U.S. Appl. No. 15/099,239 dated Jun. 1, 2019 (7 pages).
U.S. Final Office Action for U.S. Appl. No. 14/707,808 dated Jun. 26, 2019 (37 pages).
U.S. Non-Final Office Action for U.S. Appl. No. 15/308,351 dated Jun. 30, 2019 (9 pages).
U.S. Notice of Allowance for U.S. Appl. No. 15/099,269 dated Jun. 6, 2019 (8 pages).
Apel et al. "Effect of nanosized surfactant molecules on the etching or ion tracks: New degrees or freedom in design of pore shape", Nuclear Instruments and Methods in Physics Research Section B: Beam Interactions with Materials and Atoms, vol. 209, Aug. 2003, pp. 329-344.
Australian Office Action for Appl. Ser. No. 2015252784 dated Mar. 25, 2019 (11 pages).
Australian Office Action for Appl. Ser. No. 2015255756 dated Feb. 22, 2019 (5 pages).
Extended European Search Report for Appl. Ser. No. 16833430.8 dated Apr. 25, 2019 (11 pages).
Extended European Search Report for Appl. Ser. No. 16833432.4 dated Apr. 16, 2019 (14 pages).
Extended European Search Report for Appl. Ser. No. 16833433.2 dated Mar. 4, 2019 (15 pages).
International Search Report and Written Opinion for PCT Appl. Ser. No. PCT/US2018/065514 (16 pages).
Japanese Office Action for Appl. Ser. No. 2016-565216 dated Feb. 26, 2019 (7 pages).
Kim et al., "High quality reduced graphene oxide through repairing with multi-layered graphene ball nanostructures", Scientific Reports, vol. 3, No. 1, Nov. 19, 2013, pp. 1-6.
Singapore Written Opinion for Appl. Ser. No. 11201800845X dated Feb. 26, 2019 (8 pages).
Singapore Written Opinion for Appl. Ser. No. 11201800883R dated Feb. 22, 2019 (7 pages).
Singapore Written Opinion for Appl. Ser. No. 11201800968Q dated Feb. 19, 2019 (6 pages).
U.S. Final Office Action for U.S. Appl. No. 15/099,269 dated Apr. 18, 2019 (7 pages).
U.S. Final Office Action for U.S. Appl. No. 15/099,304 dated Apr. 19, 2019 (27 pages).
U.S. Non-Final Office Action for U.S. Appl. No. 14/656,657 dated Mar. 28, 2019 (9 pages).
U.S. Non-Final Office Action for U.S. Appl. No. 14/686,452 dated May 3, 2019 (7 pages).
U.S. Non-Final Office Action for U.S. Appl. No. 15/099,193 dated May 2, 2019 (19 pages).

(56) References Cited

OTHER PUBLICATIONS

U.S. Non-Final Office Action for U.S. Appl. No. 15/410,457 dated Feb. 28, 2019 (13 pages).

* cited by examiner

TWO-DIMENSIONAL MATERIALS AND USES THEREOF

CROSS-REFERENCE TO RELATED PATENT APPLICATION

This application is a continuation-in-part of U.S. application Ser. No. 14/610,770, filed Jan. 30, 2015, which claims the benefit of U.S. Provisional Application No. 61/934,530, filed Jan. 31, 2014, each of which is incorporated by reference herein in its entirety. This application is also a continuation-in-part of U.S. application Ser. No. 14/843,944, filed Sep. 2, 2015, which claims the benefit of U.S. Provisional Application No. 62/044,877, filed on Sep. 2, 2014, each of which is incorporated by reference herein in its entirety. This application is also a continuation-in-part of U.S. application Ser. No. 15/099,295, filed on Apr. 14, 2016, which is incorporated by reference herein in its entirety. This application is also a continuation-in-part of U.S. application Ser. No. 15/099,482, filed on Apr. 14, 2016, which is incorporated by reference herein in its entirety.

This application is a continuation-in-part related to and claims the benefit of U.S. application Ser. No. 14/856,198, filed Sep. 16, 2015, which is a continuation-in-part of U.S. application Ser. No. 14/656,580, filed Mar. 12, 2015, which claims the benefit of U.S. Provisional Application No. 61/951,930, filed Mar. 12, 2014, each of which are incorporated by reference herein in its entirety. This application is a continuation-in-part of U.S. application Ser. No. 14/656,657, filed Mar. 12, 2015, which claims the benefit of U.S. Provisional Application No. 61/951,660, filed Mar. 12, 2014, which are incorporated by reference herein in their entirety. This application is a continuation-in-part of U.S. application Ser. No. 14/754,531, filed Jun. 29, 2015, which is a continuation-in-part of U.S. application Ser. No. 13/480,569, filed May 25, 2012, now U.S. Pat. No. 9,067,811, which are incorporated by reference herein in their entirety. This application is a continuation-in-part of U.S. application Ser. No. 14/609,325, filed Jan. 29, 2015, which claims the benefit of U.S. Provisional Application No. 61/934,537, filed Jan. 31, 2014, which are incorporated by reference herein in their entirety. This application is a continuation-in-part of U.S. application Ser. No. 14/656,190, filed Mar. 12, 2015, which claims the benefit of U.S. Provisional Application No. 61/951,926, filed Mar. 12, 2014, which are incorporated by reference herein in their entirety. This application is a continuation-in-part of U.S. application Ser. No. 14/656,580, filed Mar. 12, 2015, which claims the benefit of U.S. Provisional Application 61/951,930, filed Mar. 12, 2014, which are incorporated herein by reference in their entirety. This application is a continuation-in-part related to and claims the benefit of U.S. application Ser. No. 14/856,471, filed Sep. 16, 2015, which is a continuation-in-part of U.S. application Ser. No. 14/656,190, filed Mar. 12, 2015, which claims the benefit of U.S. Provisional Application No. 61/951,926, filed Mar. 12, 2014, which are incorporated by reference herein in their entirety. This application is a continuation-in-part of U.S. application Ser. No. 14/707,808, filed May 8, 2015, which claims the benefit of U.S. Provisional Application No. 61/990,561, filed May 8, 2014 and U.S. Provisional Application No. 61/990,204, filed May 8, 2014, which are incorporated by reference herein in their entirety. This application is a continuation-in-part of PCT Application No. PCT/US15/28948, filed May 1, 2015, which claims the benefit of U.S. Provisional Application No. 61/987,410, filed May 1, 2014; and which is a continuation of PCT/US15/18114, filed Feb. 27, 2015, which claims priority to U.S. patent application Ser. No. 14/193,007, filed Feb. 28, 2014, which are incorporated by reference herein in their entirety. This application is a continuation-in-part of U.S. application Ser. No. 14/819,273, filed Aug. 5, 2015, which claims the benefit of U.S. Provisional Application No. 62/039,856, filed Aug. 20, 2014, and which is a continuation-in-part of U.S. application Ser. No. 14/610,770, filed Jan. 30, 2015, which claims the benefit of U.S. Provisional Application No. 61/934,530, filed Jan. 31, 2014, which are incorporated by reference herein in their entirety. This application is related to and claims the benefit of U.S. Provisional Application No. 62/313,581, filed Mar. 25, 2016, which is incorporated by reference herein in its entirety.

This application a continuation-in-part of U.S. application Ser. No. 15/099,304, filed Apr. 14, 2016, which is incorporated by reference herein in its entirety. This application is a continuation-in-part of U.S. application Ser. No. 15/099,410, filed Apr. 14, 2016, which is incorporated by reference herein in its entirety. This application is a continuation-in-part of U.S. application Ser. No. 15/099,420, filed Apr. 14, 2016, which is incorporated by reference herein in its entirety. This application is a continuation-in-part of U.S. application Ser. No. 15/099,289, filed Apr. 14, 2016, which is incorporated by reference herein in its entirety. This application is a continuation-in-part of U.S. application Ser. No. 15/099,276, filed Apr. 14, 2016, which claims the benefit of U.S. Provisional Application No. 62/202,056, filed Aug. 6, 2015, which are incorporated by reference herein in their entirety. This application is a continuation-in-part of U.S. application Ser. No. 15/099,447, filed Apr. 14, 2016, which is incorporated by reference herein in its entirety. This application is a continuation-in-part of U.S. application Ser. No. 15/099,269, filed Apr. 14, 2016, which claims the benefit of U.S. Provisional Application No. 62/201,539, filed Aug. 5, 2015, and U.S. Provisional Application No. 62/201,527, filed Aug. 5, 2015, which are incorporated by reference herein in their entirety. This application is a continuation-in-part of U.S. application Ser. No. 15/099,099, filed Apr. 14, 2016, which claims the benefit of U.S. Provisional Application No. 62/202,122, filed Aug. 6, 2015, which are incorporated by reference herein in their entirety. This application is a continuation-in-part of U.S. application Ser. No. 15/099,056, filed Apr. 14, 2016, which is incorporated by reference herein in its entirety. This application is a continuation-in-part of U.S. application Ser. No. 15/099,464, filed Apr. 14, 2016, which is incorporated by reference herein in its entirety. This application is a continuation-in-part of U.S. application Ser. No. 15/099,239, filed Apr. 14, 2016, which claims the benefit of U.S. Provisional Application No. 62/201,527, filed Aug. 5, 2015, and U.S. Provisional Application No. 62/201,539, filed Aug. 5, 2015, which are incorporated by reference herein in their entirety. This application is a continuation-in-part of U.S. application Ser. No. 15/099,193, filed Apr. 14, 2016, which claims the benefit of U.S. Provisional Application No. 62/202,056, filed Aug. 6, 2015, which are incorporated by reference herein in their entirety.

FIELD

The present embodiments generally relates to two-dimensional materials, such as graphene as well as graphene platelet-based polymers, and methods of use and production thereof.

BACKGROUND

Graphene represents a form of carbon in which the carbon atoms reside within a single atomically thin sheet or a few layered sheets (e.g., about 20 or less) of fused six-membered rings forming an extended planar lattice. In its various forms, graphene has garnered widespread interest for use in a number of applications, primarily due to its favorable combination of high electrical and thermal conductivity values, good in-plane mechanical strength, and unique optical and electronic properties. In many aspects, the properties of graphene parallel those of carbon nanotubes, since both nanomaterials are based upon an extended $sp^2$-hybridized carbon framework. Other two-dimensional materials having a thickness of a few nanometers or less and an extended planar lattice are also of interest for various applications.

Two-dimensional graphene materials such as perforated graphene have been demonstrated as effective in filtration devices. However, the synthesis of these compositions may be costly or time consuming. Thus, there is a need for cheaper, more easily made compositions that can provide similar effects as graphene compositions, as well as new effects.

SUMMARY

Some embodiments include a process comprising:

exposing a multilayered material to ions provided by an ion source, the multilayered material comprising a first layer comprising a two-dimensional first material and a second layer of a second material in contact with the first layer, the ions being provided with an ion energy ranging from 1.0 keV to 10 keV, and a flux from 0.1 nA/mm$^2$ to 100 nA/mm$^2$; and producing a perforated two-dimensional material by producing a plurality of holes in the two-dimensional first material by interacting a plurality of ions provided by the ion source, neutralized ions or a combination thereof with the two-dimensional first material and with the second material.

introducing one or more occluding moieties at least partially into the at least one uncovered pore to occlude the at least one uncovered pore;

introducing a composite membrane comprising a porous substrate having a plurality of pores and a sheet of the perforated two-dimensional material disposed on a surface of the porous substrate and defining a top surface of the membrane, wherein the sheet of two-dimensional material covers at least a portion of the pores of the substrate and wherein at least one pore of the substrate is not covered by the two-dimensional material;

incorporating the perforated two-dimensional material into a blood filtration device that comprises two or more membranes which each comprise the perforated two-dimensional material, and further comprises a membrane a membrane comprising a cross-linked graphene platelet polymer comprising a plurality of cross-linked graphene platelets comprising a graphene portion and a cross-linking portion, the cross-linking portion contains a 4 to 10 atom link, and the cross-linked graphene platelet polymer being produced by reaction of an epoxide functionalized graphene platelet and a (meth)acrylate or (meth)acrylamide functionalized cross-linker;

exposing blood from a patient to the blood filtration device having a hemodialysis membrane comprising the perforated two-dimensional material, the two-dimensional first material being disposed upon a porous support structure;

removing a contaminant from the blood with the hemodialysis membrane; and recirculating purified blood to the patient.

In some embodiments, the perforated two-dimensional material is graphene-based material. In some embodiments, graphene-based material is single-layer graphene. In some embodiments, the perforated two-dimensional material is graphene oxide. In some embodiments, the one or more occluding moieties are particles sized for at least partial introduction into an uncovered pore, but which cannot exit the uncovered pore. In some embodiments, the particles are deformable or swellable. In some embodiments, the particles are deformable and pressure or energy is applied to the particles after they are introduced into the at least one uncovered pore. In some embodiments, heat or light of a selected wavelength is applied to the particles after they are introduced into the at least one uncovered pore. In some embodiments, an electron or ion beam is applied to the particles after they are introduced into the at least one uncovered pore.

Some embodiments describe methods for at least partially occluding flow of liquid and/or chemical species and/or particles through apertures within sheets of graphene-based materials or other two-dimensional materials. Some embodiments also describe related methods for occluding pores in a composite membrane to generate membranes where flow through the pores is mediated through size-selected perforated graphene or other two-dimensional materials.

In one aspect, the methods involve reacting an occluding moiety with defects or apertures in sheets of graphene-based materials or other two dimensional materials or catalyzing a reaction in such defects or apertures to mitigate the defect or aperture, where mitigation includes closing or healing of the defect or aperture or decreasing the size of the defect or aperture. In healing the graphene-based material, perforations in the graphene-based material may or may not be healed. Fluorescently tagged moieties may be used to verify healing or failure of healing. In an embodiment, reacting or catalyzing a reaction is directed to defects or aperture having a certain size, geometry or functionality. The methods can involve flowing a chemical moiety through the perforations in a sheet of the two-dimensional material such that only the moiety passing through the sheet of the two-dimensional material is available to react or catalyze a reaction with the defect or aperture, i.e., with chemical moieties at the defect or aperture. By choosing the occlusion technique and the occluding moiety, larger apertures in a sheet of a two-dimensional material can become occluded, for example, in preference to smaller apertures, producing a sheet of two dimensional material with improved flow selectivity. In some cases it can be desirable to occlude substantially all the apertures in a sheet of a two-dimensional material, such that the treated sheet of two-dimensional material is substantially impervious to flow of fluids or chemical species there through. The sheets of a two-dimensional material having at least partially occluded apertures prepared according to the embodiments described herein can be used in separation techniques and systems, although they are also usable in other applications, such as selective barrier applications. In an embodiment, sheets of two-dimensional material having at least partially occluded apertures and particularly sheets where the majority (greater than about 50%) of the apertures or wherein substantially all of the apertures are occluded can be used as starting material for preparation of size-selective perforated graphene or other two-dimensional material, wherein perforations of a selected size range are introduced into the sheets in which apertures have been occluded.

In some embodiments, perforated graphene-based material having at least a portion of its apertures occluded with a chemical moiety is described herein.

In another aspect, some embodiments relate to methods of making composite membranes in which a sheet of graphene-based material or other two-dimensional material is disposed on a surface of a porous substrate wherein at least a portion of the pores of the substrate are covered by the sheet of two-dimensional material and in which pores in the substrate, that are not covered or are only partially covered, are occluded with one or more occluding moieties such that fluid or other chemical moieties cannot pass through the occluded pores. The size of the moiety provides a selectivity for which size of pores will be occluded. The methods herein in certain embodiments ensure that pores in the composite membrane that are covered by the two-dimensional material are not occluded which results in composite membranes with minimal reduction in membrane function. Composite membranes with occluded pores include those in which a portion of the uncovered substrate pores are occluded, those in which a majority (50% or more) of the uncovered substrate pores are occluded and those in which substantially all (95% or more) of the uncovered pores are occluded. The two-dimensional material covering the pores may be defect and aperture-free, or may be size-selective perforated. In an embodiment, the two-dimensional material of the composite membrane is perforated after treatment to occlude pores that are not covered by the two-dimensional material. Size-selective perforation after pore occlusion provides composite membranes useful for size-selective filtration. Composite membranes in which uncovered pores are occluded are useful, for example, as starting materials for preparation of size-selective filtration membranes.

Some embodiments also relate to composite membranes prepared by the methods herein wherein at least a portion of the uncovered pores of the substrate are occluded.

In an embodiment, the method of occluding uncovered pores includes introducing an occluding moiety into an uncovered pore. In an embodiment, the occluding moiety is one or more particles sized for at least partial entrance into the uncovered pore, but which do not pass through the pore. In an embodiment, the one or more particles are deformable after introduction into the pore by application of energy, for example, application of pressure, heat, light, particularly light of selected wavelength, or an ion or particle beam. In an embodiment, the one or more particles carry one or more chemical reactive groups which react or can be activated to react with compatible reactive groups in the pores, on the surface of the substrate or on other particles to facilitate anchoring of the one or more particles to occlude a pore.

In an embodiment, the occluding particles are swellable after entry into a pore. For example, the material from which the particle is made is selected such that it swells when contacted by material which is absorbed into the particle. In an embodiment, the particle is swellable on contact with a selected absorbable fluid. In an embodiment, the absorbable fluid is water or an aqueous solution. In an embodiment, the absorbable fluid is an organic solvent. In an embodiment, the absorbable fluid is a polar organic solvent. In an embodiment, the absorbable fluid is a non-polar organic solvent. In an embodiment, the occluding particles are hydrogel particles which swell on absorption of water. In an embodiment, the occluding particles are polymer particles which swell on adsorption of an organic solvent, such as cross linked organic thermoset polymers, for example.

In an embodiment, the one or more occluding particles are monodisperse with respect to particle size. In an embodiment, the one or more occluding particles have a selected range of particles sizes. In an embodiment, after initial occlusion of a pore by one or more particles of a given first size, additional secondary particles of a size less than that of the initial particles can optionally be introduced into a pore to further facilitate occlusion of the pore or to facilitate anchoring. In this embodiment, the first and secondary particles optionally carry reactive groups to facilitate reaction with compatible reactive groups on the surface of pores or on other particles. In this embodiment, after particle introduction, energy is optionally applied, for example, in the form of heat, light or ion beam irradiation to facilitate anchoring in the pores. The use of particles of different sizes can result in higher packing densities which can provide better occlusion of pores. Particle compositions can, for example, be employed for occlusion, which have bimodal or trimodal particle size distributions.

In an embodiment, the pore occluding moiety is one or more monomers or oligomers which are introduced into an uncovered pore and polymerized therein to form a polymer and occlude the pore. Polymerization may be activated by any known means that is not detrimental to the two-dimensional material or to the substrate, including for example, activation by heating to a selected temperature, irradiation with light of selected wavelength, and/or introduction of a polymerization catalyst, or other methods (see, for example, US patent application filed herewith, entitled SELECTIVE INTERFACIAL MITIGATION OF GRAPHENE DEFECTS, 15/099,410, incorporated herein in its entirety) In some embodiments, a polymerization catalyst may be activated by application of heat, light or other form of energy.

In an embodiment, the pores of the substrate can be shaped along their length to facilitate occlusion by one or more particles. For example, the pores may be tapered where the size of the opening into a pore (e.g., the pore diameter) is larger than the size of the exit from the pore. In an embodiment, the pores of the substrate can be shaped at one or both pore openings (entrance or exit openings) to facilitate occlusion by one or more particles. Substrate pores may be shaped to have a desired geometry, e.g., circular, oval, rectangular, slit, square mesh, or the like to facilitate occlusion by one or more particles. Pores may be provided with internal ridges or ledges to facilitate occlusion by one or more particles. The lip or ridge may be at the top of the pore. The size of the exit from the pore (e.g., the exit diameter) may be decreased with respect to the pore opening to facilitate occlusion by particles. Shaping of pores may be combined with use of deformable particles. Shaping of pores may be combined with the use of particles carrying one or more reactive groups and in this embodiment shaped pores or the entrance or exit of the pores can be provided with compatible reactive groups to facilitate anchoring in the shaped pores. Shaping of the pores may be combined with any particle occluding method described herein. Shaping of the pores may be combined with polymerization of monomer and/or oligomers in shaped pores to occlude the pores.

In another embodiment, pore occlusion is obtained without introduction of an occluding moiety. In this embodiment, uncovered pores are occluded by the deformation or swelling of the substrate material forming the pore. In this embodiment, uncovered pores are selectively contacted to induce deformation or swelling of the substrate forming the pore to occlude the pore. Contacting can, for example, be with energy such as heat, light or an ion beam. Contacting can, for example, be with an absorbable fluid, such as water, aqueous solution or organic solvent, such that the substrate material at the pore swells to occlude the pore. In a related embodiment, the pores are provided with a deformable or swellable coating distinct from the substrate material. In this embodiment, selective contacting of uncovered pores with energy in the form, for example, of heat, light or an ion beam deforms the pore coating to occlude the pore. In this embodiment, where the coating is swellable, selective contacting of an uncovered pore with an absorbable fluid results in swelling to occlude the pore. Swellable coatings can, for example, be formed from swellable hydrogels or swellable polymers.

In an embodiment, the particles or other substrate pore occluding moieties are themselves selectively permeable having permeability that is selected for a given application. Permeable materials could include hydrogels, polymers, proteins, zeolites, metal-organic framework materials, or thin film solution membranes. The particles could also be covered with a semipermeable layer. An example would be a silica particle covered with polyethylene glycol. In an embodiment, the occluding particles are made at least in part of hydroxycellulose which is semi-permeable.

In an embodiment, particles, other occluding moieties, monomers, oligomers and optional polymerization catalysts, are introduced selectively into substrate pores that are not covered by two-dimensional material (uncovered substrate pores) by a flow of fluid, including liquid or gas. The flow of fluid or gas carrying the occluding moieties will not enter covered substrate pores. In an embodiment, selective introduction employs application of a cross-flow of fluid along the membrane and application of pressure. The cross-flow carrying occluding moieties is applied along the surface of the composite membrane upon which the two-dimensional material is disposed. In an embodiment, a flow of particles is applied to the top surface of a composite membrane and particles enter uncovered pores. The introduction step is optionally followed by a step of application of energy, a curing step or other step to facilitate anchoring of particles. Thereafter a cleaning step may be applied to the top surface of the composite material to remove particles that have not entered uncovered pores. Cycles of a particle introduction step, optional anchoring steps and a cleaning step may be repeated to achieve a desired level of pore occlusion. The effectiveness of pore occlusion can be assessed by flow rate measurements through an occluded composite membrane. More specifically, flow rate of a selected moiety (fluid, chemical species or particle) of a given size can be used to assess the effectiveness of substrate pore occlusion. In an embodiment, two or more of such cycles are performed. In an embodiment, five or more of such cycles are performed. In an embodiment, 9 or more of such cycles are performed.

In an embodiment, a pore occlusion process includes introduction of occluding moieties, more specifically particles, into substrate pores that are not covered by two-dimensional material (uncovered substrate pores). In an embodiment, a pore occlusion process further includes a step of removing occluding moieties that are not within substrate pores from the composite membrane. Introduction and removal (cleaning) steps can be repeated until a desired level of occlusion is achieved. In an embodiment, as described herein, a step of application of energy or chemical reaction can be applied after introduction of occluding moieties into substrate pores to facilitate anchoring of the moieties in the substrate pore.

In an embodiment, the methods herein for occluding defects, apertures or uncovered substrate pores are combined with methods of detection of defects or apertures in the two-dimensional material, such that occlusion methods are selectively applied to those portions of a sheet of two-dimensional material or those portions of a composite membrane where occlusion is needed. Such detection methods can include localized application of a selected assay fluid, e.g., a detectible gas, such as $SF_6$, to the two-dimensional material or to the composite membrane to detect the location (or approximate location) of defects, apertures or uncovered pores by passage of the assay fluid. Detection methods can also include localized resistance or capacitance measurement, where a change in resistance or capacitance is an indication of a defect or aperture. Detection methods can further include the localized detection of passage of analytes, particles, electrons or light, e.g., UV or visible light, through defects, apertures or through uncovered pores.

Some embodiments include a membrane comprising a cross-linked graphene platelet polymer comprising a plurality of cross-linked graphene platelets comprising a graphene portion and a cross-linking portion, the cross-linking portion contains a 4 to 10 atom link, and the cross-linked graphene platelet polymer being produced by reaction of an epoxide functionalized graphene platelet and a (meth)acrylate or (meth)acrylamide functionalized cross-linker. In some embodiments, the cross-linked graphene platelet polymer comprises cross-linked graphene platelets comprising a thiol moiety. In some embodiments, the cross-linked graphene platelet polymer further comprises a metal nanocluster. In some embodiments, the cross-linked graphene platelet polymer further comprises a quaternary alkyl-ammonium bromide. In some embodiments, the cross-linked graphene platelet polymer comprises cross-linked graphene platelets containing fluorocarbon functionalization. In some embodiments, each membrane is functionalized in a different manner. In some embodiments, a first filter comprises cross-linked graphene platelets comprising a thiol moiety. In some embodiments, a first filter comprises cross-linked graphene platelets comprising a quaternary alkyl-ammonium bromide. In some embodiments, a first filter comprises cross-linked graphene platelets comprising fluorocarbon.

Some embodiments a membrane comprising include a cross-linked graphene platelet polymer comprising a plurality of cross-linked graphene platelets, (a) comprising a graphene portion and a cross-linking portion, and the cross-linking portion contains a 4 to 10 atom link; or (b) comprising a plurality of graphene platelet portions and a plurality of cross-linking portions bound to the graphene platelet portions, wherein the cross-linking portions provide a spacing of about 1 nanometer between individual graphene platelet portions. In some embodiments, the cross-linked graphene platelet polymer comprises cross-linked graphene platelets comprising a thiol moiety. In some embodiments, the cross-linked graphene platelet polymer further comprises a metal nanocluster. In some embodiments, the cross-linked graphene platelet polymer further comprises a quaternary alkyl-ammonium bromide. In some embodiments, the cross-linked graphene platelet polymer comprises cross-linked graphene platelets containing fluorocarbon functionalization. Some embodiments include a filter module comprising at least two separate membranes of the above embodiments, wherein each membrane is functionalized in a different manner. In some embodiments, a first filter comprises cross-linked graphene platelets comprising a thiol moiety. In some embodiments, a first filter comprises cross-linked graphene platelets comprising a quaternary alkyl-ammonium bromide. In some embodiments, a first filter comprises cross-linked graphene platelets comprising fluorocarbon.

Other embodiments include a method of producing a filter or membrane composition comprising reacting one or more functionalized graphene platelets with one or more di-, tri- or tetra-functional crosslinking compounds. In some embodiments, the functionalized crosslinking compound is di-functionalized. In some embodiments, the crosslinking compound comprises one or more (meth)acrylate or (meth)acrylamide moieties. In some embodiments, the reacting step comprises applying e-beam or UV light to the one or more functionalized graphene platelets with one or more functionalized crosslinking compounds.

Other embodiments include a method of increasing purity of a liquid, comprising contacting a first portion of liquid having an impurity with a filter or membrane comprising a cross-linked graphene platelet polymer of any of the above embodiments to form a second portion of liquid, wherein the second portion of water contains a lower concentration of the impurity. In some embodiments, the liquid is an aqueous physiological liquid. In some embodiments, the liquid is water. In some embodiments, the impurity includes sodium and/or chloride ions. In some embodiments, the impurity includes an antibody. In some embodiments, the second portion of liquid is formed by passing the first portion of liquid through the filter comprising the cross-linked graphene platelet polymer. In some embodiments, the second portion of liquid contains 100-fold or less of the impurity as is found in the first portion of liquid.

Other embodiments include a method of producing a membrane composition comprising oxidizing a graphene platelet with an acid and an oxidizing agent at a temperature between 1 and 10 degrees Celsius to form a functionalized graphene platelet; and reacting one or more functionalized graphene platelets with one or more di-, tri- or tetra-functional crosslinking compounds.

Other embodiments include a method of producing a membrane precursor comprising oxidizing a graphene platelet with an acid and an oxidizing agent at a temperature between 1 and 10 degrees Celsius to form a functionalized graphene platelet; and reacting one or more functionalized graphene platelets to form a capped moiety that is not reactive under ambient conditions, but capable of converting to a reactive moiety upon, e.g., chemical, heat or UV treatment.

Other embodiments include a method of concentrating a composition of interest from a liquid or gas, comprising contacting a first portion of a liquid or gas having a material of interest with a filter comprising a cross-linked graphene platelet polymer of the above embodiments to form a second portion of liquid or gas, wherein the second portion of liquid or gas contains a lower concentration of the material of interest, and collecting the composition of interest that does not pass through the cross-linked graphene platelet polymer. In some embodiments, the liquid or gas is water. In some embodiments, the composition of interest is a rare-earth element.

Additional embodiments include a method of producing a membrane precursor comprising oxidizing a graphene platelet with an acid and an oxidizing agent at a temperature between 1 and 10 degrees Celsius to form a functionalized graphene platelet; and reacting one or more functionalized graphene platelets to form a capped moiety that is not reactive under ambient conditions, but capable of converting to a reactive moiety upon, e.g., chemical, heat or UV treatment.

Some embodiments describe methods for introducing pores into the basal plane of a plurality of graphene sheets stacked upon one another. In embodiments, the methods involve exposing about 5-20 layers of stacked graphene sheets (i.e., multi-layer graphene) to a particle beam having an ion energy of about 1500 eV or greater (per ion) to produce damage tracks in the basal planes of the stacked graphene sheets. In further embodiments, the ion energy greater than about 1500 eV but less than about 10000 eV or greater than 1.5 keV and less than 100 keV. Some embodiments further describe perforation methods including the step of exposing a sheet of graphene-based material to an ion beam, the graphene-based material comprising multilayer graphene having from 5 to 20 layers of graphene.

In embodiments, the damage tracks extend through the multi-layer graphene. Thereafter, the damaged graphene sheets are exposed to a chemical etchant, such as an oxidant, that selectively attacks defects (e.g. triple carbon-carbon bonds) in the damage tracks to remove graphene-based carbon atoms within the damage tracks. The damage tracks are tunable in size based upon the ion and energy used. In an embodiment, the oxidant is selected from the group consisting of ozone, an aqueous solution of potassium permanganate, an aqueous solution of potassium permanganate and sulfuric acid, an aqueous solution of potassium permanganate and potassium hydroxide or a solution of hydrogen peroxide and sulfuric acid In embodiments, the ion bombardment takes place while the graphene-based material is disposed on a substrate. In some embodiments, the bombardment and etching can take place while the graphene is disposed on a substrate. In embodiments, the substrate is a metal growth substrate or other substrate.

Multi-layer graphene sheets and graphene-based materials comprising multi-layer graphene having a plurality of pores penetrating through the stacked sheets are also described in some embodiments. Such perforated multi-layer graphene sheets will also be referred to herein as "perforated graphene" "perforated graphene-based materials" or "perforated two dimensional materials," In some embodiments, the perforations can be about 50 nm in size or less, 20 nm in size or less, 10 nm in size or less, or less than about 5 nm in size, particularly in a size range from about 0.2 nm to about 50 nm, 0.2 nm to about 20 nm, 0.2 nm to about 10 nm or from about 0.2 nm to about 5 nm. In embodiments, about 5 to about 20 stacked graphene sheets are present in the multi-layer graphene. In an embodiment, after perforation of the sheet the structure of the graphene based material in unperforated regions of the sheet is similar to that of the starting unperforated graphene based material.

In some embodiments, perforated graphene and perforated graphene-based materials comprising multilayered graphene produced by the techniques described herein can be used in filtration applications. The size or size range of perforations is adapted to the intended application. Some of the pore size ranges describe herein are suitable for reverse osmosis filtration and molecular filtration applications.

Some embodiments describe membranes comprising a perforated two-dimensional material disposed upon a porous support structure for use in blood dialysis and blood filtration applications. Such two-dimensional materials are selectively perforated to provide for selective removal of one or more components from the blood. Two-dimensional materials include for example graphene-based materials.

Some embodiments describe hemodialysis membranes and systems in which perforated graphene-based material and other perforated two-dimensional materials are used as a replacement for polymer membranes in conventional hemodialysis systems. The perforated two-dimensional material, such as graphene-based material and graphene, can have a pore size of similar magnitude to those used in conventional membranes, while providing much greater permeability due the thinness of the graphene. In addition, the pores or perforations in the two-dimensional material, such as graphene-based material, can be selectively sized, functionalized, or otherwise manipulated to tailor the selectivity of the hemodialysis separation process. In some embodiments, perforated graphene-based material can have added selectivity (e.g. tailored, smaller pores than conventional membranes) while maintaining permeability.

Some embodiments also describe hemodialysis methods in which blood is exposed to a hemodialysis membrane formed from perforated two-dimensional material, such as graphene-based material, and at least one component is removed from the blood upon contacting the perforated graphene. In an embodiment, the at least on component removed is urea, measurement of the extent of removal of which can be used to assess the effectiveness of a given hemodialysis method to remove low molecular weight toxic species, e.g., low molecular weight toxic species which contribute to disease. In an embodiment, at least one undesirable component is removed, such as a low molecular weight toxic species or a lower molecular weight (e.g., less than about 35 kDa) protein which contributes to uremia or other disorder, without removal of albumin at levels detrimental to a given patient. In an embodiment, at least urea is removed without removal of detrimental levels of albumin.

The foregoing has outlined rather broadly the features of some embodiments in order that the detailed description that follows can be better understood. Additional features and advantages of some embodiments will be described hereinafter. These and other advantages and features will become more apparent from the following description.

BRIEF DESCRIPTION OF THE DRAWINGS

FIG. 14B illustrates resultant anchoring of the particle in the substrate pore.

FIG. 15B illustrates resultant anchoring of the particle in the substrate pore

FIG. 4A is a scanning transmission electron microscope (STEM) image of single-layer graphene with pores of about 1 nm. FIG. 4B is a micrograph of CDV graphene-based material exhibiting pores ranging from about 0.5 to 1 nm in dimension. FIG. 4C is a micrograph of CDV graphene-based material exhibiting pores ranging from 2.5 to 7 nm in dimension. FIG. 4D is a micrograph of CDV graphene-based material exhibiting a mean pore size dimension of 6.3 nm, and which is about 4% open with about $1\times10^{11}$ pores/cm$^2$. Perforations are generated in the CDV graphene of FIGS. 32A-D using ion beam irradiation. FIG. 32E is a micrograph of CDV graphene-based material in which pores were introduced using focused ion beam (FIB) drilling and where the average pores size is 20 nm.

DETAILED DESCRIPTION

Figure 1:
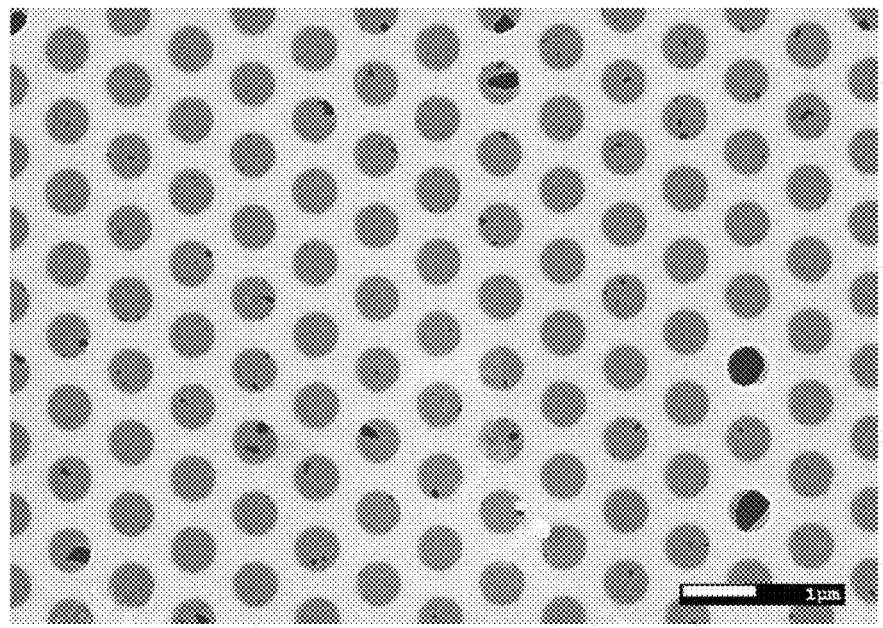
FIG. 1 shows an illustrative scanning electron microscope (SEM) image of defects and apertures that can be present in a graphene sheet on a porous substrate. The illustrated graphene sheet has been transferred to an etched silicon nitride film in a rigid silicon support to create a composite membrane. The diameter of arrayed substrate pores is 600 nm. Visible apertures in the graphene film appear black and range in size from approximately 10 nm (limit of SEM resolution) to 600 nm (fully uncovered substrate pore).

Method for Making Two-Dimensional Materials and Composite Membranes Thereof Having Size-Selective Perforations A variety of two-dimensional materials useful according to inventive concepts disclosed herein are known in the art. In various embodiments, the two-dimensional material comprises graphene, carbon nanomembranes (CNM), molybdenum disulfide, or boron nitride (specifically the hexagonal crystalline form of boron nitride). In an embodiment, the two-dimensional material is a graphene-based material. In more particular embodiments, the two-dimensional material is graphene. Graphene according to some embodiments can include single-layer graphene, multi-layer graphene, or any combination thereof. Other nanomaterials having an extended two-dimensional molecular structure can also constitute the two-dimensional material in some embodiments. For example, molybdenum sulfide is a representative chalcogenide having a two-dimensional molecular structure, and other various chalcogenides can constitute the two-dimensional material in some embodiments. Choice of a suitable two-dimensional material for a particular application can be determined by a number of factors, including the chemical and physical environment into which the graphene or other two-dimensional material is to be terminally deployed.

In an embodiment, the two dimensional material useful in membranes herein is a sheet of graphene-based material. Graphene-based materials include, but are not limited to, single layer graphene, multilayer graphene or interconnected single or multilayer graphene domains and combinations thereof. In an embodiment, graphene-based materials also include materials which have been formed by stacking independent single sheet or multilayer graphene sheets. In embodiments, multilayer graphene includes 2 to 20 layers, 2 to 10 layers or 2 to 5 layers. In embodiments, graphene is the dominant material in a graphene-based material. For example, a graphene-based material comprises at least 30% graphene by weight, or at least 40% graphene, or at least 50% graphene, or at least 60% graphene, or at least 70% graphene, or at least 80% graphene, or at least 90% graphene, or at least 95% graphene. In embodiments, a graphene-based material comprises a range of graphene content selected from 30% to 95%, or from 40% to 80% from 50% to 70%, from 60% to 95% or from 75% to 100%. In embodiments, a graphene-based material comprises a range of up to 35% oxygen by atomic ratio.

As used herein, a "domain" refers to a region of a material where atoms are uniformly ordered into a crystal lattice. A domain is uniform within its boundaries, but different from a neighboring region. For example, a single crystalline material has a single domain of ordered atoms. In an embodiment, at least some of the graphene domains are nanocrystals, having a domain size from 1 to 100 nm or 10-100 nm. In an embodiment, at least some of the graphene domains have a domain size greater than 100 nm to 1 micron, or from 200 nm to 800 nm, or from 300 nm to 500 nm, and in some embodiments, at least some of the graphene domains are nanocrystals, having a domain size up to about 1 cm. "Grain boundaries" formed by crystallographic defects at edges of each domain differentiate between neighboring crystal lattices. In some embodiments, a first crystal lattice may be rotated relative to a second crystal lattice, by rotation about an axis perpendicular to the plane of a sheet, such that the two lattices differ in "crystal lattice orientation".

In an embodiment, the sheet of graphene-based material comprises a sheet of single or multilayer graphene or a combination thereof. In an embodiment, the sheet of graphene-based material is a sheet of single or multilayer graphene or a combination thereof. In another embodiment, the sheet of graphene-based material is a sheet comprising a plurality of interconnected single or multilayer graphene domains. In an embodiment, the interconnected domains are covalently bonded together to form the sheet. When the domains in a sheet differ in crystal lattice orientation, the sheet is polycrystalline.

In embodiments, the thickness of the sheet of graphene-based material is from 0.34 to 10 nm, from 0.34 to 5 nm, or from 0.34 to 3 nm. In an embodiment, a sheet of graphene-based material comprises intrinsic defects. Intrinsic defects are those resulting from preparation of the graphene-based material in contrast to perforations which are selectively introduced into a sheet of graphene-based material or a sheet of graphene. Such intrinsic defects include, but are not limited to, lattice anomalies, pores, tears, cracks or wrinkles. Lattice anomalies can include, but are not limited to, carbon rings with other than 6 members (e.g. 5, 7 or 9 membered rings), vacancies, interstitial defects (including incorporation of non-carbon atoms in the lattice), and grain boundaries.

In an embodiment, a sheet of graphene-based material optionally further comprises non-graphenic carbon-based material located on the surface of the sheet of graphene-based material. In an embodiment, the non-graphenic carbon-based material does not possess long range order and may be classified as amorphous. In embodiments, the non-graphenic carbon-based material further comprises elements other than carbon and/or hydrocarbons. Non-carbon elements which may be incorporated in the non-graphenic carbon include, but are not limited to, hydrogen, oxygen, silicon, nitrogen, copper and iron. In embodiments, the non-graphenic carbon-based material comprises hydrocarbons. In embodiments, carbon is the dominant material in non-graphenic carbon-based material. For example, a non-graphenic carbon-based material comprises at least 30% carbon by weight, or at least 40% carbon, or at least 50% carbon, or at least 60% carbon, or at least 70% carbon, or at least 80% carbon, or at least 90% carbon, or at least 95% carbon. In embodiments, a non-graphenic carbon-based material comprises a range of carbon selected from 30% to 95%, or from 40% to 80%, or from 50% to 70%.

Two-dimensional materials in which pores are intentionally created are referred to herein as "perforated," such as "perforated graphene-based materials," "perforated two-dimensional materials," or "perforated graphene." Two-dimensional materials are, most generally, those which have atomically thin thickness from single-layer sub-nanometer thickness to a few nanometers and which generally have a high surface area. Two-dimensional materials include metal chalogenides (e.g., transition metal dichalogenides), transition metal oxides, hexagonal boron nitride, graphene, silicene and germanene (see: Xu et al. (2013) "Graphene-like Two-Dimensional Materials) Chemical Reviews 113:3766-3798).

Two-dimensional materials include graphene, a graphene-based material, a transition metal dichalcogenide, molybdenum sulfide, α-boron nitride, silicene, germanene, or a combination thereof. Other nanomaterials having an extended two-dimensional, planar molecular structure can also constitute the two-dimensional material in some embodiments. For example, molybdenum sulfide is a representative chalcogenide having a two-dimensional molecular structure, and other various chalcogenides can constitute the two-dimensional material in some embodiments. In another example, two-dimensional boron nitride can constitute the two-dimensional material in an embodiment of the inventive concepts disclosed herein. Choice of a suitable two-dimensional material for a particular application can be determined by a number of factors, including the chemical and physical environment into which the graphene, graphene-based or other two-dimensional material is to be deployed.

Some embodiments are directed, in part, to sheets of graphene-based material or other two-dimensional materials containing a plurality of perforations therein, where the perforations have a selected size and chemistry, as well as pore geometry. In embodiments, the perforated graphene, perforated graphene-based materials and other perforated two-dimensional materials contain a plurality of size-selected perforations ranging from about 3 to 15 angstroms in size. In a further embodiment, the perforation size ranges from 3 to 10 angstroms or from 3 to 6 angstroms in size. Some embodiments are further directed, in part, to perforated graphene, perforated graphene-based materials and other perforated two-dimensional materials containing a plurality of size-selected perforations ranging from about 3 to 15 angstroms in size and having a narrow size distribution, including but not limited to a 1-10% deviation in size or a 1-20% deviation in size. In an embodiment, the characteristic dimension of the perforations is from about 3 to 15 angstroms in size.

Some embodiments are also directed, in part, to perforated graphene, perforated graphene-based materials and other perforated two-dimensional materials containing a plurality of perforations ranging from about 5 to about 1000 angstroms in size. In further embodiments, the perforations range from 10 to 100 angstroms, 10 to 50 angstroms, 10 to 20 angstroms or 5 to 20 angstroms. In a further embodiment, the perforation size ranges from 100 nm up to 1000 nm or from 100 nm to 500 nm. Some embodiments are further directed, in part, to perforated graphene, perforated graphene-based materials and other perforated two-dimensional materials containing a plurality of perforations ranging from about 5 to 1000 angstrom in size and having a narrow size distribution, including but not limited to a 1-10% deviation in size or a 1-20% deviation in size. In an embodiment, the characteristic dimension of the perforations is from 5 to 1000 angstrom.

For circular perforations or apertures, the characteristic dimension is the diameter of the perforation or aperture. In embodiments relevant to non-circular pores, the characteristic dimension can be taken as the largest distance spanning the perforation or aperture, the smallest distance spanning the perforation or aperture, the average of the largest and smallest distance spanning the perforation or aperture, or an equivalent diameter based on the in-plane area of the perforation or aperture. As used herein, perforated graphene-based materials include materials in which non-carbon atoms have been incorporated at the edges of the pores.

Some embodiments describe methods directed to occluding apertures in a sheet of a graphene-based material or other two-dimensional material that are larger than a given threshold size, thereby reducing the plurality of apertures to a desired size and optionally with a specific chemistry. In embodiments, the reduced size of the aperture falls within the perforation and aperture size ranges given above. The threshold size can be chosen at will to meet the needs of a particular application. Perforations or apertures are sized as described herein to provide desired selective permeability of a species (atom, molecule, protein, virus, cell, etc.) for a given application. Selective permeability relates to the propensity of a porous material or a perforated two-dimensional material to allow passage (or transport) of one or more species more readily or faster than other species. Selective permeability allows separation of species which exhibit different passage or transport rates through perforations or apertures. In two-dimensional materials selective permeability correlates at least in part to the dimension or size (e.g., diameter) of perforations or apertures and the relative effective size of the species. Selective permeability of the perforations or apertures in two-dimensional materials such as graphene-based materials can also depend on functionalization of the perforation or aperture (if any) and the specific species that are to be separated. For electrically conductive two dimensional materials, selective permeability can be affected by application of a voltage bias to the membrane. Selective permeability of gases can also depend upon adsorption of a gas species on the filtration material, e.g., graphene. Adsorption at least in part can affect the local concentration of the gas species at the surface of the filtration material. Separation of two or more species in a mixture includes a change in the ratio(s) (weight or molar ratio) of the two or more species in the mixture after passage of the mixture through a perforated two-dimensional material.

The chemistry of the perforated apertures can be the same or different after being occluded according to the embodiments described herein. In various embodiments, occluding the apertures can involve occluding apertures within a particular size range such that no apertures remain within the size range, thereby conferred selectivity to the "healing" of the graphene-based material or other two-dimensional material. The embodiments of the healing processes described herein are applicable to both "through-holes" (i.e., pores in a single two-dimensional sheet) and "intralayer flow" (i.e., channels existing between stacked layers of individual single layer two-dimensional sheets or multiple layer sheets of 2D material. Channels can include laterally offset pores within multiple two-dimensional sheets. Through-holes can also exist in multiple two-dimensional sheets when the pores are not substantially laterally offset from one another in the various layers The embodiments described herein allow specific chemistries to be readily applied in a homogenous manner to graphene-based materials and other two-dimensional materials to allow for tunable activity across many applications. While the chemistries described herein can be applied homogenously to an entire surface of the sheet of graphene or other two-dimensional material, they generally provide specific activation of particular perforations or apertures of a given size using a carefully sized moiety that allows for aperture modification to take place. The described techniques can be advantageous in allowing the homogenous application of chemistry to the graphene-based material or other two-dimensional material surface while only occluding perforations or apertures of a certain desired size. The homogenous application of the various chemistries described herein can facilitate scalable production and manufacturing ease. Perforation or aperture modification can confer a specific chemistry to the perforations or apertures (e.g., functional selectivity, hydrophobicity, and the like) and allow for at least partial occlusion of the perforations or apertures to take place in various embodiments. Such selective modification of the apertures can allow selective separations to take place using the graphene-based material, including size-based separations.

For example, perforations or apertures can be selectively modified by various known methods to contain hydrophobic moieties, hydrophilic moieties, ionic moieties, polar moieties, reactive chemical groups, for example, amine-reactive groups (chemical species that react with amines) carboxylate-reactive groups (chemical species that react with carboxylates), amines or carboxylates (among many others), polymers and various biological molecules, including for example, amino acids, peptide, polypeptides, enzymes or other proteins, carbohydrates and various nucleic acids.

Furthermore, the techniques described herein can be configured to at least partially occlude large apertures within the sheet of graphene-based material or other two-dimensional material in preference to smaller apertures, thereby allowing the smaller apertures to remain open and allow flow to be maintained therethrough. This type of selective flow can allow molecular sieving to take place using the graphene-based material or other two-dimensional material, rather than the solution-diffusion model provided by current polymeric solutions. In some aspects, apertures or defects are blocked to provide flow reduction or blockage within a range of 50% or more, 60% or more, 70% or more, 80% or more, 90% or more, 95% or more. In further aspects, however, all the apertures and/or defects in a graphene-based material or other two-dimensional material can be occluded in order to substantially block passage or flow, herein 99% or more through the two-dimensional material or block passage or flow through the two-dimensional material entirely. In an embodiment, a graphene-based material or other two-dimensional material that is occluded in order to substantially or entirely block passage or flow through the material can be used as a starting material for forming a size-selected perforated two-dimensional material. Size-selected perforations can be introduced into the substantially or entirely blocked two-dimensional material employing art known methods for generating perforations of a selected size and, if any, a selected functionalization.

Although the description herein is primarily directed to graphene-based materials, it is to be recognized that other two-dimensional materials or near two-dimensional materials can be treated in a like manner. The at least partially occluded graphene-based materials prepared according to the techniques described herein can be used for occluding fluid flow, particularly liquid or gas flow for separations, including filtration membranes and filtration systems. In addition, they can be used in optical or electronic applications.

In some embodiments, the graphene-based material can be transferred from its growth substrate to a porous substrate in the course of, before or after practicing the embodiments described herein.

By way of example, a sheet of a graphene-based material or sheet of another two-dimensional material can have a plurality of perforations therein, and a direction of fluid flow therethrough can establish an "upstream" side (alternative the top surface) and a "downstream" side (alternatively the bottom surface) of the sheet. The downstream side of the sheet of the graphene-based material or sheet of another two-dimensional material can be next to or in contact with a substrate, such as a porous substrate. In some embodiments, the substrate can provide support to the sheet of the graphene-based material while practicing the various techniques described herein. The perforations in the sheet of a graphene-based material or sheet of another two-dimensional material can be intentionally placed therein, or they can occur natively during its synthesis. According to some embodiments, the perforations can have a distribution of sizes, which can be known or unknown. By placing an occluding moiety within a flow contacting the graphene-based material or other two-dimensional material, apertures having a desired size profile can become occluded according to the embodiments described herein.

In some embodiments described herein, a fluid containing a sized moiety can be flowed through the sheet of graphene-based material or other two-dimensional material. The sized moiety can lodge in some of the apertures in the sheet and induce occlusion of at least the portion of the apertures in the sheet in which the sized moiety lodges. In other embodiments, a sized moiety can occlude fluid flow on the sheet of graphene-based material or other two-dimensional material from the upstream side of the graphene. Various embodiments of these various flow configurations are described below.

Occluding at least a portion of the apertures in the foregoing manner can result in reducing the size and number of apertures, possibly modifying a flow path and making the graphene-based material or other two-dimensional material suitable for use in an intended application. For example, the graphene-based material or sheet of another two-dimensional material can be processed in the foregoing manner to produce a cutoff pore size in a molecular filter. Depending on the nature of the moiety in the flow path, the moiety can be covalently or non-covalently attached to the graphene-based material, or mechanically connected to the graphene-based material.

In some embodiments, the "downstream" side of the sheet of graphene-based material can be "primed" or functionalized with oxygen via plasma oxidation or the like, such that the graphene-based material can be reactive with a moiety passing through the apertures. In some embodiments, the moiety in the flow path can bind to functional groups introduced to the graphene-based material, such that the moiety binds to the graphene-based material and the apertures become at least partially occluded. Suitable binding motifs can include, but are not limited to, addition chemistry, crosslinking, covalent bonding, condensation reactions, esterification, polymerization. In various embodiments, the occluding moiety can be sized to reflect a particular cutoff regime, such that it only passes through apertures having a certain threshold size or shape. For example, in various embodiments, the occluding moieties can be a substantially flat molecule or spherical in shape. POSS® silicones (polyhedral oligomeric silsesquioxanes), for example, represent one particular type of occluding moiety that can be made at a very specific size and functionalized to tether to oxygenated functionalization on the apertures. Other examples, of useful occluding moieties include fullerenes, dendrites, dextran, micelles or other lipid aggregates, and micro-gel particles. Some or all of these techniques may be applied to other two-dimensional materials as well.

In various embodiments, the graphene-based material can be perforated and functionalized with oxygen, such as treating the graphene-based material with oxygen or a dilute oxygen plasma, thereby functionalizing the graphene-based material with oxygen moieties. In some embodiments, the graphene based material can be functionalized in this manner while on a copper substrate, or any other metallic/growth, or polymeric substrate as it would be understood by one of skill in the art. Subsequently, the oxygen functionalities can be reacted via a chemistry that converts the oxygenated functionalities into a leaving group (such as a halide group, particularly a fluoro group, or sulfonic acid analogs, such as tosylates, triflates, mesylates, and the like). This chemistry results in sites on the substrate that are vulnerable to nucleophilic attack and can be used for additional chemistry, as detailed above, or allowing the graphene based material to bind to the substrate. In some embodiments, the graphene-based material can functionalized with oxygen so as to provide graphene oxide platelet membranes.

Figure 2:
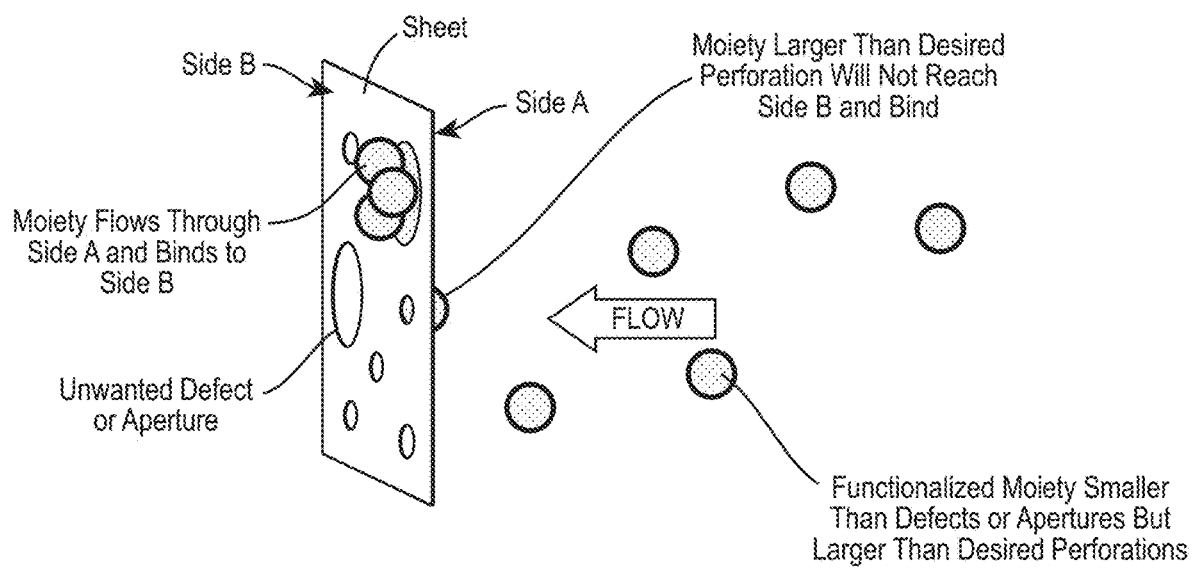
FIG. 2 shows an illustrative schematic demonstrating how a perforated graphene sheet or sheet of another two-dimensional material can undergo backside functionalization according to concepts described herein.

FIG. 2 shows an illustrative schematic demonstrating how a graphene sheet or sheet of another two-dimensional material can undergo backside functionalization according to the embodiments described herein to occlude undesired apertures or defects in the sheet. In the drawings, Side A refers to the side of the graphene or other two-dimensional material being exposed to the upstream flow and Side B refers to the backside of the graphene or other two-dimensional material. In certain embodiments, the flow may be across the two dimensional material instead of merely through. The backside of the sheet may be primed or activated to react with the occluding moieties. In an embodiments, the backside of the sheet is functionalized to bind or react with occluding moieties. As shown in FIG. 2, the occluding moieties do not pass through aperture or defects having a size too small for the occluding moieties to pass through, but the occluding moieties do pass through the larger undesirable apertures or defects. On passage through the undesired apertures or defects, the occluding moieties react and/or bind at the aperture or defect and occlude the aperture or defect. The flow is sufficiently high that diffusion of occluding moieties on the backside of the sheet away from the aperture that they exit is minimized to avoid occlusion of the smaller apertures or defects. While the aforementioned chemistry provides a technique for backside attack, it should also be recognized that a sheet of graphene or other two-dimensional material can also be functionalized or primed such that it can undergo front side attack, particularly in cases where transfer is less desirable during the processing of a product. Front side attack can ensure retention of configuration. Front side attack can occur similarly to the methods depicted in FIG. 2, with the exception that bonding occurs on the upstream or Side A of the graphene sheet or sheet of other two-dimensional material and there may be less selectivity in bonding holes of a desired size over larger apertures. In an embodiment, methods to permit front side attack on the surface of a graphene-based material again begin with an oxygen functional group on the surface of the graphene-based material, which are treated with an agent such as pyridine, triflate, or analogs thereof to provide a good leaving group. Subsequent chemistry can be conducted to remove the copper growth substrate and use additional chemistry to occlude holes or apertures below the diameter which the moiety may pass. Note that both front side and back side approaches allow for a homogenous application of chemistries, which can be desirable for scalability.

Figure 3:
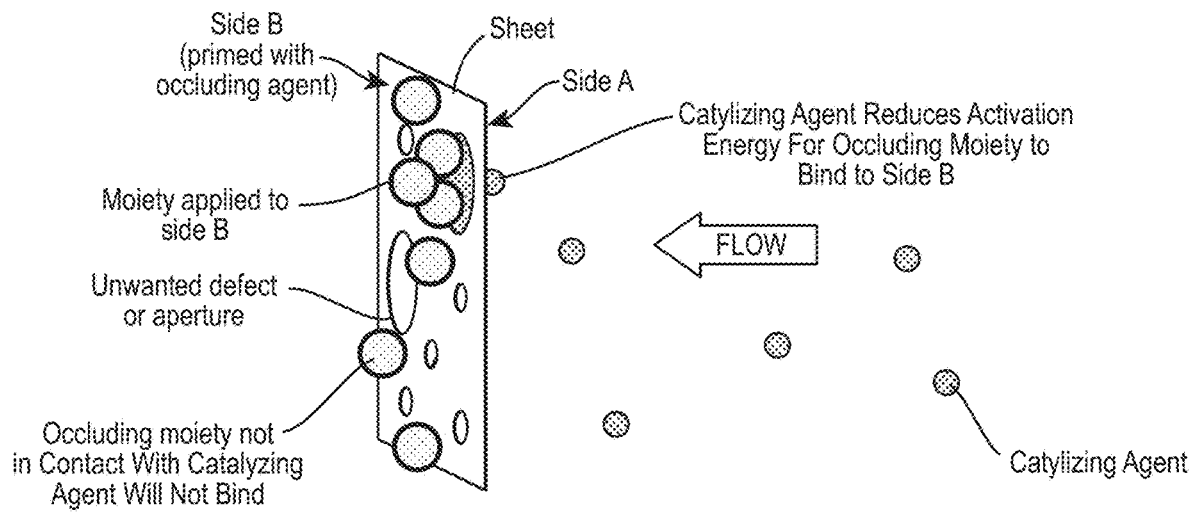
FIG. 3 shows an illustrative schematic demonstrating how a perforated graphene sheet or sheet of another two-dimensional material can undergo occlusion by flowing a catalyst there through according to concepts described herein.

In other embodiments, the downstream side of the graphene-based material or other two-dimensional material can be primed with an occluding substance and a moiety that catalyzes the reaction of the occluding substance with the graphene or other two-dimensional material can pass through the apertures. Thus, in this case, the moiety does not become bonded to the graphene or other two-dimensional material itself. FIG. 3 shows an illustrative schematic demonstrating how a perforated graphene sheet or sheet of another two-dimensional material can undergo occlusion by flowing a catalyst therethrough. In more particular embodiments, the methods can include treating the graphene or graphene-based material with lithium and an appropriate charge transfer catalyst in order to create polyethylene glycol chains around the periphery of the graphene perforations. In some embodiments, such a reaction scheme can be conducted under substantially anhydrous conditions. In some embodiments, the moiety in the flow can catalyze the reaction with a polymer substrate (e.g., upon which the graphene-based material or other two-dimensional material is placed following transfer from its growth substrate), which can be considered a subset of the foregoing embodiments.

In the foregoing embodiments, also depicted in FIGS. 2 and 3, priming the graphene-based material can involve casting a porous substrate, such as a polymer substrate, onto the graphene-based material when it is on its copper growth substrate. The copper can then be etched away. Thereafter, the porous substrate can be exposed to light or some other form of electromagnetic radiation to cause a change in the substance, thereby making it no longer permeable. In alternative embodiments, the porous substrate can be exposed to a compound that binds to the porous substrate. In still other alternative embodiments, the porous substrate can maintain its porosity when practicing the embodiments described herein.

Figure 4:
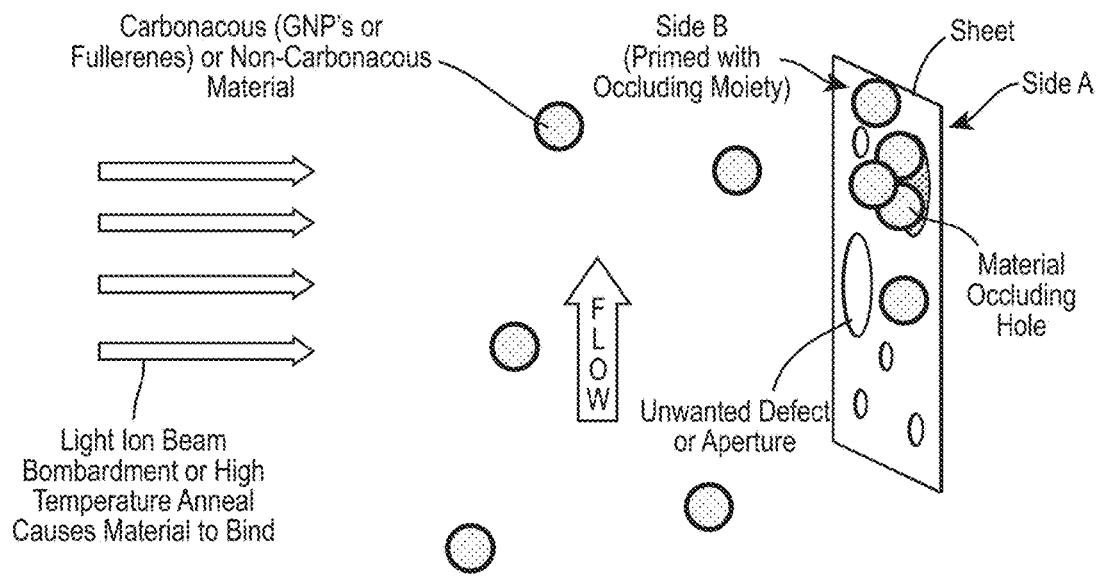
FIG. 4 shows an illustrative schematic demonstrating how a perforated graphene sheet or sheet of another two-dimensional material can undergo occlusion with a carbonaceous material or a non-carbonaceous material in the presence of a light ion beam, or a high temperature annealing step according to concepts described herein.

In still further embodiments, carbonaceous or non-carbonaceous materials can be flowed over the graphene based material or other two-dimensional material and become tethered to the open apertures. Suitable materials can include, for example, graphene nanoplatelets (GNPs), fullerenes of various sizes, hexagonal boron nitride, or carbon nanotubes. In more particular embodiments, tethering of the carbonaceous or non-carbonaceous material can be accomplished by utilizing a light or gentle ion beam, a high temperature annealing step, exposing to light to generate a photo-active reaction. The high temperature annealing step could comprise isocyanate crosslink chemistry. In some embodiments, flow through the two-dimensional material can become completely blocked. In some embodiments, smaller apertures can remain open. FIG. 4 shows an illustrative schematic demonstrating how a perforated graphene sheet or sheet of another two-dimensional material can undergo occlusion with a carbonaceous material or a non-carbonaceous material in the presence of a light ion beam or a high temperature annealing step. In the depicted embodiments, the carbonaceous or non-carbonaceous materials are flowed laterally across the sheet of graphene-based material or other two-dimensional material, rather than passing through the apertures. In alternative embodiments, the carbonaceous materials or non-carbonaceous materials can be flowed through the sheet of graphene-based material or other two-dimensional material.

Figure 5:
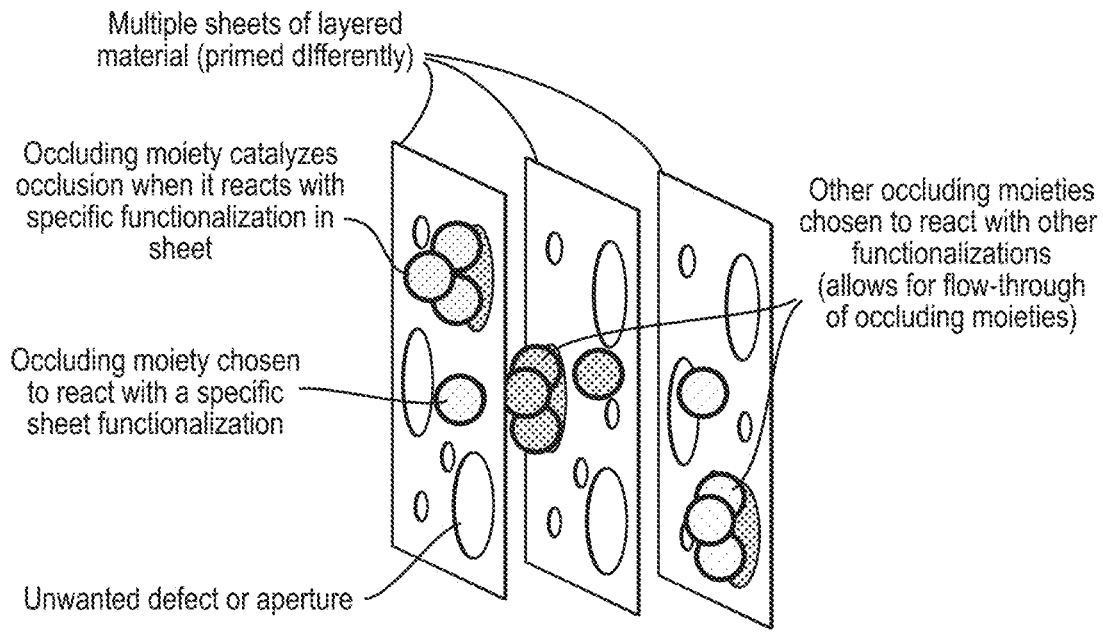
FIG. 5 shows an illustrative schematic demonstrating how apertures in multiple layered graphene sheets or sheets of other two-dimensional materials can become differentially occluded according to concepts described herein.

In still other embodiments, functionalization or activation of multiple, potentially different layered sheets of graphene-based materials or other two-dimensional material (e.g. complementary chemistries) can be leveraged to allow for flow not only through channels, but also via intralayer flow. Healing or partial occlusion can result from further modification of apertures. That is, layered sheets of two-dimensional material can be differentially functionalized according to the embodiments described herein. FIG. 3 shows an illustrative schematic demonstrating how a perforated graphene sheet or sheet of another two-dimensional material can undergo occlusion by flowing a catalyst there through. FIG. 4 shows an illustrative schematic demonstrating how a perforated graphene sheet or sheet of another two-dimensional material can undergo occlusion with a carbonaceous material or a non-carbonaceous material in the presence of a light ion beam, or a high temperature annealing step. FIG. 5 shows an illustrative schematic demonstrating how apertures in multiple layered graphene sheets or sheets of other two-dimensional materials can become differentially occluded. In some embodiments, the functionalization can be chosen such that apertures of different sizes are occluded in the various graphene sheets.

Some embodiments are directed, in part, to composite membranes formed from a porous substrate having a plurality of pores with a sheet of two-dimensional material disposed on the surface of the porous substrate and defining a top surface of the composite membrane. A portion of the pores of the substrate are covered by the two-dimensional material and a portion of the pores of the substrate are not covered by the two-dimensional material due, for example, to defects formed during synthesis of the two-dimensional material, formed during handling of the two-dimensional material, or formed when the two-dimensional material is disposed on the porous substrate. Defects or apertures in the two-dimensional material can result in undesired passage of species through the composite membrane. It is desired for use in filtration applications, that substantially all of the substrate pores are covered by the two-dimensional material so that passage through the membrane is primarily controlled by passage through the two-dimensional material. In a specific embodiment, substantially all pores of the substrate are covered by a two-dimensional material that contains perforations of a desired size range for selective passage through the membrane. In a specific embodiment, perforations in the two-dimensional material have a selected chemistry at the perforation as discussed above. The perforation in the two-dimensional material can have selected size or selected size range and discussed above. In a specific embodiment, the two-dimensional material is a graphene-based material. In a specific embodiment, the two-dimensional material is a graphene-based material which comprises single-layer graphene or multi-layer graphene.

Some embodiments provide methods for occluding uncovered substrate pores in the composite membrane as described above. In an embodiment, the method includes introducing one or more occluding moieties at least partially into at least one uncovered pore to occlude the at least one uncovered pore. In specific embodiments, 50% or more of the uncovered substrate pores are occluded. In more specific embodiments, 60% or more, 75% or more, 80% or more, 90% or more, 95% or more or 99% or more of the uncovered substrate pores are occluded. In specific embodiments, occlusion of uncovered pores reduced flow through the composite membrane (compared to the non-occlude membrane) by 50% or more. In specific embodiments, occlusion of uncovered pores reduced flow through the composite membrane (compared to the non-occluded membrane) by 60% or more, 75% or more, 80% or more, 90% or more, 95% or more or 99% or more.

The extent of occlusion of uncovered pores can be assessed by various methods. Detection of uncovered pores can, for example, be assessed using a selected assay fluid, e.g., a detectible gas, such as $SF_6$, to detect the location (or approximate location) of uncovered pores by passage of the assay fluid. Uncovered pores may be detected by use of the passage of detectible chemical species, particles, electrons, UV or visible light through the pores. The presence of uncovered pores can also be detected by various imaging methods. The presence and or location (or approximate location) of pores can be assessed using various imaging methods (including scanning electron microscopy, scanning probe microscopy, scanning tunneling microscopy, atomic force microscopy, transmission electron microscopy, x-ray spectroscopy, etc.); detecting analyte, particles or ions passing through pores (using mass spectrometry, secondary mass spectrometry, Raman spectroscopy, residual gas analysis, detecting Auger electrons, detecting nanoparticles using a microbalance, detecting charged species with a Faraday cup, detecting secondary electrons, detecting movement of analyte through defects, employing an analyte detector, identifying a composition, mass, average radius, charge or size of an analyte; detecting electromagnetic radiation passing through defects; detecting electromagnetic radiation given off by analyte; and detecting electromagnetic radiation or particles back scattered from the membrane.

Uncovered substrate pores include those pores that are only partially covered, but through which non-selective passage can occur.

The porous substrate of the composite membrane can be any porous material compatible with a disposed two-dimensional material and particularly with a graphene-based material. The porous substrate is selected to be compatible with the application for which the composite membrane is intended. For example, compatible with the gases, liquids or other components which are to be in contact with the composite membrane. The porous substrate provides mechanical support for the two-dimensional material and must maintain this support during use. The porous support should substantially retain pores that are covered with two-dimensional material. In specific embodiments, the porous material is made of a polymer, metal glass or a ceramic The pores in the substrate can have uniform pore diameter along the length of the pore, or they can have a diameter that varies along this length. Pores or pore openings (entrance or exit) can be shaped, as discussed below, to facilitate retention of occluding moieties in uncovered pores. Pores may be tapered, ridged or provided with one or more ledges to facilitate retention of occluding moieties in uncovered pores. In a specific embodiment, the pore entrance and/or the pore exit is narrowed compared to the rest of the pore to facilitate retention of occluding moieties. Pores in the substrate are preferably of uniform size and uniform density (e.g., uniformly spaced along the substrate). Pores may be independent or may be interconnected with other pores (tortuous or patterned). In embodiments, pores sizes (e.g. diameters) can range from 10 nm to 10 microns or more preferably from 50 nm to 500 nm. For methods and composite membranes herein a top surface of the membrane is defined as the surface upon which the two-dimensional material is disposed. One surface contains pore entrance openings and the second surface contains pore exit openings. Introduction of occluding moieties is through pore entry openings so that introduction of such moieties is selectively into pores that are not covered by two-dimension materials. Pore entrance and exits are defined by flow direction through pores.

Occluding moieties most generally include any material that can be selectively introduced into uncovered pores and retained therein to occlude the pore. A step of chemical reaction, application of energy in the form of heat, electromagnetic radiation (e.g., UV, visible or microwave irradiation), or contact with an absorbable material can be applied to deform, swell, polymerize, cross-link or otherwise facilitate retention of occluding materials in a pore. In an embodiment, the occluding materials are one or more particles sized for entrance at least in part into an uncovered pore. Particle size and pore shape may be selected to facilitate retention in the uncovered pores. Particles may be deformable, for example, by application of pressure, heat, microwave radiation or light of a selected wavelength (e.g. UV light), or by ion bombardment. Deformable particles introduced into pores are retained in pores after deformation. Particles may be swellable, where the size of a particle increases on contact with an absorbable material which induces swelling. The absorbable material can, for example, be a fluid including liquids or gases, water or an aqueous solution or a miscible mixture of water and an organic solvent, a polar organic solvent or a non-polar organic solvent. The swellable particle and the absorbable fluid are selected to achieve a desired level of swelling to achieve retention in the pore.

Occluding particles can be made of any suitable material. In specific embodiments, particles selected from metal particles, silica particles, particles of metal oxide, or polymer particles. In specific embodiments, particles are made of melamine, polystyrene or polymethyl methacrylate (PMMA). In a specific embodiment, the particles are made of latex (polystyrene). In specific embodiments, the substrate pore occluding particles are themselves permeable to provide a selective permeance through the occluded pores. In specific embodiments, the substrate pore occluding particles are permeable to fluid flow and provide for separation of components in the fluid. Permeable materials could include hydrogels, polymers, proteins, zeolites, metal-organic framework materials, or thin film solution membranes.

Particle size is generally selected based on the pores sizes present in the substrate so that the particle can enter the pore and be retained in the pore. Particles may be monodisperse if the pore entrance openings are uniform in size. A mixture of particles of different sizes can be employed when pore openings are non-uniform in size. A mixture of particles of different sizes (having a selected particle size distribution or being polydisperse in size) can be used, if pores with different (or unknown sizes) are present in the substrate. In an embodiment, the occluding particle is selected to have particle size that is approximately the same size as a pore entrance opening. The occluding particle may be slightly larger for tapered pores and slightly smaller for non-tapered pores such that the pores have a larger cross-section on the side of the substrate exposed to upstream flow. In an embodiment, particles are sized for at least partial introduction into an uncovered pore, but wherein the particle cannot exit the uncovered pore. Exit from the pore can be inhibited or prevented by using shaped pores in which the pores are narrowed at some point along its length. Particles useful in the methods herein will in an embodiment range in size from 10 nm to 10 microns.

In an embodiment, employing deformable or swellable particles, the respective particles are deformed or swollen after introduction to an uncovered pore.

In an embodiment occlusion may be facilitated through controlled fouling, where a fluid is flowed to the composite membrane surface, and material from the fluid is bonded to composite membrane pores that are defective. The fouling may be controlled such that it blocks non-selective pores.

In an embodiment occlusion may be facilitated through healing with particles in air. Particles are aerosolized and/or suspended in air and then forced through the membrane, such as by having convective flow of the air through the membrane. The convective flow of the air could be facilitated by applying a pressure differential across the membrane. The particles could be those described herein, with the methods described herein for fixing the particles to the membrane.

In an embodiment, occluding particles carry one or more chemical reactive groups for reaction with compatible reactive groups in the at least one uncovered pore, on the surface of the substrate at the uncovered pore or on other particles to facilitate anchoring of at least one particle in at least one uncovered pore. The particles can carry any one or more of a reactive chemical species, for example, the reactive species may be an amine, a carboxylate acid, an activated ester, a thiol, an aldehyde or a hydroxyl group. Particles useful in the inventive concepts disclosed herein which carry reactive groups can be prepared by known methods or may be obtained from commercial sources. Reactive groups on the particles can react with compatible reactive groups on the surface of the substrate at an uncovered pore, within the pore or at pore openings to facilitate retention in the pore. In an embodiment, particles may react with other particles in the pore to facilitate retention in the pore. One of ordinary skill in the art can employ a variety of chemically reactive groups to facilitate reaction with a pore to facilitate retention and anchoring in the pore. It will be appreciated that chemical reaction between particles, between particles and the pore surface, edges, openings or exits can be activated or induced by introduction of a reactive species, reagent or catalyst into a pore containing at least one occluding particle. It will also be appreciated that a chemical reaction between particles, between particles and the pore surface, edges, openings or exits can be activated or induced, for example, by heating, microwave irradiation, irradiation with light of selective wavelength (e.g., UV radiation) or by application of an ion beam, or by any method known in the art that is compatible with the materials employed.

In an embodiment, the occluding moieties are selected from one or more monomers, oligomers, uncured polymers or uncross-linked polymers. These occluding moieties are introduced selectively into uncovered pores and wherein the monomers, oligomers or polymers are polymerized, cured or cross-linked after they are introduced into the at least one uncovered pore. Polymerization can be effected for example by introduction of a polymerization catalyst, heating, microwave irradiation, or irradiation with light of a selected wavelength or by any method known in the art that is compatible with the materials employed. Curing of an uncured polymer or cross-linking of a polymer can be effected by any art-known method, for example by introduction of a curing or cross-linking reagent or application of heating, microwave irradiation, or irradiation with light of a selected wavelength or by any method known in the art that is compatible with the materials employed.

In an embodiment, the occlusion method further comprising a second step of introducing secondary particles into the at least one uncovered pore having a first particle therein occluding the uncovered pore, where the secondary particles are sized to be smaller than the first particle. In this embodiment, the initial particle and the secondary particles may be deformable or swellable as described above and may be deformed or swollen after introduction of the secondary particles. The initial particle and the secondary particles may carry one or more reactive groups as described above for chemical reaction of particles in the pores to facilitate retention in the pore.

In an embodiment, the composite membrane further comprises a coating layer on the top surface of the porous substrate between that surface and the sheet of two-dimensional material. Chemical reaction of a particle or other occluding moiety with reactive species on this coating at the entrance of the uncovered pore can facilitate anchoring and retention in the pore.

Occluding moieties are introduced to the top surface of the composite membrane where the occluding moieties can enter uncovered substrate pores. Introduction can be by any appropriate method and preferably is by application of a flow of fluid containing a selected concentration of occluding moieties. In a specific embodiment, the fluid is an aqueous solution carrying a selected concentration of occluding moieties. The concentration of occluding moieties in the flow introduced can be readily optimized empirically to optimize the effectiveness or efficiency of occlusion. Effectiveness or efficiency of occlusion can be assessed by measurement of the flow rate through the composite membrane, by accumulation rate of permeate or by an assessment of the selectivity of flow. A decreasing flow rate or a leveling off of permeate accumulation indicates successful occlusion. In an embodiment, the flow of occluding moieties includes a surfactant to decrease or minimize clumping or aggregation of occluding moieties and to facilitate entry of occluding moieties into uncovered pores. The inclusion of an appropriate surfactant is particularly beneficial for the introduction of occluding particles. In a specific embodiment, the surfactant is a non-ionic surfactant, such as (polyethylene glycol sorbitan monooleate). One of ordinary skill in the art can readily select a surfactant appropriate for the methods herein.

In a preferred embodiment, introduction of occluding moieties to the top surface of the composite membrane is by application of a cross-flow to the surface. The velocity of the cross-flow can be varied according to desired results. According to an embodiment, the pressure and flow may be varied as desired. In an embodiment, the shear velocity of the flow may be controlled. In an embodiment, the pressure across the composite membrane may be stopped while shear flowing. In an embodiment, the pressure on both sides of the membrane may be equalized. In an embodiment, the pressure may be controlled in cycles to alternately provide flow forward and then backward. The pressure on one or both sides of the membrane may be pulsed. Further, peristaltic pump rate and dimensions of the channel through the composite membrane may be controlled according to embodiments.

In an embodiment, the pore occlusion method further comprising a step of cleaning the top surface after introduction of occluding moieties into uncovered pores to remove occluding moieties that have not entered uncovered pores. This cleaning step can comprise flow of an appropriate fluid (gas or liquid) to or across the top surface of the membrane. In a specific embodiment, a flow of water or an aqueous solution is applied to or across the top surface of the membrane. In a specific embodiment, the aqueous solution contains a surfactant (as discussed above) to decrease clumping or aggregation of particles on the top surface.

In an embodiment, the introduction and cleaning steps as well any intervening steps to facilitate retention of particles in uncovered pores (e.g., deformation, chemical reaction, swelling or application of energy) are repeated until additional occlusion of pores ends or until a selected level of uncovered pore occlusion is achieved. As discussed above, various methods for accessing the extent or efficiency of pore occlusion can be employed.

In an embodiment, cycles of introduction and cleaning can be repeated until at least 80% of the uncovered pores are occluded. In an embodiment, cycles of introduction and cleaning can be repeated until at least 95% of the uncovered pores are occluded. In an embodiment, cycles of introduction and cleaning can be repeated until at least 99% of the uncovered pores are occluded.

In preferred embodiments, the two-dimensional material is a graphene-based material. In preferred embodiments, the two-dimensional materials is a sheet of graphene containing single layer graphene, few layer graphene (having 2-20 layers) or multilayer graphene.

In an embodiment, the pore occlusion method can be practiced without introducing an occluding moiety into uncovered pores. In this embodiment, a composite membrane as discussed above is provided wherein a sheet of two-dimensional material covers at least a portion of the pores of the substrate; but wherein at least one pore of the substrate is not covered by the two-dimensional material. In this embodiment, the substrate material forming the pores comprises a swellable material. The substrate itself may be made of a swellable material or more preferably the substrate material surrounding the pores is formed of a swellable material. For example, a coating of swellable material can be applied to the inside surfaces of the substrate pores. Selective introduction of an absorbable material into the uncovered pores results in local swelling of the swellable material surrounding the uncovered pore and occlusion of the uncovered pore. In an embodiment, the uncovered pores are selectively contacted with an absorbable fluid.

Some embodiments further provide a composite membrane comprising a porous substrate having a plurality of pores and a sheet of two-dimensional material disposed on a surface of the porous substrate and defining a top surface of the membrane, wherein the sheet of two-dimensional material covers at least a portion of the pores of the substrate, wherein at least one pore of the substrate is not covered by the two-dimensional material and wherein at least one uncovered pore of the substrate is occluded with an occluding moiety. In an embodiment, the composite membrane has at least one uncovered pore occluded with one or more particles or occluded with a polymer, cured polymer or cross-linked polymer formed in the at least one uncovered pore.

Figure 6:
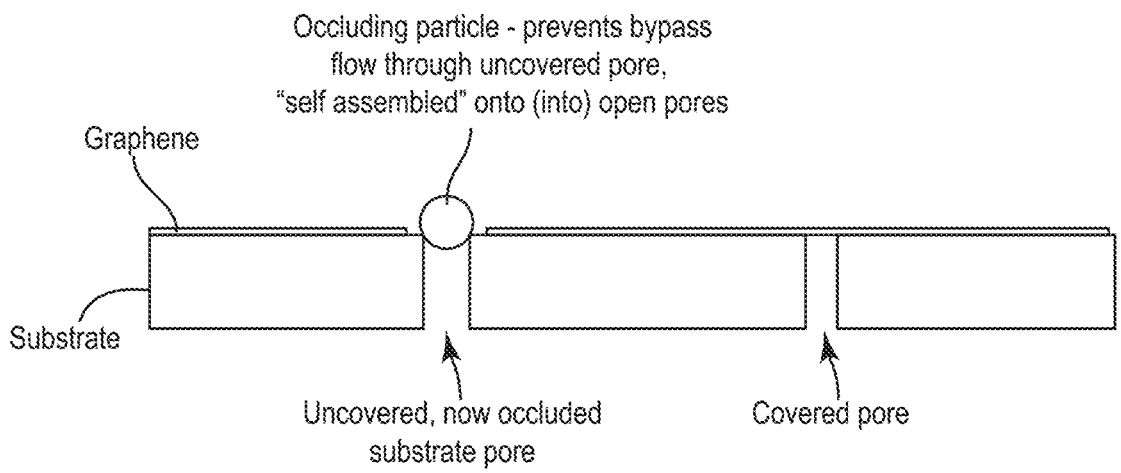
FIG. 6 shows an illustrative schematic demonstrating occlusion of uncovered substrate pores in a composite membrane having a graphene-based material sheet disposed upon a porous substrate according to concepts described herein.

FIG. 6 schematically illustrates occlusion of uncovered pores in the substrate of a composite membrane having a graphene-based material sheet disposed upon a porous substrate forming a top surface thereof. The occluding moiety is illustrated as a particle. A particle, size-selected based on pore size, to at least partially enter an uncovered pore is illustrated. As discussed herein a plurality of particles are introduced to the top surface of the membrane and a portion of the particles enter and are retained in the uncovered pores. A particle enters at least one uncovered pore and occludes the pore preventing passage though the occluded pore. The substrate may be pre-wetted in some embodiments.

Figure 7:
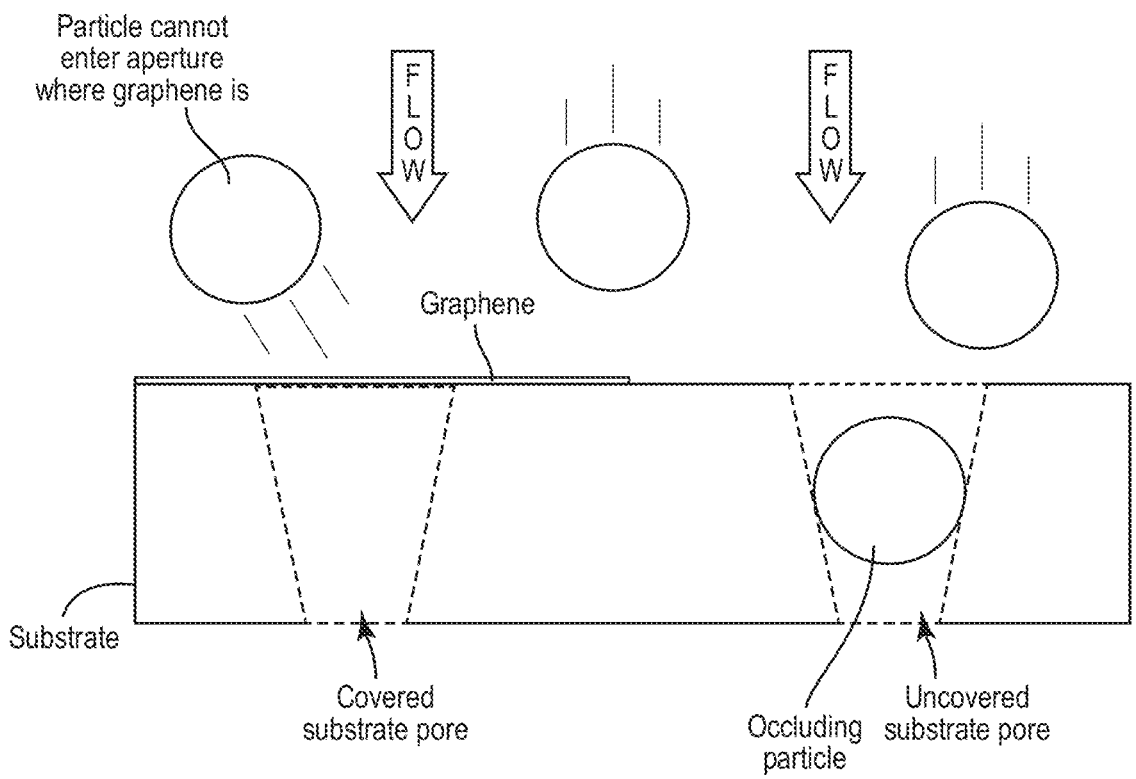
FIG. 7 shows an illustrative schematic demonstrating occlusion of uncovered substrate pores in a composite membrane having a graphene-based material sheet disposed upon a porous substrate according to concepts described herein. In the illustrated embodiment, the substrate pores are tapered to facilitate occlusion and anchoring of the particle in the uncovered pore.

FIG. 7 schematically illustrates an exemplary occlusion method applied to a composite membrane having a graphene-based material sheet disposed upon a porous substrate where the substrate pores of the membrane are tapered such that the pores have a larger cross-section on the side of the substrate exposed to upstream flow to facilitate retention of the occluding material and anchoring of the occluding material in the uncovered pore. This embodiment is exemplified with an occluding particle which is size-selected to enter an uncovered pore and is inhibited or prevented from exiting the pore by tapering of the pore. It will be appreciated the substrate pores can be variously shaped to facilitate retention of occluding moieties, particularly particles. The direction of particle flow is illustrated as perpendicular to the membrane top surface. It will be appreciated that cross-flow parallel to the top surface can be applied to introduce occluding moieties to the top surface.

Figure 8:
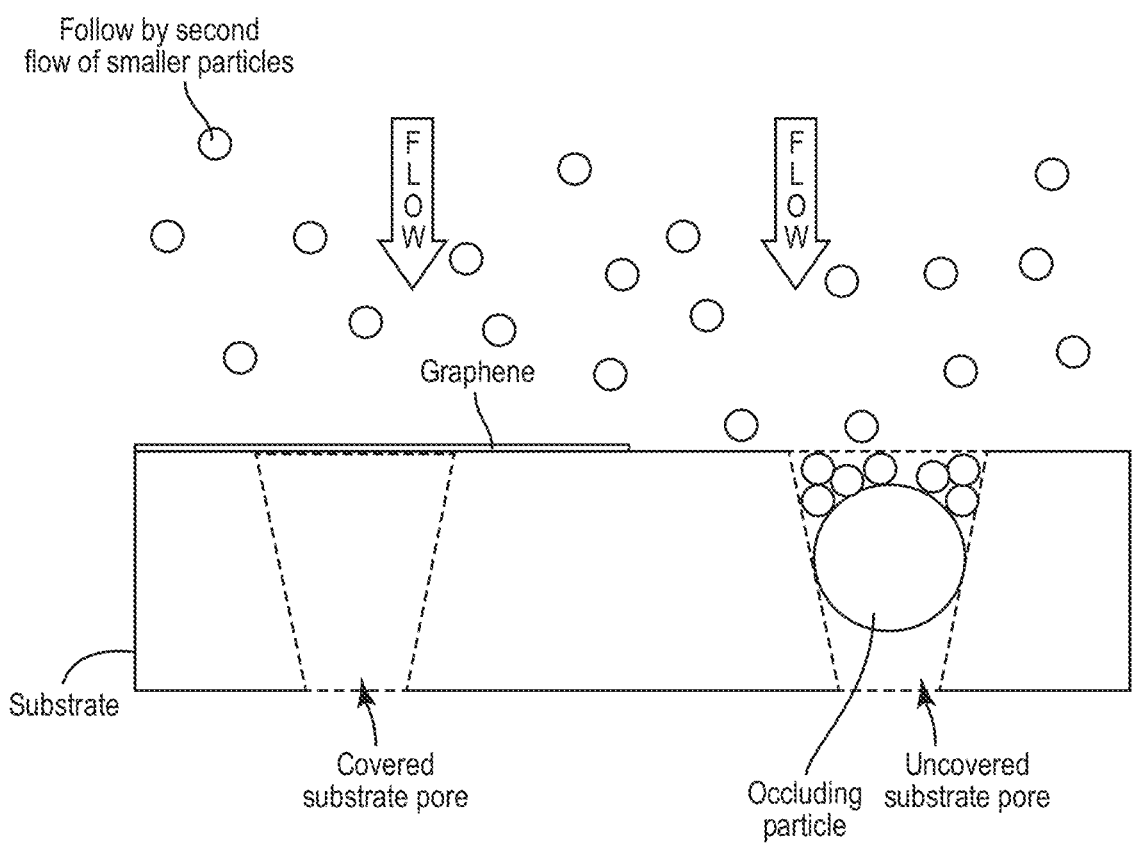
FIG. 8 shows an illustrative schematic demonstrating occlusion of uncovered substrate pores in a composite membrane having a graphene-based material sheet disposed upon a porous substrate according to concepts described herein. The substrate pores are exemplified as tapered. In the illustrated embodiment, an initial particle occludes the pore and secondary particles of size smaller than the initial particle are introduced into the uncovered occluded pores to facilitate anchoring and ensure complete occlusion.

FIG. 8 schematically illustrates another exemplary occlusion method where the composite membrane has a graphene-based material sheet disposed upon a porous substrate where the substrate pores are tapered to facilitate retention of the occluding material and anchoring of the occluding material in the uncovered pore. In the illustrated embodiment, an initial particle is introduced into the uncovered pore to occlude the pore and secondary particles of size smaller than the initial particle are introduced into the uncovered occluded pores to facilitate anchoring.

Figure 9:
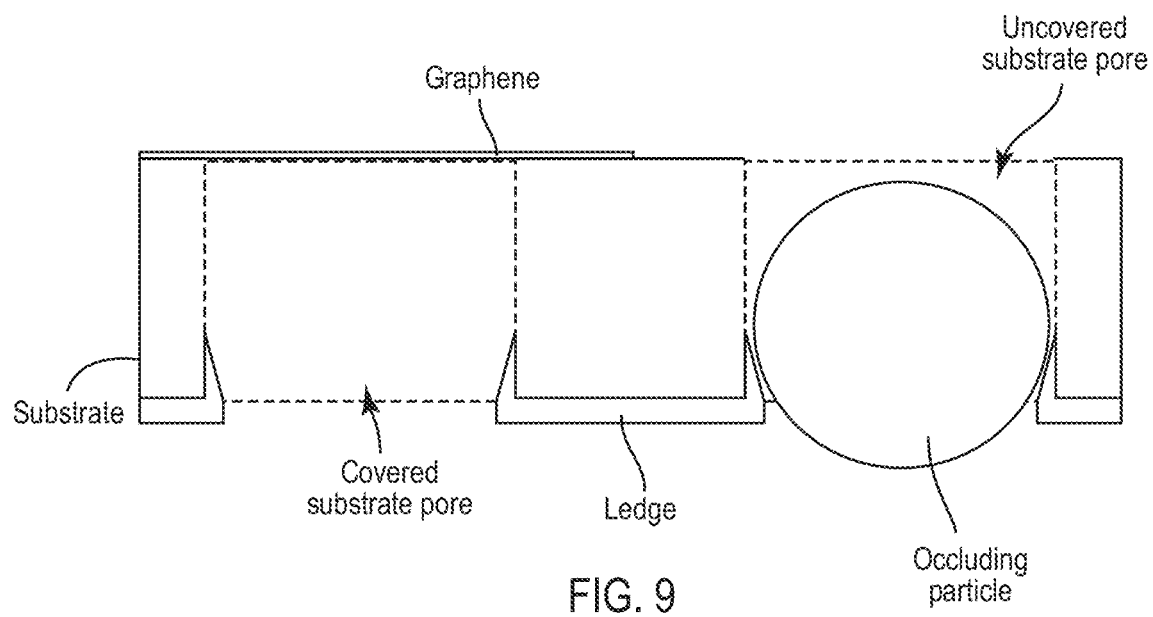
FIG. 9 shows an illustrative schematic demonstrating occlusion of uncovered pores in a composite membrane having a graphene-based material sheet disposed upon a porous substrate according to inventive concepts described herein. The substrate pores are exemplified as having a ledge or other form of narrowing at the pore exit to facilitate retention and anchoring of the particle in the uncovered pore. Such a ledge or other narrowing can for example be formed by deposition of a selected material to the backside of the substrate.

FIG. 9 schematically illustrates another exemplary occlusion method applied to composite membranes having a graphene-based material sheet disposed upon a porous substrate. The substrate pores are exemplified as having a ledge or other form of narrowing along their length and specifically at the pore exit to facilitate retention and anchoring of an occluding moiety (exemplified as a particle) in the uncovered pore.

Figure 10:
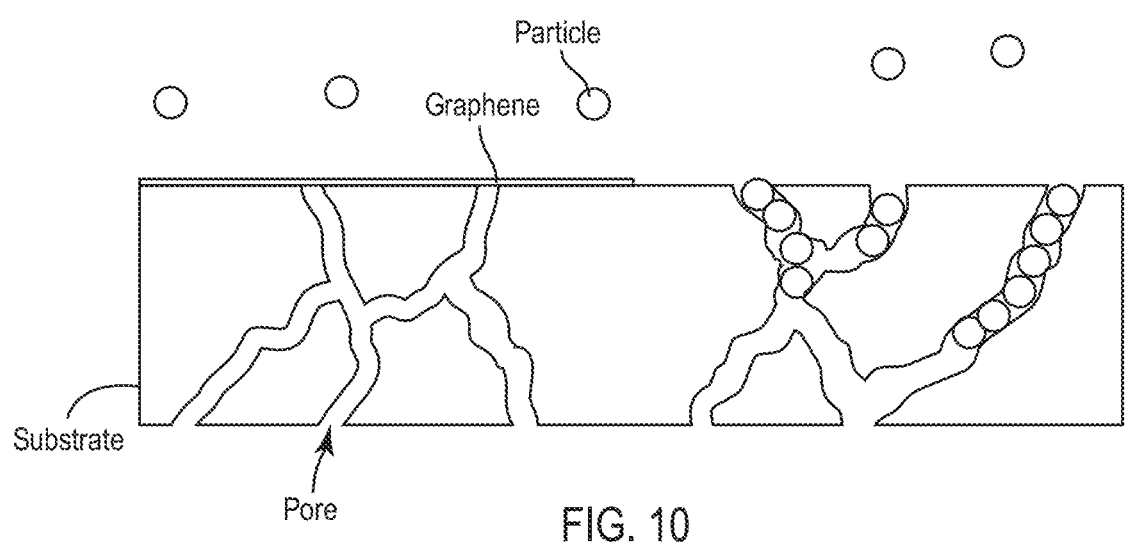
FIG. 10 shows an illustrative schematic demonstrating occlusion of uncovered substrate pores in a composite membrane having a graphene-based material sheet disposed upon a porous substrate according to inventive concepts described herein. Pores in the substrate are illustrated as being interconnecting and non-uniform in diameter. Pores are shown as occluded by introduction of a plurality of particles.

FIG. 10 schematically illustrates another exemplary occlusion of uncovered substrate pores in a composite membrane having a graphene-based material sheet disposed upon the porous substrate. Pores in the substrate are illustrated as being partially interconnected and non-uniform in diameter, and may form a tortuous path through the substrate. Pores are shown as occluded by introduction of a plurality of particles. It is to be noted that if pore connections exist between covered and uncovered pores that occlusion of uncovered pores may reduce desired flow through covered pores.

Figure 11:
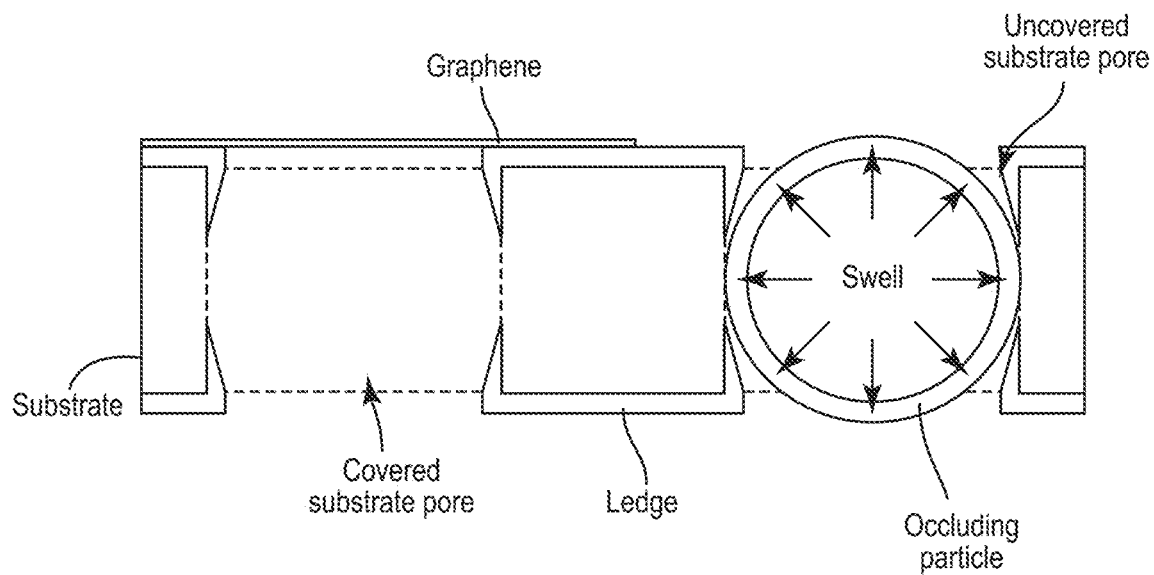
FIG. 11 shows an illustrative schematic demonstrating occlusion of uncovered substrate pores in a composite membrane having a graphene-based material sheet disposed upon a porous substrate including swellable particles according to inventive concepts described herein.

FIG. 11 schematically illustrates another exemplary occlusion of uncovered pores in a composite membrane having a graphene-based material sheet disposed upon a porous substrate. The substrate pores are illustrated as having a ledge or other form of narrowing at both the entrance and exit from the pores. In the illustrated embodiment, the particle is swellable, such that the non-swollen particle is of a size that will enter the uncovered pore, but which on swelling is of a size that will not exit the uncovered pore. In specific embodiments, the swellable particle is composed at least in part of a swellable polymer. More specifically, the swellable particle is composed at least in part of a swellable amorphous polymer. In specific embodiments, the swellable particle is composed at least in part of a hydrogel. Swelling ratios of swellable polymers and hydrogel can be adjusted by variation of composition of the polymer or hydrogel as is known in the art. Swelling can for example be initiated on contact with an absorbable fluid, such as water or an organic solvent. For example, a hydrogel can be swollen employing absorption of water or aqueous solution. For example, a non-polar or hydrophobic polymer can be swollen with a hydrocarbon solvent. For example, a polar or hydrophilic polymer can be swollen with water or alcohol or mixtures thereof.

In embodiments illustrated in FIGS. 6-11, occluding particles can optionally be provided with one or more reactive groups as discussed above which can react or can be activated to react with compatible chemical moieties in the pores, at the edges of the pores, at the substrate surface at the pore opening or pore exit or disposed on ledges or other structures within the pores. Such chemical reactions facilitate anchoring of the particle in the pore. In an embodiment, occluding particles can be provided with compatible reactive chemical groups for reactions between particles in a pore.

Figure 12:
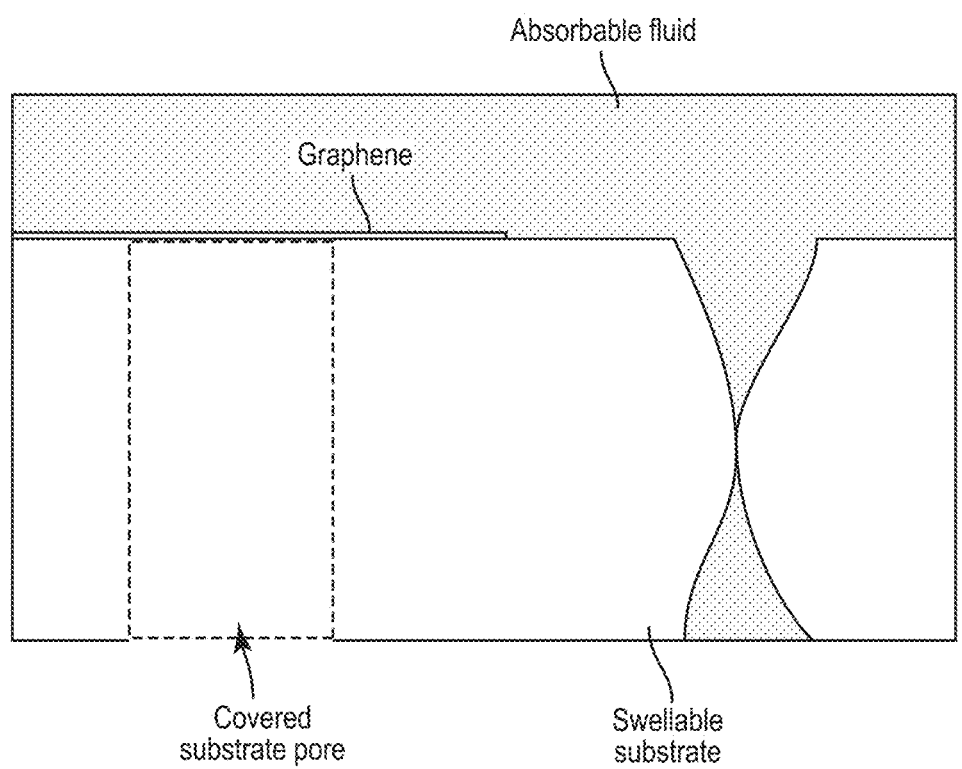
FIG. 12 shows an illustrative schematic demonstrating occlusion of uncovered substrate pores in a composite membrane having a graphene-based material sheet disposed upon a porous substrate according to inventive concepts described herein. In the illustrated embodiment, no occluding moiety needs to be introduced into the uncovered pore. The substrate material itself is swellable, on contact for example with an absorbable fluid. Swelling of the substrate material surrounding the uncovered pore results in occlusion of the pore.

FIG. 12 schematically illustrates another exemplary occlusion of uncovered pores in a composite membrane having a graphene-based material sheet disposed upon a porous substrate. In the illustrated embodiment, no occluding moiety is introduced into the uncovered pore. The substrate material itself is swellable, on contact for example with an absorbable fluid. Swelling of the substrate material surrounding the uncovered pore results in occlusion of the pore. In a related embodiment, the substrate is not made entirely of a swellable material, but the inside surface of the pores of the substrate are provided with a coating that is swellable.

Figure 13:
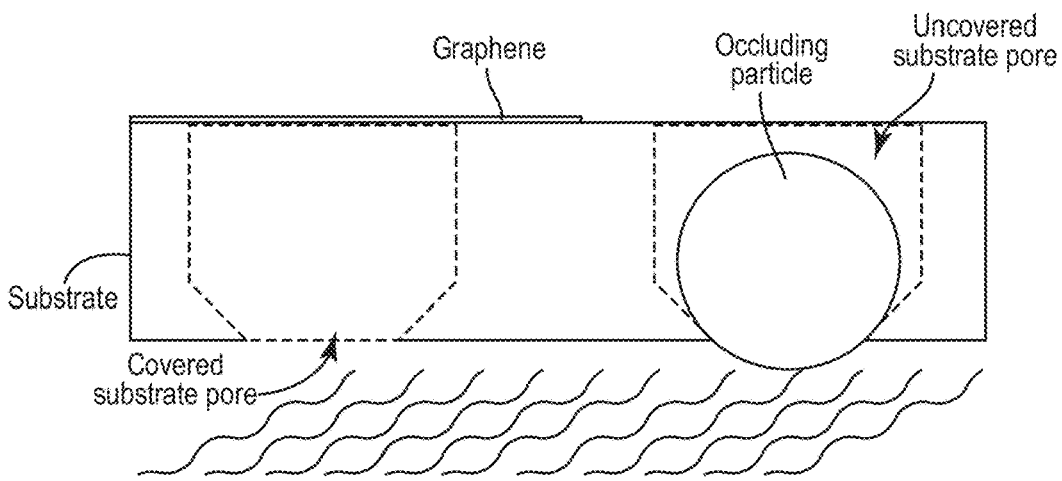
FIG. 13 shows an illustrative schematic demonstrating occlusion of uncovered substrate pores in a composite membrane having a graphene-based material sheet disposed upon a porous substrate including an appropriate chemical reagent applied to initiate reaction between reactive groups on a particle and at a pore exit according to inventive concepts described herein.

FIG. 13 schematically illustrates another exemplary occlusion of uncovered pores in a composite membrane having a graphene-based material sheet disposed upon a surface of a porous substrate. In the illustrated embodiment, the substrate pore is shown as having a narrowing of the pore diameter at the pore exit. In the illustrated embodiment, a chemical reaction is activated to anchor the particle at the pore exit. Activation in this case is introduced to the surface of the membrane without the graphene-based material (also designated the backside of the membrane). A chemical reaction can be activated variously, by providing a reagent or catalyst or by providing activating energy, such as heat, light or activating ions or particles. The angled lines indicate at least for application of electromagnetic radiation or beams of electrons, ions or the like, that irradiation or bombardment can be applied at an angle with respect to the surface such that only a portion of the length of the pore is contacted. For example, an appropriate chemical reagent is applied as illustrated to initiate reaction between reactive groups on the particle and at the pore exit.

Figure 14A:
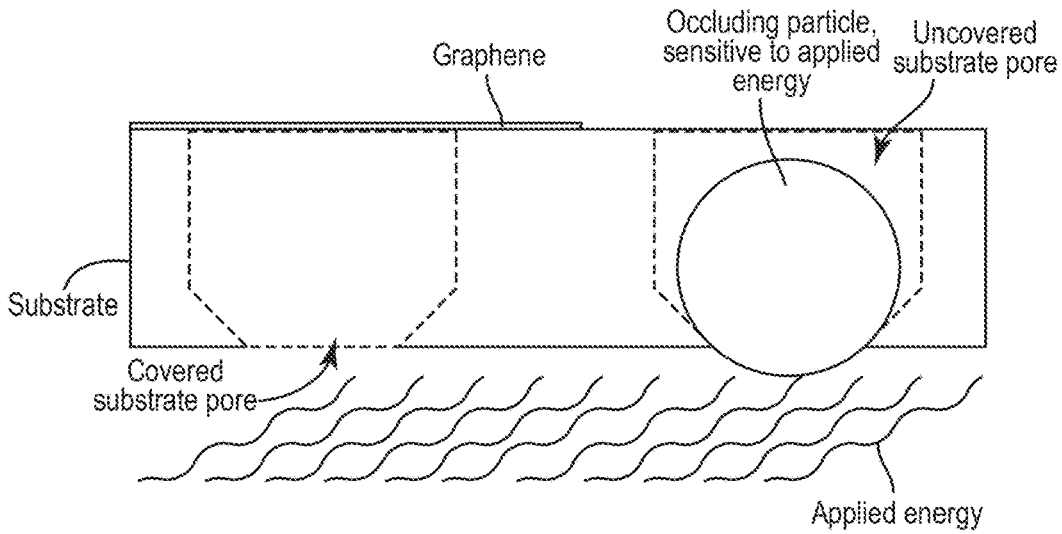
FIGS. 14A and 14B show an illustrative schematic demonstrating occlusion of uncovered pores in a composite membrane having a graphene-based material sheet disposed upon a porous substrate wherein energy, such as light of selected wavelengths is applied to the back side of the composite membrane to facilitate anchoring of the particle in the uncovered pore according to inventive concepts described herein.
Figure 14B:
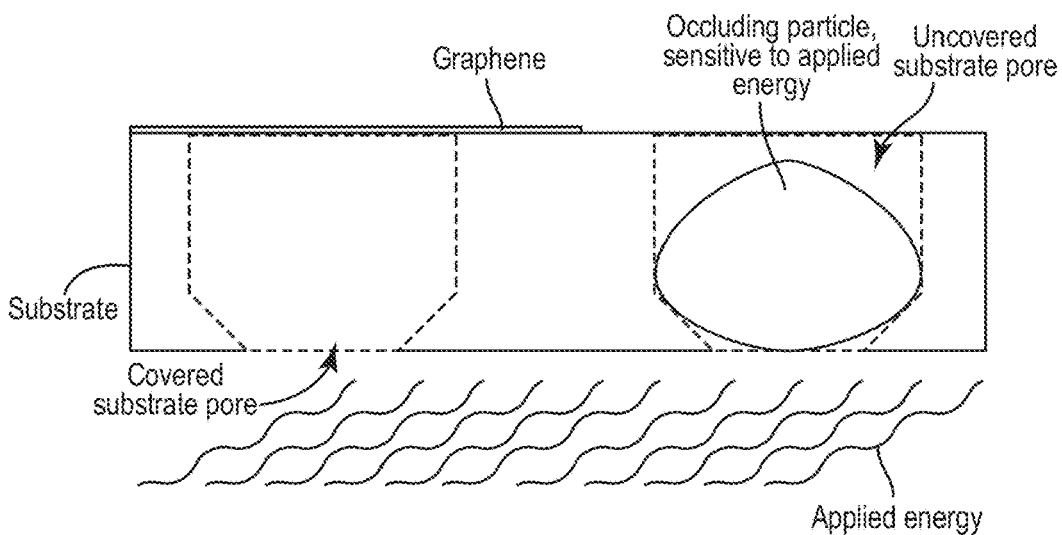

FIGS. 14A and 14B schematically illustrates another exemplary occlusion of uncovered pores in a composite membrane having a graphene-based material sheet disposed upon a porous substrate. In the illustrated embodiment, the substrate pore is shown in FIGS. 14A and B as having a narrowing of the pore diameter at the pore exit. In the illustrated embodiment, after introduction of the particle into the pore energy is applied to the back side of the membrane as shown to cause a change to the occluding particle, such as deformation as shown in FIG. 14B. The occluding particle may be sensitive to applied energy, such as light of selected wavelengths, or contact with electron or ion beams. The applied energy facilitates deformation of the particle in the uncovered pore facilitating anchoring of the particle in the pore.

Figure 15A:
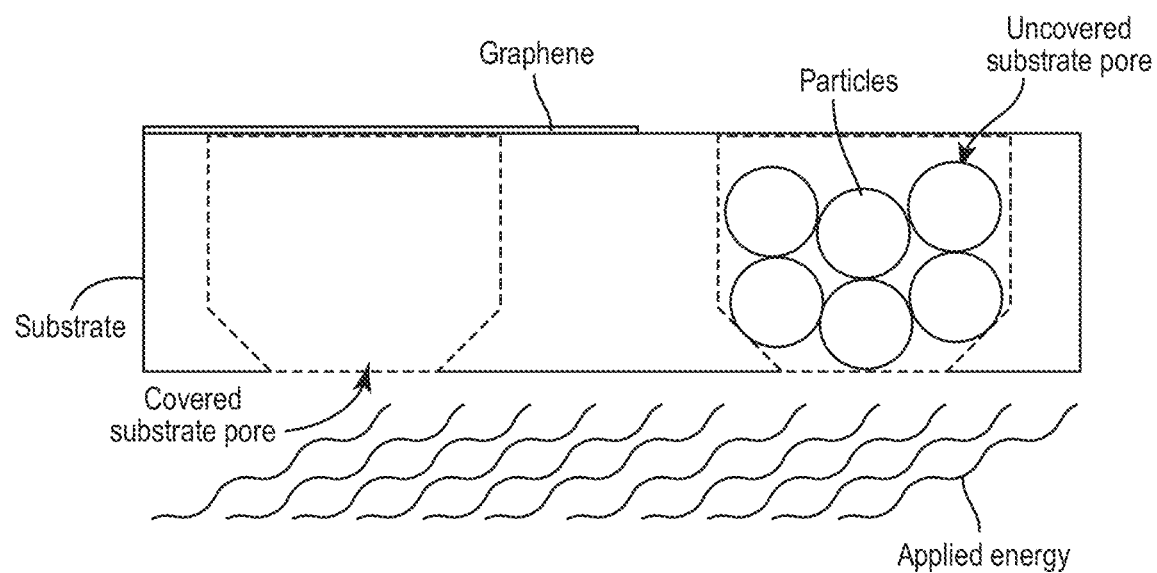
FIGS. 15A and 15B show an illustrative schematic demonstrating occlusion of uncovered pores in a composite membrane having a graphene-based material sheet disposed upon a porous substrate wherein energy is applied to the back side of the composite membrane to deform and conglomerate or active chemical reactions between particles and/or between particles and the pores surfaces or edges to facilitate anchoring of particle in the uncovered pore according to inventive concepts described herein.
Figure 15B:
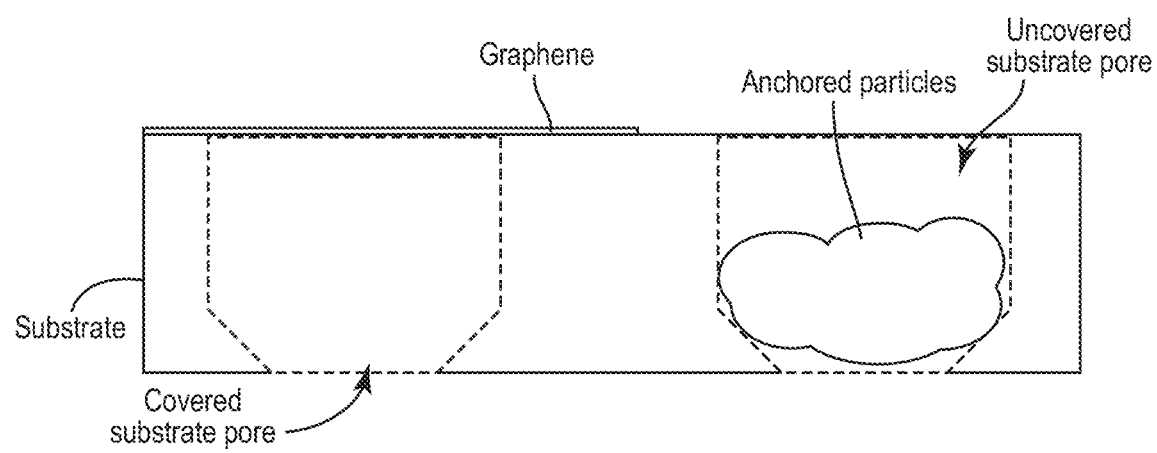
Figure 16:
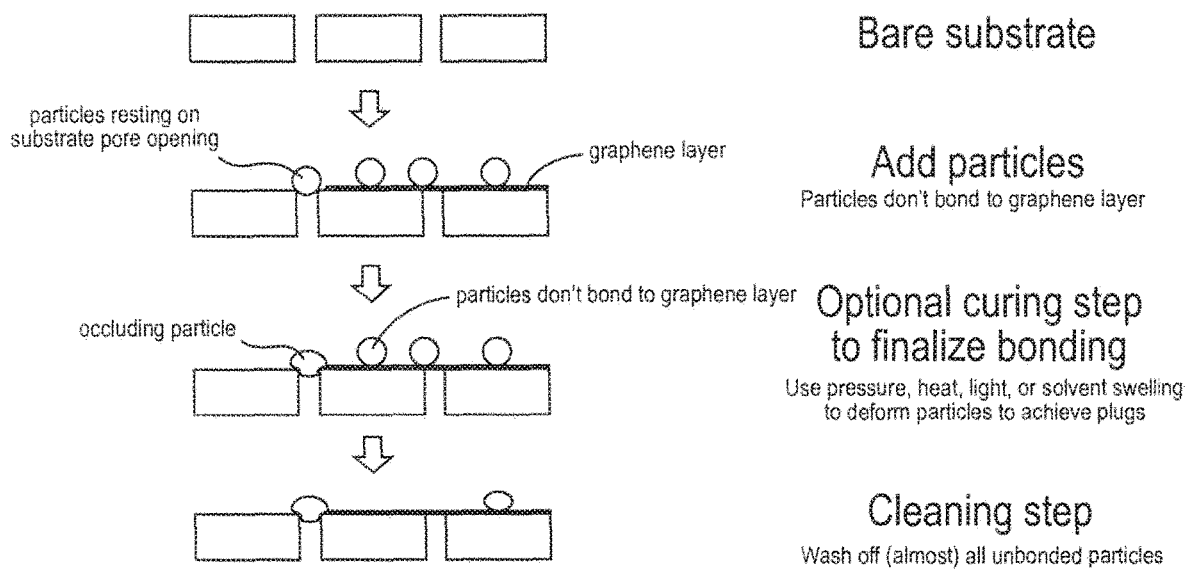
FIG. 16 shows an illustrative schematic showing steps in an exemplary uncovered pore occlusion process according to inventive concepts described herein.

FIGS. 15A and B schematically illustrate another exemplary occlusion of uncovered pores in a composite membrane having a graphene-based material sheet disposed upon a porous substrate. In the illustrated embodiment, the substrate pore is shown as having a narrowing of the pore diameter at the pore exit. In the illustrated embodiment of FIG. 15A, a plurality of particles is shown as introduced into the uncovered pore. In the illustrated embodiment, the particles and/or the pore surfaces or edges carry reactive chemical groups. In the illustrated embodiment of FIG. 15A, energy, for example in the form of light of selected wavelength, an electron or ion beam, or a chemical reagent is applied to the bottom side of the composite membrane to activate chemical reactions between particles and/or between particles and the pores surfaces or edges to facilitate anchoring of particle in the uncovered pore. The result of application of energy is shown in FIG. 15B where the particles are anchored in the substrate pore FIG. 16 schematically illustrates steps in an exemplary uncovered pore occlusion process. A graphene sheet is disposed on a porous substrate, illustrated with uniform pores, to form a composite membrane. A portion of the pores are covered by the graphene and a portion of the pores are not covered by the graphene (uncovered pores). Particles sized to at least partially enter an uncovered pore are introduced to the top surface of the composite membrane where they enter uncovered pores, but not covered pores. In the illustrated embodiment, pressure, heat, or light or alternatively solvent swelling is applied to the particles in the uncovered pores to deform the particles or swell the particles to occlude the pores. Particles do not bond to the graphene. The particles are optionally subjected to an optional curing step after deformation. The curing step is for example a thermoset cure achieved by heating. An alternative exemplary cure is achieved catalytically by exposure to a catalyst or curing agent. A cleaning step is then applied to wash off and remove excess particles. The steps of introducing the particles, application of pressure, energy or solvent swelling, and cleaning are repeated until a desired level of pore occlusion is obtained.

Figure 17:
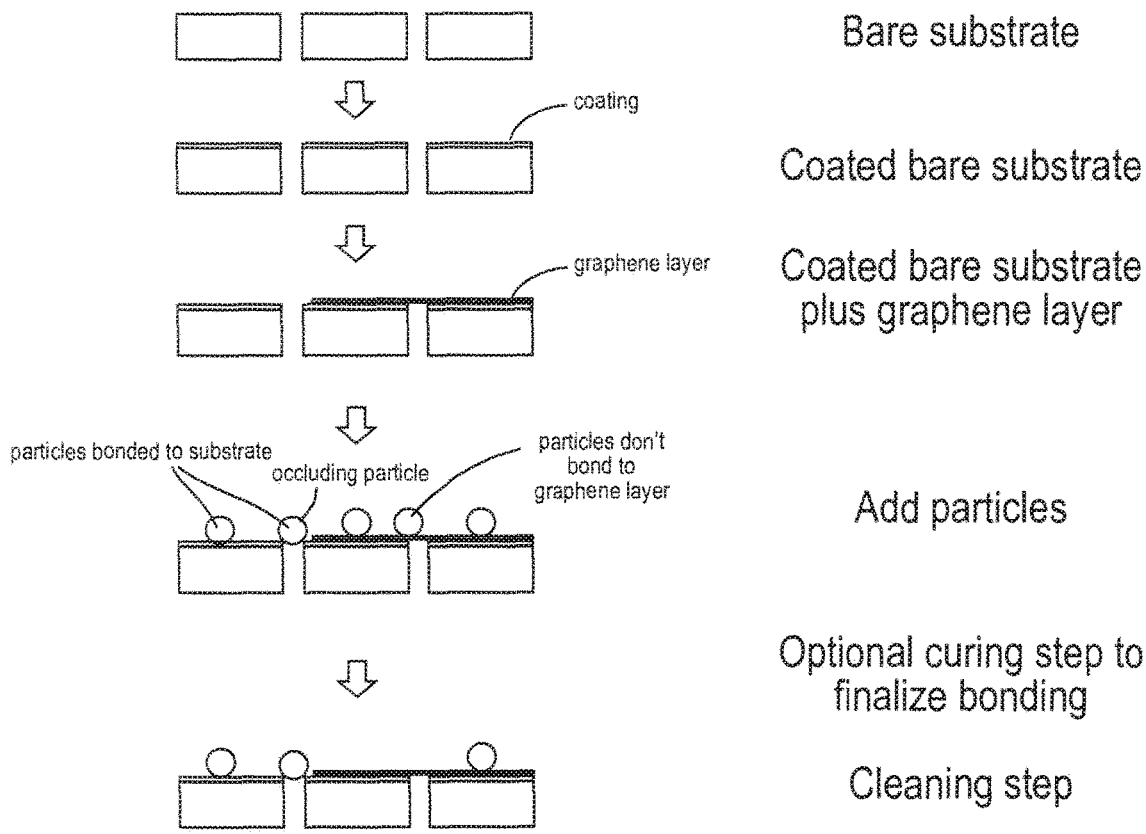
FIG. 17 shows an illustrative schematic showing steps in another exemplary uncovered pore occlusion process according to inventive concepts described herein.

FIG. 17 schematically illustrates steps in an exemplary uncovered pore occlusion process. A porous substrate is provided with a coating which is compatible with graphene and may enhance adhesion to graphene. The coating provided does not occlude substrate pores. A graphene sheet is then disposed on the coated porous substrate, illustrated with uniform pores to form a composite membrane. A portion of the pores are covered by the graphene and a portion of the pores are not covered by the graphene (uncovered pores). Particles sized to at least partially enter an uncovered pores are introduced to the top surface of the composite member where they enter uncovered pores, but not covered pores. In the illustrated embodiment, particles optionally bond to the substrate or to the coating on the substrate to facilitate anchoring of the particles to occlude uncovered pores. Particles do not bond to the graphene. The particles may be subjected to an optional curing step after bonding. A cleaning step is then applied to wash off and remove excess particles. The steps of introducing the particles, bonding and optionally curing of particles, and cleaning are repeated until a desired level of pore occlusion is obtained.

Figure 18:
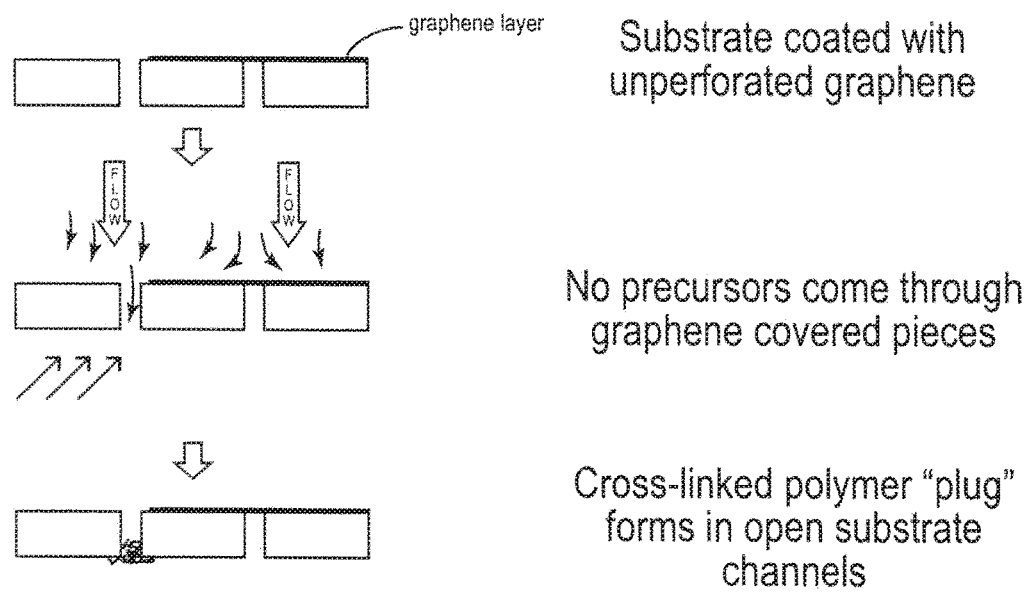
FIG. 18 shows an illustrative schematic showing steps in another exemplary uncovered pore occlusion process according to inventive concepts described herein.

FIG. 18 schematically illustrates steps in an exemplary uncovered pore occlusion process. A graphene sheet is disposed on a porous substrate, illustrated with uniform pores to form a composite membrane. A portion of the pores are covered with the graphene and a portion of the pores are not covered by the graphene (uncovered pores). Polymerizable monomers or oligomers or a curable or cross-linkable polymer are introduced into the uncovered pores. These precursors do not enter graphene covered pores. The precursors are polymerized, cured or cross-linked within the uncovered pores to occlude the pores. Polymerization or curing can be facilitated by application of heat, light of selected wavelength or of chemical reagents including polymerization catalyst and/or cross-linking agents. A cleaning step is then applied to wash off and remove excess unreacted precursors and any catalysts or reagents employed. The steps of introducing precursors for polymerization, curing or cross-linking, polymerization, curing and/or cross linking and cleaning are repeated until a desired level of pore occlusion is obtained.

Figure 19:
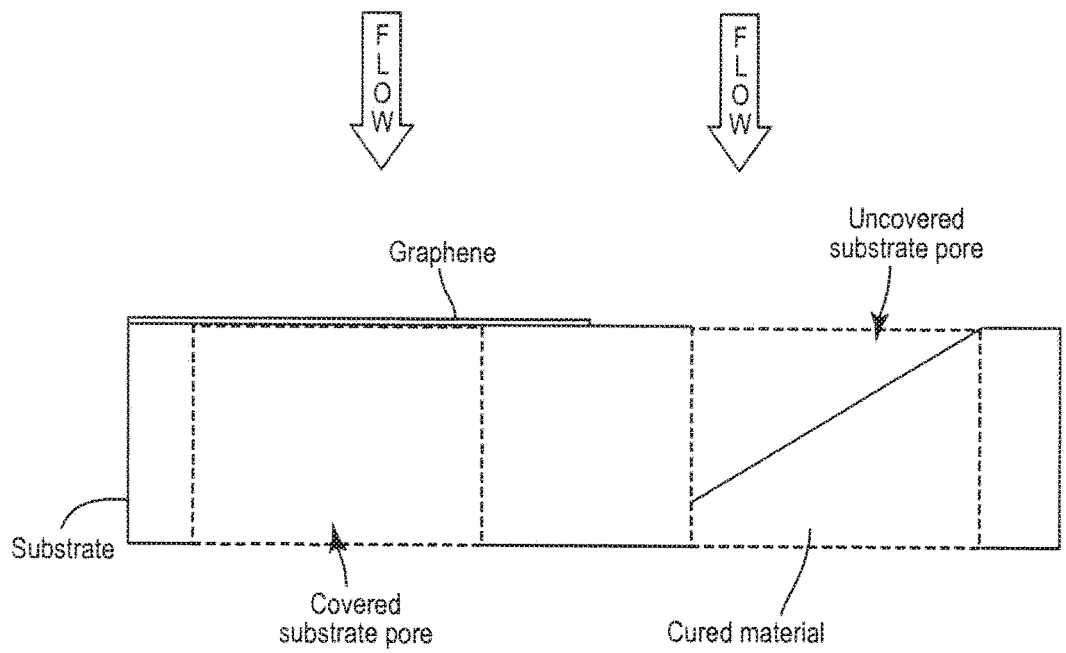
FIG. 19 is an illustrative schematic demonstrating occlusion of uncovered pores by the process of FIG. 18 according to inventive concepts described herein. In the illustrated embodiment, the substrate pore is illustrated as having uniform diameter along its length. Shaped pores can also be employed. The illustrated embodiment shows the formation of a cured material or polymer within the uncovered pore to occlude the pore.

FIG. 19 schematically illustrates exemplary results of occlusion of uncovered pores as in the process of FIG. 18. In the illustrated embodiment, the substrate pores are shown as having uniform diameter along their length. Shaped pores can also be employed. The illustrated embodiment shows the formation of a cured material or polymer within the uncovered pore to occlude the pore. The direction of flow for introduction of occluding moieties is illustrated as flow perpendicular to the substrate top surface. It will be appreciated that flow can also be applied in the illustrated embodiments in a cross-flow configuration, where flow is parallel to the substrate top surface.

Figure 20A:
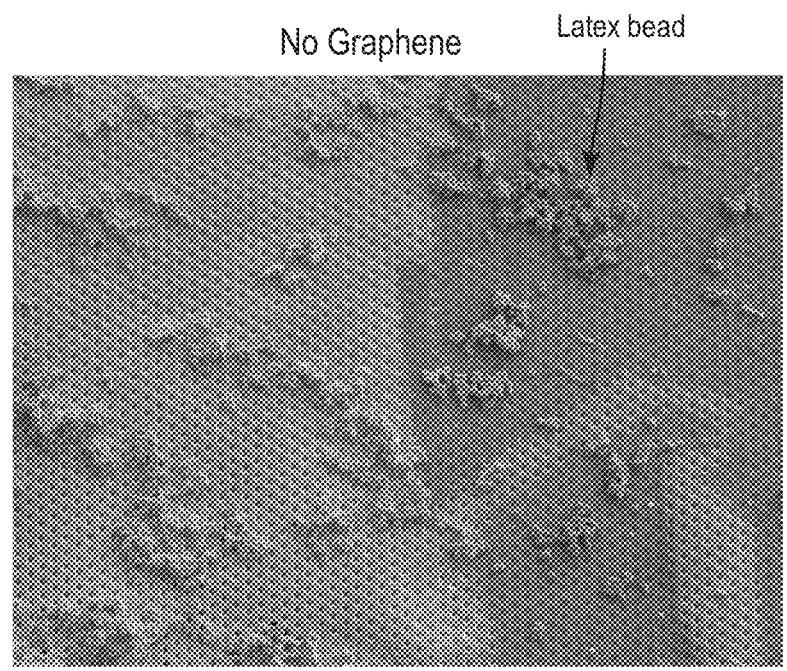
FIGS. 20A and 20B are SEM images illustrating latex bead healing (occlusion) of uncovered pores in a composite membrane according to inventive concepts described herein.
Figure 20B:
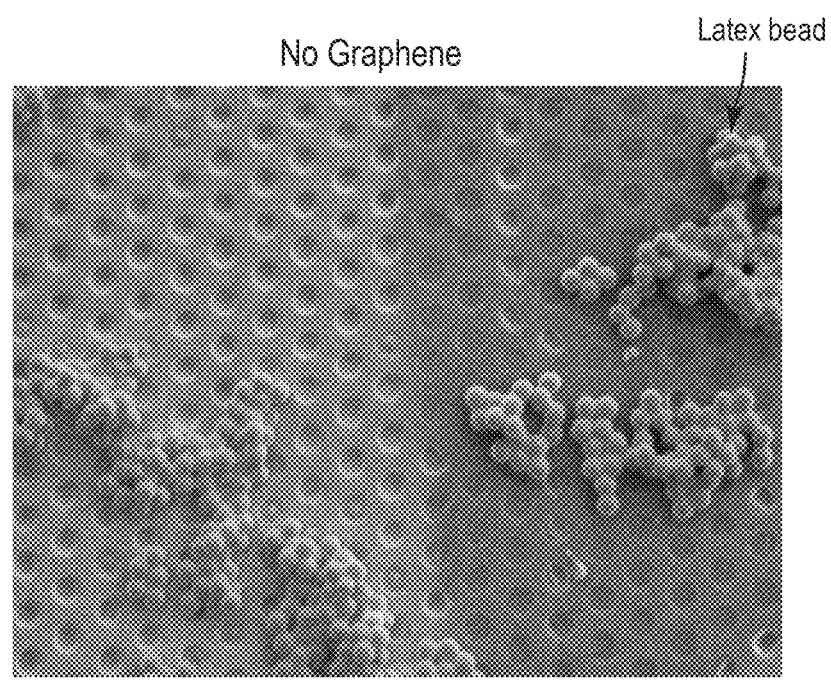
Figure 21A:
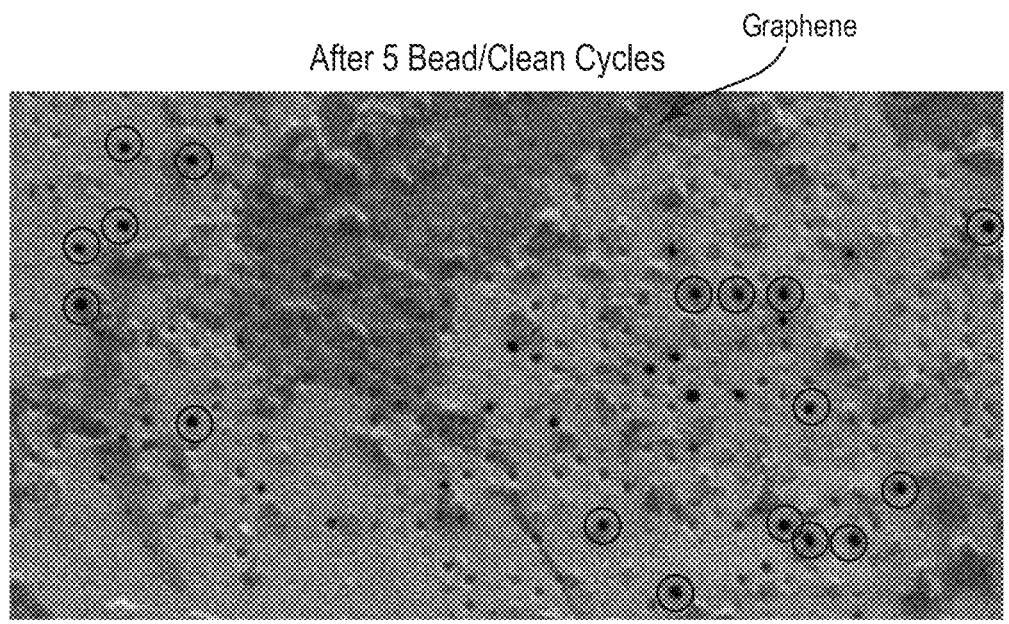
FIGS. 21A and 21B are SEM images illustrating the progress of latex bead healing (occlusion) of uncovered pores in a composite membrane according to inventive concepts described herein.
Figure 21B:
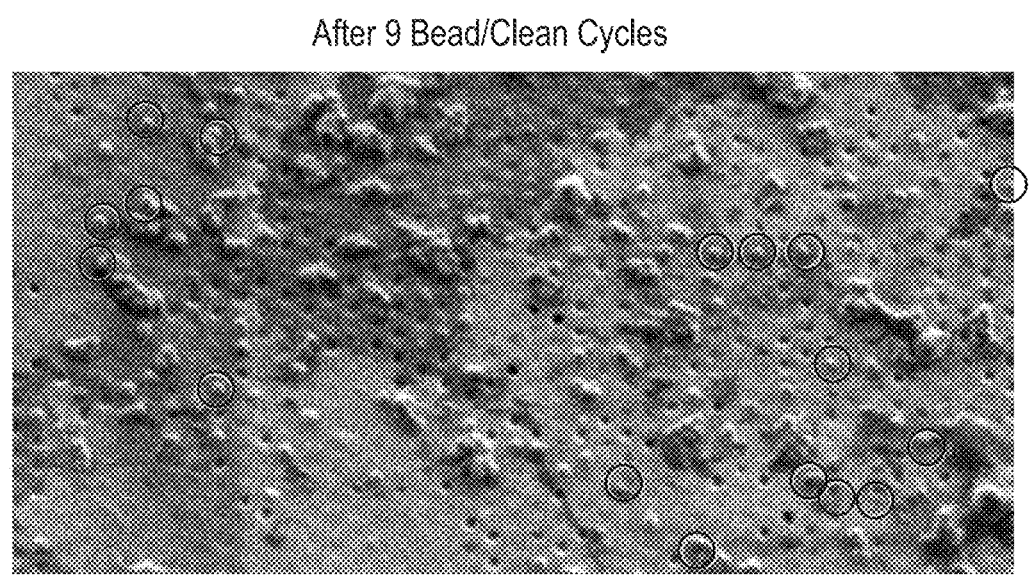

FIGS. 20A and 20B are scanning electron microscopy (SEM) images illustrating latex bead healing (occlusion) of uncovered pores in a composite membrane. The SEM images were taken while tilted at 35-degrees relative to normal of the substrate surface. Areas covered in graphene are dark gray and areas without graphene coverage are light gray. FIG. 21A is a lower magnification (×2500) SEM image showing areas on the composite membrane that are covered or not covered by graphene. Substrate pores (450 nm diameter) which are uncovered by graphene are being occluded by latex beads. Latex beads are also shown clumping on the surface of the composite membrane. Latex beads do not damage the graphene. Pores in the substrate that are uncovered by graphene are being occluded by the latex beads. FIG. 21B is a higher magnification SEM image (×8500) of the same composite membrane showing latex beads occluding uncovered pores in the substrate. Those latex beads which are occluding substrate pores are visible embedded at varying depths into the substrate pores.

FIGS. 21A and 21B are SEM images illustrating the progress of latex bead healing (occlusion) of uncovered pores in a composite membrane. Latex beads of particle size 0.46 μm were employed to occlude substrate pores of 0.45 μm. The graphene sheet is light gray and a large area of dark gray is a microdefect in the graphene. A number of apertures in the graphene are circled in the images. FIG. 21A is an image taken after 5 cycles of alternating latex bead introduction and cleaning, both via cross-flow across the membrane surface. Latex beads were introduced at a 1 ppm dilution in DI water containing 0.1% polysorbate-80 and a biocide (50 ppm NaI3). Cleaning cycles were performed with the same solution sans latex beads. A three-port flow apparatus with input and output ports allowed for flow across the surface of the graphene-coated surface of composite membrane plus "permeate" flow through membrane. Most uncovered pores are occluded after 5 cycles of alternating latex bead introduction and cleaning, but the circled pores are not occluded. FIG. 21B is an image taken after another 4 of alternating latex bead introduction and cleaning (a total of 9 cycles). Additional apertures are occluded in this second image including all of the apertures circled in the image. The occlusion process illustrated in these images was found however not to be optimized. In particular, it was found that variation of the concentration of the occluding particles in the flow introduced to the membrane could affect efficiency of the occlusion process. It was also found that addition of a surfactant with the flow of particles reduced aggregation and clumping of particles. Clumping of particles on the membrane top surface is preferably minimized or avoided.

Figure 22A:
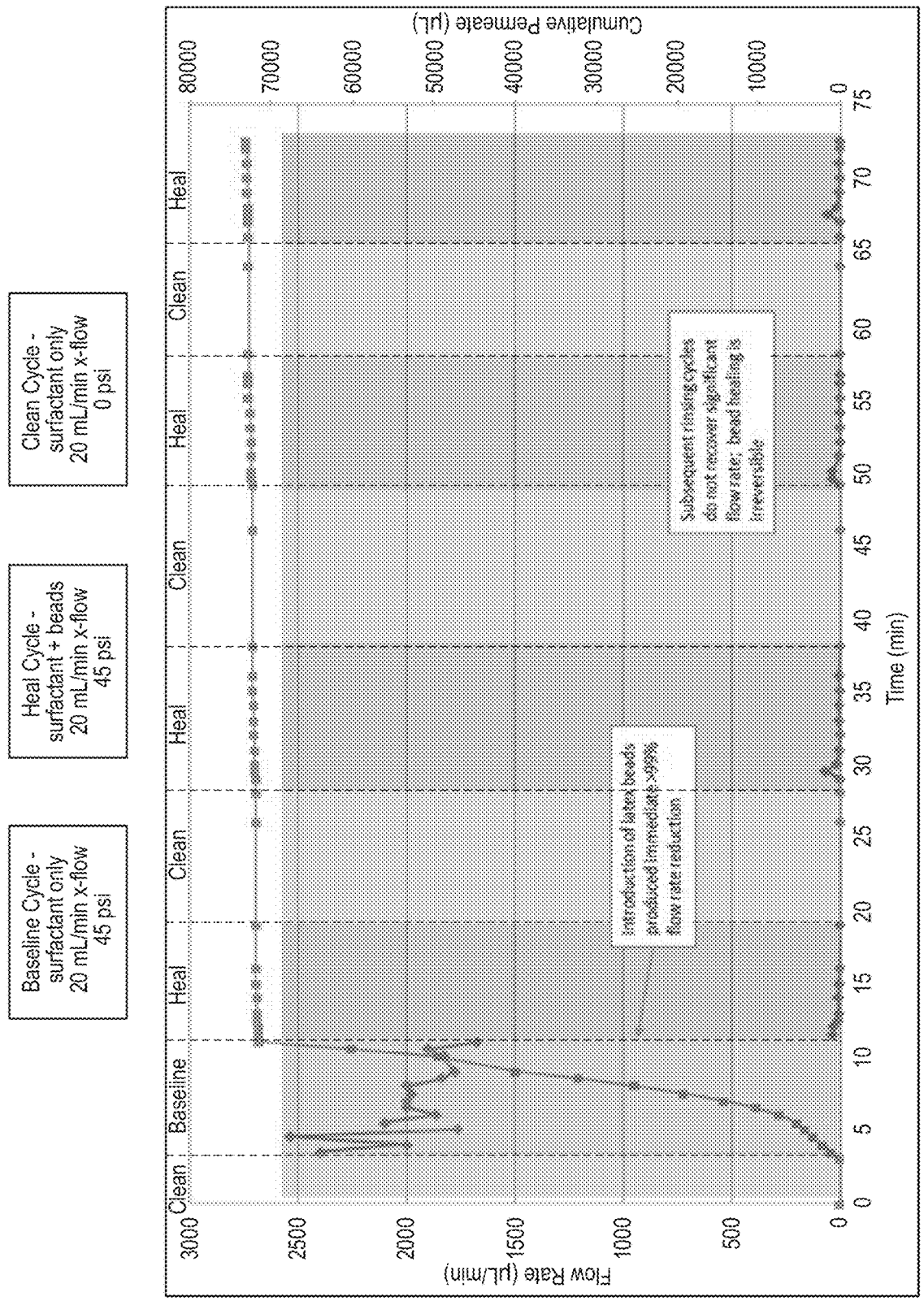
FIG. 22A is a graph of flow rate (µL/min) (left axis, diamonds) and cumulative permeate (right axis, squares) as a function of time through a composite membrane that is being subjected to uncovered substrate pore occlusion according to inventive concepts described herein.
Figures 22B, 22C:
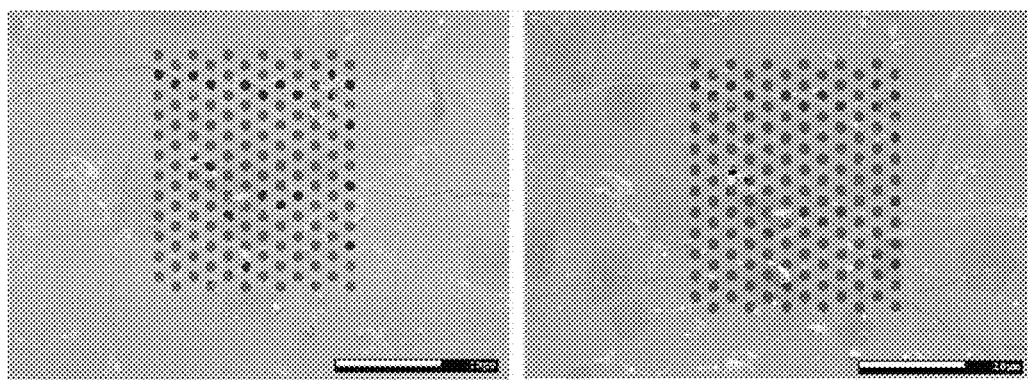
FIG. 22B is a SEM image showing occlusion of 1250 nm diameter pores in a silicon nitride substrate by a single graphene sheet according to inventive concepts described herein.
FIG. 22C is a SEM image of occlusion of 1250 nm diameter pores in a silicon nitride substrate after subsequent application of a second sheet of graphene according to inventive concepts described herein.

FIG. 22B is a SEM image showing occlusion of 1250 nm diameter pores in a silicon nitride substrate by a single graphene sheet, while FIG. 22C is a SEM image of occlusion of 1250 nm diameter pores in a silicon nitride substrate after subsequent application of a second sheet of graphene. As can be seen, a majority of uncovered pores resulting from defects in the first graphene sheet are subsequently occluded by the second graphene sheet. Thus, layering of individual sheets of the two-dimensional material is an effective method for occluding pores in a composite membrane that arise from intrinsic defects and defects generated during the processing and handling of the two-dimensional material. Occlusion of the substrate pores can be significantly improved when subsequent sheets of the two dimensional material are applied, because the intrinsic defects and defects generated during processing and handling are independent for each layer thus the probability of an unoccluded substrate pore is exponentially reduced with each successive layer. Such a method is most effective for fabrication of a size-selective composite membrane when the size-selected perforations are introduced to the multi-layer stack of two-dimensional materials. In some embodiments, the methods described herein for occluding apertures in a sheet of a two-dimensional material may then be beneficially employed to a multi-layer stack of two dimensional materials.

FIG. 22 is a graph of flow rate (μL/min) (left axis, diamonds) and cumulative permeate (right axis, squares) as a function of time through a graphene coated composite membrane that is being subjected to uncovered pore occlusion employing latex particles. The flow rates noted are the cross-membrane (input-to-output) rates, while the pressures noted are the pressure difference between graphene side of membrane and the permeate outlet. The occlusion process employed to obtain the illustrated results differed from that illustrated in FIGS. 21A and 21B, in that the concentration of particles applied to the top surface was optimized to improve efficiency of occlusion. The porous substrate of the composite membrane is etched silicon nitride in a rigid silicon support. The silicon nitride has a plurality of patterned 0.45 μm pores. The composite membrane is assessed in a cross-flow arrangement with pressure applied as indicated. A three-port flow apparatus with input and output ports allowed for flow across the surface of the graphene-coated surface of composite membrane plus "permeate" flow through membrane. A baseline cycle in which an aqueous solution containing only surfactant (0.1% polysorbate-80) with 20 mL/min flow at 45 psi is initially applied. An occlusion cycle includes a step of introduction of latex beads (0.46 µm beads) and a subsequent cleaning step. The latex beads are carried in aqueous solution at a concentration of 0.5 ppm (0.1% polysorbate-80 and biocide (50 ppm NaI3) and introduced in cross-flow to the composite membrane at 20 m/min at 45 psi. The cleaning step is cross-flow application of an aqueous solution containing surfactant at a 20 mL/min flow at 0 psi to remove latex beads remaining on surface. The occlusion step and cleaning step are applied for 7-11 minutes as indicated in FIG. 22. The figure follows flow rate and cumulative permeate for three full occlusion/cleaning cycles. Introduction of latex beads in the first occlusion step is shown to produce an immediate greater than 99% reduction in flow rate. Cleaning steps induce a small flow rate recovery (<5% of the flow rate before occlusion), which is then reversed by subsequent occlusion steps. Similarly, cumulative permeate levels off immediately on introduction of the latex beads. No increase in flow rate or the rate of accumulation of permeate is observed on application of additional occlusion cycles. In an embodiment, the concentration of beads may set according to the desired result. In an embodiment, small beads may be introduced, while larger beads are used to remove the small beads in the cleaning step. In an embodiment where bead agglomeration is not detrimental, the agglomerated beads may provide a filtering function.

Graphene Platelet-Based Polymers and Uses Thereof

Some embodiments provided herein are cross-linked graphene platelet polymers, compositions thereof, filtration devices comprising the cross-linked graphene platelet polymers and/or compositions thereof and methods for using and making the same.

Cross-Linked Graphene Platelet Polymers

Some of the polymers described herein comprise a graphene portion or moiety and a crosslinking portion or moiety.

The graphene portion or moiety may be a graphene platelet that may be chemically bound directly or indirectly to one or more crosslinking portions or moieties. Crosslinking may be by covalent or other bonding mechanism such as ionic, van der Waals, etc.

The graphene portion in some embodiments comprises a reacted graphene platelet.

The graphene platelet may have a very thin but wide aspect ratio. The graphene platelet may comprise several sheets of graphene, for example 1, 2, 3, 4, 5, 6, 7, 8, 9 or 10 sheets of graphene. It is understood that the various sheets are not necessarily the same width, e.g., one or more of the sheets may be a partial sheet that covers only a portion of the sheet in which it is associated with or in contact. For example, a partial sheet may cover about 10%, 20%, 30%, 40%, 50%, 60%, 70%, 80%, 90%, 95%, 98%, 99% of the portion of the sheet in which it is associated with or in contact.

The particle diameter of the graphene platelet may range from sub-micron (for example, about 10 nm, 50 nm, 100 nm, 200 nm, 300 nm, 400 nm, 500 nm, 600 nm, 700 nm, 800 nm, 900 nm, or 1000 nm) up to about 100 microns (for example up to about 1 micron, 2 microns, 3 microns, 4 microns, 5 microns, 6 microns, 7 microns, 8 microns, 9 microns, 10 microns, 20 microns, 30 microns, 40 microns, 50 microns, 60 microns, 70 microns, 80 microns, 90 microns, 100 microns). Various ranges between the disclosed particle diameters may be utilized. It is understood that the graphene platelets will not necessarily be perfect circular particles. Thus, the particle diameter may be measured from the widest points of the graphene platelet.

The size of the graphene platelets may also be expressed as an average size or a plurality of graphene platelets. For example, in some embodiments, the average size of a plurality of graphene platelets used may be about 10 nm, 50 nm, 100 nm, 200 nm, 300 nm, 400 nm, 500 nm, 600 nm, 700 nm, 800 nm, 900 nm, or 1000 nm, about 100 microns (for example up to about 1 micron, 2 microns, 3 microns, 4 microns, 5 microns, 6 microns, 7 microns, 8 microns, 9 microns, 10 microns, 20 microns, 30 microns, 40 microns, 50 microns, 60 microns, 70 microns, 80 microns, 90 microns, 100 microns. The coefficient of variation for the average size may be greater than zero to about 25%. For example, the coefficient of variation may be about 0.01, 0.1, 0.5, 1, 2, 3, 4, 5, 6, 7, 8, 9, 10, 11, 12, 13, 14, 15, 16, 17, 18, 19 or 20.

The graphene platelets in some of the embodiments may be functionalized. This functionalization may result in a direct or indirect chemical bond to the one or more cross-linking portions or moieties, or it may provide additional functionality to the resulting cross-linked graphene platelet polymer.

In some embodiments, the graphene platelet comprises one or more reactive moieties capable of reacting with a crosslinking molecule. In some embodiments, the graphene platelet is functionalized as disclosed in Hunt, A., et al. Adv. Funct. Mater., 22(18), pp. 3950-3957, 2012. The one or more reactive moieties, for example, may be capable of reacting with a (meth)acrylate or (meth)acrylamide moiety, or may be capable of reacting, e.g., with a hydroxyl moiety, a carbonyl moiety, an epoxy moiety, an ether linkage, and phosphide, phosphate, sulfide and/or a sulfate. In some embodiments, the one or more reactive moieties of the graphene platelet can be an epoxy functional group or amine, and graphene/carbon nitride via reaction in a nitrogen plasma. In some embodiments, the one or more reactive moieties is a "capped" moiety that is capable of converting to a reactive moiety upon, e.g., chemical, heat or UV treatment. In various embodiments the graphene has a variable C/O ratio that maximizes the mechanical strength, and the variation is C/O ratio of 2/1, 5/1, 10/1, 20/1, 30/1, 40/1, 50/1, 60/1 70/1, 80/1 90/1, and 100/1. The speciation of the graphene would be either hydroxyl or epoxy, when reactions with amines or cyanates, can form one pot epoxy or urethane networks. In some embodiments, the one or more reactive moieties are a "capped" moiety that is capable of converting to a reactive moiety upon, e.g., chemical, heat or UV treatment. In some embodiments, the graphene platelet may comprise 1, 2, 3, 4, 5, 6, 7, 8, 9 or 10 reactive moieties. In some embodiments, a plurality of graphene platelets used in the polymer may have an average of about 2, 3, 4, 5, 6, 7, 8, 9 or 10 reactive moieties. The coefficient of variation for this average may be greater than zero to about 25%. For example, the coefficient of variation may be about 0.01, 0.1, 0.5, 1, 2, 3, 4, 5, 6, 7, 8, 9, 10, 11, 12, 13, 14, 15, 16, 17, 18, 19 or 20.

In some embodiments, the graphene platelet comprises one or more functional moieties. These moieties are different from the reactive moieties in that they do not react with the crosslinking molecule, but rather they ultimately impart some functionalization to the resulting cross-linked graphene platelet polymer. Some embodiments utilize functional moieties including thiol moieties, fluorocarbon functionalized areas of the graphene platelet and/or phosphorus, silane and siloxane functional groups.

The crosslinking portions or moieties in some embodiments may be a crosslinking portion that is chemically bound directly or indirectly to two or more graphene portions or moieties. The cross-linked graphene may form ordered layers wherein the crosslinking moiety controls the spacing between ordered layers.

In some embodiments, the crosslinking portion comprises a reacted di-, tri- or tetra-functional crosslinking compound. The functional group may be a (meth)acrylate or (meth)acrylamide moiety, or may be capable of reacting with a hydroxyl or epoxy moiety. In some embodiments, the di-, tri- or tetra-functional crosslinking compound contains the same functional groups. In other embodiments, the functional groups on the di-, tri- or tetra-functional crosslinking compound are different. The crosslinking compound also includes a spacer portion between the functional groups. The spacer group remains in the crosslinking portions or moieties after the functional groups have reacted. For example, the spacer group may comprise 1 to 10 atoms in a linear chain, for example, carbon, oxygen or sulfur atoms, phosphide, phosphate or inorganic moieties as well, silicon and transition metals. The length of the spacer groups will determine the class of the filtered species. The spacer group between adjacent or laterally stacked graphene platelets of 1 to 6 carbons, with a carbon-carbon single bond of 1.54 Å, allows for selectivity of ionic filtration, for species up to 1 nm in diameter. Longer spacers, or branching can enable selectivity for viruses and other pathogens. For example, the spacer may be longer, but still provide spacing between graphene platelets that allows for selective size exclusion of certain viruses and other pathogens of a particular size. The spacing may be determined based on the desired viruses and other pathogen that should be excluded. In some embodiments, the spacer group is a C1-C10 linear chain, or a C3-C20 branched chain. One or more of the carbons may be replaced by an oxygen and/or sulfur atom. The C1-C10 linear chain or C3-C20 branched chain may comprise methylene groups, which may be optionally substituted with one or more halogen of hydroxyl group thiol groups, phosphate, or phosphide.

The crosslinking portions or moieties of some embodiments provide a spacing between two or more graphene portions or moieties. In some embodiments, the crosslinking portion or moiety provides a 4 to 10 atom link between two or more graphene portions or moieties. In other embodiments, the cross-linking portion provides a 4 to 10 atom link between two or more graphene portions or moieties provide a spacing between individual graphene platelet moieties of about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, or 3.5 nm. The spacing between individual graphene platelet moieties may be determined by molecular modeling of the reacted cross-linking portion, or by microscopic methods, electroacoustic spectroscopy to measure particle and spacing size in aqueous media as well as the zeta potential of the surfaces. Also, x-ray diffraction may be employed to measure inter-plate gallery spacing in lamellar structures. Methods to control the spacing between vertically stacked graphene platelets can employ flexible, e.g., polyphenylene oxide repeat units or rigid carbon spacers with, e.g., polyphenylene or polynorbornene rods to provide a consistent spacer between graphene plates.

In other embodiments, the crosslinking portions or moieties of some embodiments can include spacer moieties. For example, the crosslinking portion may include moieties to attach to the graphene platelets (e.g., covalently, ionically, etc.) and the spacer moiety. Spacer substances can include polymers, fibers, hydrogels, molecules, nanostructures, nanoparticles and allotropes that are responsive to an environmental stimulus. In some embodiments, the spacer substance is a smart polymer, such as a hygroscopic polymer; a thin polymer that expands when hydrated; or an amorphous polymer, such as a porous amorphous polymer. In some embodiments, the spacer substance comprises electrospun fibers that can be swelled upon exposure to a solvent. In some embodiments the spacer substance comprises materials with a high thermal expansion coefficient, which expand or contract in response to a temperature stimulus. In some embodiments, the spacer substance is deliquescent. In some embodiments, the spacers are substantially inert. In some embodiments, the spacers are not inert (i.e., they can be reactive).

Exemplary spacer substances also include structural proteins, collagen, keratin, aromatic amino acids, and polyethylene glycol. Such spacer substances can be responsive to changes in tonicity of the environment surrounding the spacer substance, pi-bonding availability, and/or other environmental stimuli.

In some embodiments, the spacer substance is a piezoelectric, electrostrictive, or ferroelectric magnetic particle. In some embodiments, the magnetic particle comprises a molecular crystal with a dipole associated with the unit cell. In some embodiments, the magnetic particles can be oriented based on an external magnetic field. Exemplary magnetic particles include lithium niobate, nanocrystals of 4-dimethylamino-N-methyl-4-stilbazolium tosylate (DAST)), crystalline polytetrafluoroethylene (PTFE), electrospun PTFE, and combinations thereof.

In some embodiments, the spacer substance heats up faster or slower than its surroundings. Without being bound by theory, it is believed that such embodiments will allow the rate of passage of permeants, or a subset of permeants, across the membrane to be increased and/or decreased.

In some embodiments, spacer substances respond to electrochemical stimuli. For instance, a spacer substance can be an electrochemical material (e.g., lithium ferrophosphate), where a change in oxidation state of the spacer substance (e.g., from 2- to 3-) alters permeability of the membrane. In some embodiments, changing the oxidation state of the spacer substances alters the interaction between the spacer substance and potential permeants. In some embodiments, the change in oxidation state results from a redox-type reaction. In some embodiments, the change in oxidation state results from a voltage applied to the membrane.

In some embodiments, the spacer substance comprises contamination structures formed by utilizing a focused ion beam, e.g., to modify heavy levels of contamination on graphene-based material into more rigid structures. For instance, in some embodiments, mobilization and migration of contamination on the surface of the graphene-based material occurs—coupled in some embodiments with some slight beam induced deposition—followed by modification and induced bonding where the beam is applied. In some embodiments, combining contamination structures allows the geometry, thickness, rigidity, and composition of the spacer substance to be tuned to respond to an environmental stimulus (e.g., pressure).

Exemplary spacer substance includes particle substances such as metal nanoparticles (e.g., silver nanoparticles), oxide nanoparticles, octadecyltrichlorosilane nanoparticles, carbon nanotubes, and fullerenes. In some embodiments, the spacer substance includes nanorods, nano-dots (including decorated nano-dots), nanowires, nanostrands, and lacey carbon materials.

In some embodiments, the spacer moiety is responsive to an environmental stimulus, for example, the spacer substance may expand and/or contracts in response to the environmental stimulus. The spacer substance may reversibly expand and/or reversibly contract in response to the environmental stimulus. For instance, conformational changes between trans and cis forms of a spacer substance can alter the effective diameter of the spacer substance (by way of example, a spacer substance could be a polymer with an embedded diazo dye, where exposure to the appropriately colored light alters the volume of the dye based on cis-/trans-conformational changes). In some embodiments, the spacer substance undergoes a physical and/or chemical transformation that is pH-modulated or optically modulated. In some embodiments, the environmental stimulus degrades the spacer substance to alter the effective diameter of the spacer substance.

In some embodiments, the environmental stimulus induces a conformational change in the spacer substance that alters the effective length of the spacer substance. Environmental stimuli may include, for example, changes in temperature, pressure, pH, ionic concentration, solute concentration, tonicity, light, voltage, electric fields, magnetic fields, pi-bonding availability, and combinations thereof.

The polymers described herein may include additional monomeric components, biocompatible silicone, hexamethyl trisiloxane (D3), epoxy, both cyclohexyl epoxies, amenable to UV curing, and epichlorohydrin, amenable to substitution on the carbonyl functionality of graphene. The epichlorohydrin may be curable via thermal methods, and provides a durable, cross-linked graphene polymer. Some polymeric cross-linkers initiators may be curing agents, such as diamines. Other monomers and chain spacers may be included, such as aromatic and alkyl di-carboxylic acids curing via the hydroxyl functionality on the graphene platelets to create polyester cured graphene.

The cross-linked graphene platelet polymers described herein have a sufficient crosslink density to prevent large gaps of uncured section of graphene, which may allow, e.g., salt, to pass unimpeded through greater than about 1 nm holes (or spaces between platelets). In some embodiments, the cross-linked graphene platelet polymers have a crosslink density of 0-0.33 (for example, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, or 0.33, and measured by differential scanning calorimetry. In some other embodiments, the cross-linked graphene platelet polymer compositions contain less than about 5%, 4%, 3%, 2%, 1%, 0.5%, 0.1% holes (or spaces between platelets) greater than about 1 nm. In some other embodiments, the cross-linked graphene platelet polymer composition is substantially free of holes (or spaces between platelets) greater than about 1, 1.1, 1.2, 1.3, 1.4, 1.5, 1.6, 1.7, 1.8, 1.9 or 2 nm. In some embodiments, cross-linked graphene platelet polymer composition comprises holes (or spaces between platelets) between 0.5 and 2.0 nm. The other embodiments, the space between platelets changes in response to an environmental stimulus as described herein. The space between platelets may be between 0.5 and 2.0 nm after or before the change in response to an environmental stimulus as described herein.

In other embodiments, the cross-linked graphene platelet polymer composition has a crosslink density sufficient to reduce the sodium content in a 3.5% saline solution by at least 50, 60, 70, 80, 90 or 100 fold when passed through the cross-linked graphene platelet polymer composition having a thickness of about 100 nm. Other embodiments include, e.g., about 50, 60, 70, 80, 90, 100, 110, 120, 130, 140, 150, 160, 170, 180, 190, 200, 210, 220, 230, 240, or 250 nm, or values in between.

Figure 23:
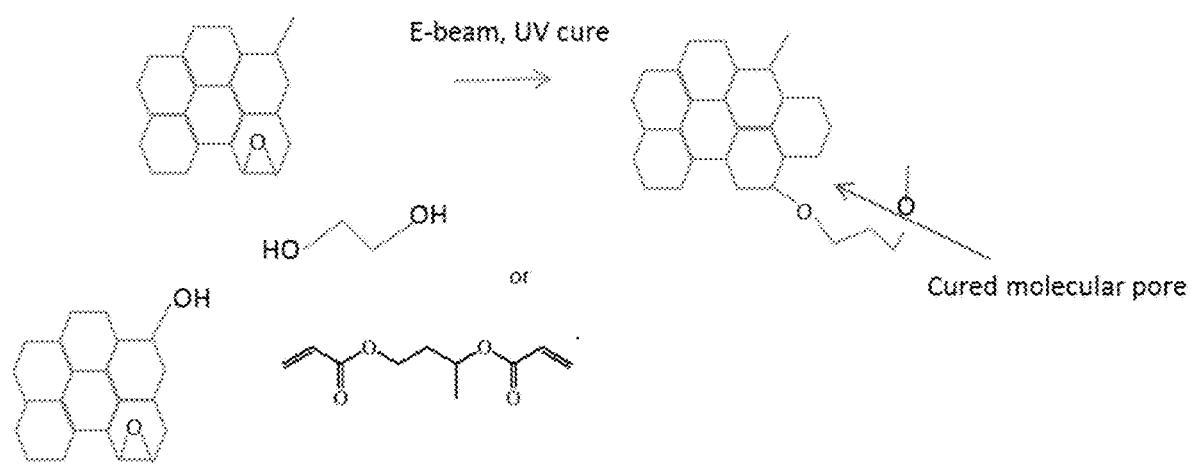
FIG. 23 is an example reaction scheme of some embodiments.

FIG. 23 demonstrates an exemplary reaction scheme of an embodiment of some embodiments, wherein the graphene platelet comprises a reactive epoxide moiety and the functional crosslinking compounds are di-functional crosslinking compounds containing either hydroxyl moieties or acrylate moieties.

Additional Optional Components of Cross-Linked Graphene Platelet Polymers

As mentioned above, some embodiments of the graphene platelet comprise one or more functional moieties. In addition, the cross-linked graphene platelet polymer compositions may be further functionalized to remove or reduce one or more deleterious contaminant from a liquid or gas passing through the cross-linked graphene platelet polymer composition. For example, the holes (or spaces between platelets) within the cross-linked graphene platelet polymer composition may be patterned with silver nanoclusters that, e.g., deactivate the bacteria. In other embodiments, the cross-linked graphene platelet polymer composition may be further treated with quaternary alkyl-ammonium bromide compounds that, e.g., have been shown to coordinate with the phospholipid shell of viruses. In other embodiments, the cross-linked graphene platelet polymer composition may include ionically or chemisorbed ammonium compounds that are not covalently bound to the cross-linked graphene platelet polymer.

Membranes

The cross-linked graphene platelet polymer may be formed into membranes that remove or reduce one or more deleterious contaminant from a liquid or gas passing through the cross-linked graphene platelet polymer composition. In some embodiments the liquid is water. In some embodiments, the cross-linked graphene platelet polymer compositions may be mounted on a support structure.

In other embodiments, the cross-linked graphene platelet polymer may be formed into membranes that isolate or concentrate one or more desired components from a liquid or gas passing through the cross-linked graphene platelet polymer composition. For example, rare earth ions may be isolated or concentrated from, e.g., seawater by reducing water content where certain components of the seawater (e.g., water) are capable of passing through the cross-linked graphene platelet polymer composition, but the desired compounds, such as rare earth ions, are incapable of passing through the cross-linked graphene platelet polymer composition.

The membranes in some embodiments may include more than one cross-linked graphene platelet polymer composition layers. For example, the different layers may be incorporated into a membrane module, wherein the various layers each has a particular functionality. For example, the filter module comprising at least two separate filters or membranes each comprising a cross-linked graphene platelet polymer composition layer, wherein each filter or membrane is functionalized in a different manner, e.g., wherein the cross-linking moieties generate a spacing of about 1 nanometer between individual graphene platelet moieties, wherein the cross-linking portion contains a 4 to 10 atom link, wherein the cross-linked graphene platelets comprise a thiol moiety, wherein the cross-linked graphene platelets further comprise a metal nanocluster, wherein the cross-linked graphene platelets further comprise a quaternary alkyl-ammonium bromide, or wherein the graphene platelet moieties contains fluorocarbon functionalization.

Figure 24:
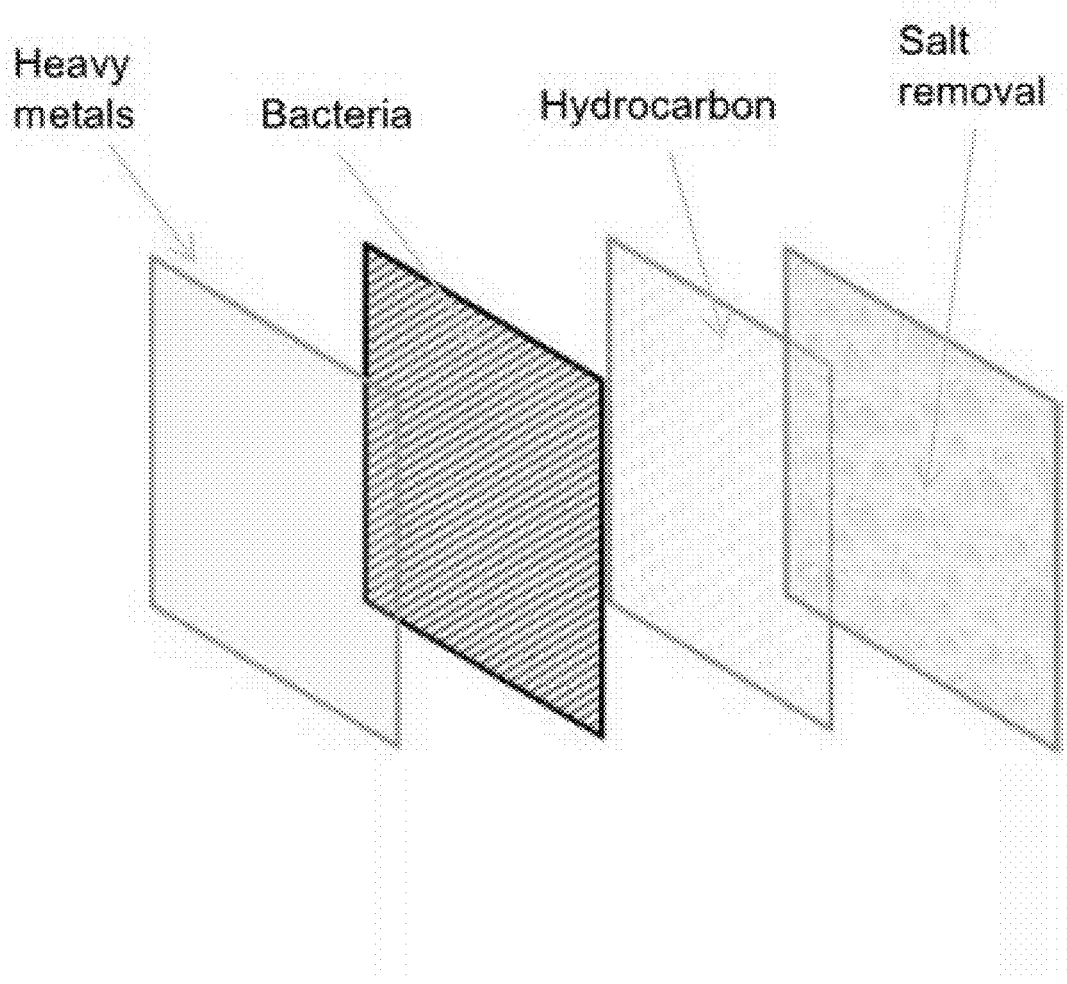
FIG. 24 is an example configuration of a filter module of some embodiments. In these embodiments, there are four different functionalized cross-linked graphene platelet polymer composition layers, each of which is functionalized to remove or reduce the concentration of a different contaminant.

In some embodiments, different layers of the composite membrane module are all incorporated into a modular container, where different modules are incorporated as required to remove/remediate various contaminants as required by the end-user. FIG. 24 provides an exemplary configuration of a filter module of some embodiments. In this embodiment, there are four different functionalized cross-linked graphene platelet polymer composition layers, each of which is functionalized to remove or reduce the concentration of a different contaminant.

In other embodiments, the composite membrane may be used as a separation/barrier layer or for immunoisolation of a second material that is meant to be isolated from an immune response when placed in a biological system (e.g., an animal such as a mammal). For example, it may be used to separate one environment from another within a biological system. The spacing between individual graphene platelet moieties may be such that certain biological components are excluded from passing through the composite membrane.

In other embodiments, the composite membrane may be used in transdermal applications, wherein the spacing between individual graphene platelet moieties may be such that certain biological components are excluded from passing through the composite membrane.

Methods of Use

The filters and membranes of some embodiments have broad application, including in water filtration, immune-isolation (i.e., protecting substances from an immune reaction), timed drug release (e.g., sustained or delayed release), hemodialysis, and hemofiltration. Some embodiments described herein comprise a method of water filtration, water desalination, water purification, immune-isolation, timed drug release, hemodialysis, or hemofiltration, where the method comprises exposing a membrane to an environmental stimulus, and wherein the membrane comprises a cross-linked graphene platelet polymer described herein.

Some embodiments include a method of increasing the purity of a liquid or gas, comprising contacting a first portion of a liquid or gas having an impurity with a filter or membrane comprising the cross-linked graphene platelet polymer compositions to form a second portion of a liquid or gas, wherein the second portion of a liquid or gas contains a lower concentration of the impurity. In some embodiments, the liquid or gas is liquid water. In other embodiments, the liquid or gas is a liquid in a physiological environment, e.g., in an animal, such as a mammal or human. In some embodiments, the impurity is a salt that may be ionized (e.g., NaCl salt or sodium and chloride ions) or a heavy metal or bacteria (or microorganisms, such as viruses) or a hydrocarbon or a larger biological compounds such as antibodies (whereas the filter or membrane can allow passage of biological compounds such as insulin, proteins and/or other biological material (e.g., RNA, DNA, and/or nucleic acids)). In some embodiments, the second portion of liquid or gas (e.g., water) is formed by passing the first portion of liquid or gas (e.g., water) through the cross-linked graphene platelet polymer compositions or filters or membranes of some embodiments. In some embodiments, the second portion of liquid or gas (e.g., water) contains 100-fold or less of the impurity as is found in the first portion of liquid or gas (e.g., water).

Some embodiments include a method of concentrating a material of interest from a liquid or gas, comprising contacting a first portion of a liquid or gas having a composition of interest with a filter or membrane comprising the cross-linked graphene platelet polymer compositions to form a second portion of liquid or gas, wherein the second portion of liquid or gas contains a lower concentration of the composition of interest, and collecting the composition of interest that does not pass through the filter or membrane. Some embodiments include a method of concentrating a composition of interest from water by reducing the water content of a solution of that composition. In some embodiments, the composition of interest may be a rare-earth element.

In some embodiments, the cross-linked graphene platelet polymer compositions and the filter or membrane may be used as a pre-filtration device. For example, some embodiments include a method of increasing the purity of water, comprising contacting a first portion of water having an impurity with a filter or membrane comprising the cross-linked graphene platelet polymer compositions to form a second portion of water, wherein the second portion of water contains a lower concentration of the impurity, followed by contacting the second portion of water with a perforated graphene filter or membrane. Some exemplary perforated graphene filters and membranes are described in the art.

Other embodiments include membranes wherein the spacing between individual graphene platelet moieties is such that is allows certain compounds to pass freely, but retards the passage of other, larger compounds. In some embodiments include membranes wherein the spacing and functionalization between individual graphene platelet moieties is such that is allows certain compounds to pass freely, but retards the passage of other compounds that interact with the graphene platelet moieties or a functional compound contained in the cross-linked graphene platelet polymer. In exemplary embodiments, a membrane that allows passage of water but excludes salt ions (e.g. $Na^+$ and $Cl^-$) can be tuned to allow passage of both water and salt ions. In other exemplary embodiments, the membrane can be tuned to allow passage of biological compounds such as insulin, proteins and/or other biological material (e.g., RNA, DNA, and/or nucleic acids), but to exclude passage of other larger biological compounds such as antibodies. In some embodiments, the membrane can be tuned to be permeable to oxygen and nutrients, but to exclude passage of cells (such as immune cells), viruses, bacteria, antibodies, and/or complements of the immune system. In some embodiments, the membrane can be tuned from one that allows passage of antibodies to one that inhibits passage of antibodies.

Other embodiments include methods of encasing a material and selectively allowing matter of a certain size to contact the encased material. The linked graphene platelet polymer compositions and filters or membranes may be used as encapsulating materials within a biological system, wherein the spacing between individual graphene platelet moieties is such that is allows certain compounds to pass freely, but retards the passage of compounds, such as antibodies from traversing the graphene platelet polymer composition. In exemplary embodiments, a membrane that allows passage of water but excludes salt ions (e.g. $Na^+$ and $Cl^-$) can be tuned to allow passage of both water and salt ions. In other exemplary embodiments, the membrane can be tuned to allow passage of biological compounds such as insulin, proteins and/or other biological material (e.g., RNA, DNA, and/or nucleic acids), but to exclude passage of other larger biological compounds such as antibodies. In some embodiments, the membrane can be tuned to be permeable to oxygen and nutrients, but to exclude passage of cells (such as immune cells), viruses, bacteria, antibodies, and/or complements of the immune system. In some embodiments, the membrane can be tuned from one that allows passage of antibodies to one that inhibits passage of antibodies.

Methods of Making

The cross-linked graphene platelet polymers may be formed by reacting one or more functionalized graphene platelets with one or more functionalized crosslinking compounds of some embodiments. In some embodiments, the functionalized graphene platelets and the functionalized crosslinking compounds are reacted by heat or radiation (e.g., UV) or e-beam.

Methods for Perforating Two-Dimensional Materials Using a Broad Ion Field

Some embodiments are directed, in part, to various processes for producing a plurality of holes in graphene, graphene-based materials and other two-dimensional materials. In an embodiment, the first layer comprises a sheet of graphene-based material. Graphene-based materials include, but are not limited to, single layer graphene, multilayer graphene or interconnected single or multilayer graphene domains and combinations thereof. In an embodiment, graphene-based materials also include materials which have been formed by stacking single or multilayer graphene sheets. In embodiments, multilayer graphene includes 2 to 20 layers, 2 to 10 layers or 2 to 5 layers. In embodiments, graphene is the dominant material in a graphene-based material. For example, a graphene-based material comprises at least 30% graphene, or at least 40% graphene, or at least 50% graphene, or at least 60% graphene, or at least 70% graphene, or at least 80% graphene, or at least 90% graphene, or at least 95% graphene. In embodiments, a graphene-based material comprises a range of graphene selected from 30% to 95%, or from 40% to 80% from 50% to 70%, from 60% to 95% or from 75% to 100%.

As used herein, a "domain" refers to a region of a material where atoms are uniformly ordered into a crystal lattice. A domain is uniform within its boundaries, but different from a neighboring region. For example, a single crystalline material has a single domain of ordered atoms. In an embodiment, at least some of the graphene domains are nanocrystals, having domain size from 1 to 100 nm or 10-100 nm. In an embodiment, at least some of the graphene domains have a domain size greater than 100 nm to 1 micron, or from 200 nm to 800 nm, or from 300 nm to 500 nm. "Grain boundaries" formed by crystallographic defects at edges of each domain differentiate between neighboring crystal lattices. In some embodiments, a first crystal lattice may be rotated relative to a second crystal lattice, by rotation about an axis perpendicular to the plane of a sheet, such that the two lattices differ in "crystal lattice orientation".

In an embodiment, the sheet of graphene-based material comprises a sheet of single or multilayer graphene or a combination thereof. In an embodiment, the sheet of graphene-based material is a sheet of single or multilayer graphene or a combination thereof. In another embodiment, the sheet of graphene-based material is a sheet comprising a plurality of interconnected single or multilayer graphene domains. In an embodiment, the interconnected domains are covalently bonded together to form the sheet. When the domains in a sheet differ in crystal lattice orientation, the sheet is polycrystalline.

In embodiments, the thickness of the sheet of graphene-based material is from 0.34 to 10 nm, from 0.34 to 5 nm, or from 0.34 to 3 nm. In an embodiment, a sheet of graphene-based material comprises intrinsic defects. Intrinsic defects are those resulting from preparation of the graphene-based material in contrast to perforations which are selectively introduced into a sheet of graphene-based material or a sheet of graphene. Such intrinsic defects include, but are not limited to, lattice anomalies, pores, tears, cracks or wrinkles. Lattice anomalies can include, but are not limited to, carbon rings with other than 6 members (e.g. 5, 7 or 9 membered rings), vacancies, interstitial defects (including incorporation of non-carbon atoms in the lattice), and grain boundaries.

In an embodiment, the layer comprising the sheet of graphene-based material further comprises non-graphenic carbon-based material located on the surface of the sheet of graphene-based material. In an embodiment, the non-graphenic carbon-based material does not possess long range order and may be classified as amorphous. In embodiments, the non-graphenic carbon-based material further comprises elements other than carbon and/or hydrocarbons. Non-carbon elements which may be incorporated in the non-graphenic carbon include, but are not limited to, hydrogen, oxygen, silicon, copper and iron. In embodiments, the non-graphenic carbon-based material comprises hydrocarbons. In embodiments, carbon is the dominant material in non-graphenic carbon-based material. For example, a non-graphenic carbon-based material comprises at least 30% carbon, or at least 40% carbon, or at least 50% carbon, or at least 60% carbon, or at least 70% carbon, or at least 80% carbon, or at least 90% carbon, or at least 95% carbon. In embodiments, a non-graphenic carbon-based material comprises a range of carbon selected from 30% to 95%, or from 40% to 80%, or from 50% to 70%.

Such nanomaterials in which pores are intentionally created will be referred to herein as "perforated graphene", "perforated graphene-based materials" or "perforated two-dimensional materials." Some embodiments are also directed, in part, to perforated graphene, perforated graphene-based materials and other perforated two-dimensional materials containing a plurality of holes ranging from about 0.3 nm to about 10 nm in size. Some embodiments are further directed, in part, to perforated graphene, perforated graphene-based materials and other perforated two-dimensional materials containing a plurality of holes ranging from about 0.3 nm to about 10 nm in size and having a narrow size distribution, including but not limited to a 1-10% deviation in size or a 1-20% deviation in size. In an embodiment, the characteristic dimension of the holes is from 0.5 nm to 10 nm. For circular holes, the characteristic dimension is the diameter of the hole. In embodiments relevant to non-circular pores, the characteristic dimension can be taken as the largest distance spanning the hole, the smallest distance spanning the hole, the average of the largest and smallest distance spanning the hole, or an equivalent diameter based on the in-plane area of the pore. As used herein, perforated graphene-based materials include materials in which non-carbon atoms have been incorporated at the edges of the pores As discussed above, conventional processes for perforating graphene and other two-dimensional materials with a plurality of holes can be limited in terms of the obtained hole density, hole size and size distribution. Perforated nanomaterials having small holes with an effective size of about 10 nm or less can be particularly difficult to produce with a sufficient hole density and size distribution to support many intended applications. Filtration applications, for example, can be significantly impacted by an inability to produce holes of a selective size and hole density, as selectivity and throughput flux can be severely impacted. Moreover, presently available techniques for perforating graphene and other two-dimensional materials are not believed to be scalable to large dimensional areas (e.g., one to tens of square centimeters or more) in order to support commercial production efforts.

Current methods for perforating graphene and other two-dimensional materials include both chemical and physical processes. Chemical processes generally involve both hole nucleation and hole growth stages. However, hole nucleation and hole growth are usually difficult to separate from one another, thereby leading to a broad distribution of hole sizes. Physical processes generally involve a brute force knockout of atoms from the planar structure of the two-dimensional material. However, physical processes are rather energy inefficient, especially when considering their scaleup for commercial production efforts. Moreover, high energy ions can actually interact rather poorly with graphene and other two-dimensional materials, leading to a poor yield of atoms ejected during the knockout process.

In an embodiment, energetic ion perforation processes for graphene, graphene-based materials and other two-dimensional materials can be significantly enhanced by conducting the perforation process with at least one layer of a second material in continuous contact with the graphene or other two-dimensional material during its exposure to a broad field or flood ion source. A broad field or flood ion source can provide an ion flux which is significantly reduced compared to a focused ion beam. In an embodiment, the ion flux is from 0.1 nA/mm$^2$ to 100 nA/mm$^2$. By utilizing a broad ion field in conjunction with at least one layer in continuous contact with the graphene or other two-dimensional material, significantly improved perforation can be obtained in the form of small hole sizes, narrow size distributions, and high hole densities. In an embodiment, the hole density is characterized by the spacing between the holes. In an embodiment where the average pore size is from 0.5 nm to 2.5 nm, the average spacing between the pores is from 0.5 nm to 5 nm. The processes of the some embodiments are readily distinguished from focused ion beam processes, which have higher ion fluxes and/or ion energies. The broad ion field processes of some embodiments are considerably more scalable in terms of areal coverage for commercial processing. Depending on their location, the layer(s) in continuous contact with the graphene or other two-dimensional material can impact the perforation process in several different ways, as discussed hereinafter.

In embodiments, the energetic ion perforation processes described herein utilize the knockout approach of physical perforation processes while also facilitating a discrete hole growth stage, like chemical processes. Unlike conventional chemical and physical perforation processes, however, the perforation processes of some embodiments advantageously separate the hole nucleation and growth stages from one another while still allowing nucleation and growth to occur in a highly concerted fashion. In embodiments, the one or more layers in continuous contact with the graphene or other two-dimensional material allow highly concerted nucleation and growth to occur. Specifically, the one or more layers allow hole nucleation to be followed in short order by hole growth as a result of a single incident ion impact with the graphene or other two-dimensional material In conventional processes, hole nucleation and growth are not concerted. Because the hole nucleation and growth are separated but concerted stages in the processes of some embodiments, a narrow hole size distribution can be obtained. Moreover, the processes of some embodiments are advantageously suited to produce holes that are about 10 nm in size or under, which can be desirable for a number of applications, including filtration. Further, the hole size and/or hole density can be adjusted to suit the needs of a particular application. In an embodiment, a higher fluence or exposure time increases the number of holes (until the holes begin to overlap). Higher ion energies can either increase or decrease the hole size depending on the details of the interaction. The hole density can be modulated by adjusting the exposure time of the graphene or other two-dimensional material to the ion source.

Thus, the processes of some embodiments are capable of providing all three of the key needs for perforated graphene, graphene-based materials and other two-dimensional materials (small hole size, narrow size distribution, and high hole density). Moreover, because they make use of a broad ion field for affecting perforation, the processes of some embodiments are advantageously scalable to large dimensional areas and can support commercial processing efforts.

As indicated above, the broad ion field used to affect perforation in embodiments of the processes of some embodiments provides ions with an ion energy ranging between about 0.75 keV and about 10 keV. In an embodiment the ion energy ranges from 1 keV to 10 keV. In an additional embodiment the ion energy ranges from 1 keV to 5 keV. In a further embodiment the ion energy ranges from 2 keV to 10 keV. In an additional embodiment the ion energy ranges from 5 keV to 10 keV. Some ions having energies within this range may interact poorly with graphene and other two-dimensional materials, producing only point defects in the planar structure in the form of 1-2 knocked out atoms per incident ion (single-vacancies and di-vacancies). In an embodiment, the holes produced by the processes of some embodiments produce holes larger in size than such a point defect. The processes of some embodiments, specifically the layer(s) in continuous contact with the graphene or other two-dimensional material, can produce holes larger in size than would be predicted on the basis of the ion energy alone. Without wishing to be bound by any particular belief, contact of the frontside or backside layer with the two-dimensional material during ion irradiation is believed to advantageously promote expansion of the defects into holes of meaningful size through converting the high energy incident ions into a thermal bombardment of the graphene or other two-dimensional material. Layers in different locations with respect to the ion source can facilitate this effect in several ways through bond energy mismatch, as discussed further herein below.

Although certain embodiments are described herein with graphene as the two-dimensional material, it is to be recognized that other two-dimensional materials can be used similarly in alternative embodiments unless otherwise specified herein. Thus, considerable flexibility can be realized by practicing some embodiments in order to produce a particular perforated two-dimensional material having a desired set of properties.

In various embodiments, processes described herein can include exposing a two-dimensional material in continuous contact with at least one layer to an ion source, and interacting a plurality of ions and/or neutralized ions from the ion source with the two-dimensional material and with the at least one layer. In embodiments, the ions and/or neutralized ions introduce a plurality of defects in the two-dimensional material and an interaction of the ions and/or neutralized ions with the at least one layer promotes expansion of the defects into a plurality of holes defined in the two-dimensional material. The at least one layer is in continuous contact with the two-dimensional material while the two-dimensional material is being exposed to the ion source.

In various embodiments, the two-dimensional material comprises graphene, molybdenum sulfide, or boron nitride. In more particular embodiments, the two-dimensional material can be graphene. Graphene according to some embodiments can include single-layer graphene, multi-layer graphene, or any combination thereof. Other nanomaterials having an extended two-dimensional molecular structure can also constitute the two-dimensional material in the some embodiments. For example, molybdenum sulfide is a representative chalcogenide having a two-dimensional molecular structure, and other various chalcogenides can constitute the two-dimensional material in some embodiments. Choice of a suitable two-dimensional material for a particular application can be determined by a number of factors, including the chemical and physical environment into which the graphene or other two-dimensional material is to be terminally deployed.

In various embodiments, the holes produced in the graphene or other two-dimensional material can range from about 0.3 nm to about 10 nm in size. In a more specific embodiment, the holes can range from about 0.5 nm to about 2.5 nm in size. In an additional embodiment, the hole size is from 0.3 to 0.5 nm. In a further embodiment, the hole size is from 0.5 to 10 nm. In an additional embodiment, the hole size is from 5 nm to 20 nm. In a further embodiment, the hole size is from 0.7 nm to 1.2 nm. In an additional embodiment, the hole size is from 10 nm to 50 nm. In embodiments where larger hole sizes are preferred, the hole size is from 50 nm to 100 nm, from 50 nm to 150 nm, or from 100 nm to 200 nm. Holes within these size ranges can be particularly desirable for filtration applications. The 0.5 nm to 2.5 nm size range can be particularly effective for use in reverse osmosis filtration applications.

Contact times for the graphene or other two-dimensional material with the ion source can range between about 0.1 seconds and about 120 second in order to produce an ion fluence sufficient to produce these hole densities. Longer contact times can be used if desired in order to modulate the number of holes obtained in the planar structure.

The ion source inducing perforation of the graphene or other two-dimensional material in some embodiments is considered to provide a broad ion field, also commonly referred to as an ion flood source. In an embodiment, the ion flood source does not include focusing lenses. In embodiments, the ion source is operated at less than atmospheric pressure, such as at $10^{-3}$ to $10^{-5}$ torr or $10^{-4}$ to $10^{-6}$ torr. In an embodiment, the environment also contains background amounts (e.g. on the order of $10^{-5}$ torr) of oxygen ($O_2$), nitrogen ($N_2$) or carbon dioxide ($CO_2$). As indicated above, in an embodiment the ion source provides an ion dose ranging from $1\times10^{10}$ ions/cm$^2$ to $1\times10^{17}$ ions/cm$^2$ and having an ion energy ranging from 0.75 keV to 10 keV. In more particular embodiments, the ion energy can range from 1 keV to 10 keV or from 5 keV to 10 keV. In some embodiments, the ion dose can range between about $1\times10^{11}$ ions/cm$^2$ and about $1\times10^{15}$ ions/cm$^2$, between about $1\times10^{12}$ ions/cm$^2$ and about $1\times10^{14}$ ions/cm$^2$, or from $1\times10^{13}$ ions/cm$^2$ to $1\times10^{19}$ ions/cm$^2$. In an embodiment, the ion dose ranges from $1\times10^{10}$ ions/cm$^2$ to $1\times10^{17}$ ions/cm$^2$. In an additional embodiment the ion does ranges from $1\times10^{11}$ ions/cm$^2$ to $1\times10^{15}$ ions/cm$^2$. In a further embodiment, the ion dose ranges from $1\times10^{13}$ ions/cm$^2$ to $1\times10^{19}$ ions/cm$^2$. In an embodiment, the flux or beam current density is from 10 nA/nm$^2$ to 100 nA/nm$^2$. In embodiments, the ion beam may be perpendicular to the surface of the layers of the multi-layered material (incidence angle of 0 degrees) or the incidence angle may be from 0 to 45 degrees, 0 to 20 degrees, 0 to 15 degrees or 0 to 10 degrees.

The ion source can provide any of a variety of ions suitable for inducing perforations in graphene, graphene-based materials and other two-dimensional materials. In an embodiment, the ion is singly charged. In another embodiment, the ion is multiply charged. In an embodiment, the ion is a noble gas ion (ion of an element from Group 18 of the periodic table). In an embodiment, the ion is other than a helium ion. In an embodiment the ion is an organic ion or organometallic ion. In an embodiment, the organic or organometallic ion has an aromatic component. In an embodiment, the molecular mass of the organic ion or organometallic ion is from 75 to 200 or 90 to 200. In illustrative embodiments, ions that can be supplied from the ion source to induce perforation of graphene or another two-dimensional material can include Xe$^+$ ions, Ne$^+$ ions, Ar$^+$ ions, tropyllium ions ($C_7H_7^+$) and ferrocenium ions $[(C_5H_5)_2Fe^+]$. In embodiments, when the ions are Xe$^+$ ions, Ne$^+$ ions, Ar$^+$ ions, the dose is $1\times10^{11}$ ions/cm$^2$ to $1\times10^{15}$ ions/cm$^2$. In embodiments, when the ion comprises a plurality of elements (such as tropyllium and ferrocenium), the fluence is $1\times10^{11}$ ions/cm$^2$ to $1\times10^{15}$ ions/cm$^2$. In an embodiment, helium ions are provided with a dose from $1\times10^{13}$ ions/cm$^2$ to $1\times10^{19}$ ions/cm$^2$. The chosen ion and its energy can determine, at least in part, the size of the holes obtained in the graphene or other two dimensional material. In particular embodiments, the chosen ion and its energy can be chosen to eject fragments from the at least one layer toward the graphene or other two-dimensional material.

In an embodiment, the temperature of the multilayer composite is controlled during ion bombardment. In embodiment, the temperature is controlled from −130° C. to 200° C. or from −130° C. to 100° C. In an embodiment, the temperature may be selected to allow condensation of a gas on the frontside of the two-dimensional material. In an embodiment, where a metal backside layer is present, the temperature may be controlled from 50° C. to 80° C. The one or more layers in continuous contact with the graphene or other two-dimensional material can be a frontside layer or a backside layer, or both can be present. The term "frontside" refers to the condition of being on the same side of the two-dimensional material as the ion source. The term "backside" refers to the condition of being on the side of the two-dimensional material opposite the ion source. Depending on its location, the at least one layer can be natively or exogenously present on the graphene or other two-dimensional material, or the at least one layer can be intentionally deposited after formation of the graphene or other two dimensional material. For example, a metal growth substrate can constitute a backside layer in various embodiments.

Generally, the at least one layer has a bond energy that is weaker than that of graphene or the two-dimensional material, which is characterized by strong bonds. That is, when the at least one layer is interacted with the ion source, bonds are broken in the at least one layer in preference to the graphene or other two-dimensional material due to a bond energy mismatch. In some embodiments, the at least one layer can be a deposited layer such as deposited silicon, a deposited polymer, or any combination thereof. If the graphene or other two-dimensional material remains on its metal growth substrate, a deposited layer can constitute a frontside layer. However, if the graphene or other two-dimensional material has been removed from its metal growth substrate, a deposited layer can constitute either a frontside layer or a backside layer. Deposited polymers that can include any polymer material that suitably adheres to the graphene-based material or other two-dimensional material such as silicone polymers, for example. In an embodiment, the deposited polymer does not completely delaminate from the graphene-based material during ion bombardment. Other suitable polymer layers can be envisioned by one having ordinary skill in the art.

In some embodiments, a frontside layer deposited on the graphene or other two-dimensional material can have a thickness ranging between about 1 nm and about 10 nm. Thicker frontside layers can also be present, if desired. Although the frontside layer can be deposited exogenously during synthesis of the graphene or other two-dimensional material, the frontside layer can also be deposited in a separate operation in other embodiments. For example, the frontside layer can be deposited by sputtering, spraying, spin coating, atomic layer deposition, molecular beam epitaxy or like techniques in some embodiments.

Various layers will now be further described according to their location and function.

In some embodiments, the at least one layer can be at least a frontside layer disposed on the same side of the two-dimensional material as the ion source. Illustrative frontside layers can include those described above. When a frontside layer is present, ions from the ion source interact with the frontside layer before interacting with the graphene or other two-dimensional material. As discussed hereinafter, this type of interaction can still promote the creation and expansion of holes in the planar structure of the graphene or other two-dimensional material by ejecting layer fragments from the frontside layer and impacting the layer fragments with the graphene or other two-dimensional material to form holes therein. Since the frontside layer is relatively thin, it has a low stopping power and allows the ions and/or neutralized ions to penetrate through the frontside layer to further interact with the graphene.

In an embodiment, ion bombardment of the frontside layer generates a plume of more, but lower energy particles, impinging on the graphene or other two dimensional material. In more specific embodiments, processes of some embodiments can include ejecting toward the two-dimensional material a plurality of layer fragments from the frontside layer upon interaction of ions and/or neutralized ions therewith, and impacting the layer fragments with the two-dimensional material in an area of the two-dimensional material surrounding the defects created upon interacting the ions and/or neutralized ions with the two-dimensional material and promoting expansion of the defects into holes. Layer fragments can include atoms, ions, molecules or molecular fragments displaced from the frontside layer upon interaction of a high energy ion with the frontside layer. A frontside layer can be present in combination with a backside layer or a frontside layer can be present alone. Functions of the backside layer are discussed further below.

Without being bound by theory or mechanism, it is believed that hole definition or generation in the presence of a frontside layer can take place due to several synergistic effects. First, the graphene or other two-dimensional material can have an enhanced degree of chemical reactivity in the vicinity of the defects initially created by the high energy ions and/or neutralized ions. Second, the layer fragments from the frontside layer can turn a single impact event at the frontside layer into a plurality of impact events at the graphene or other two-dimensional material. Third, the layer fragments have a lower energy than do the incident high energy ions, thereby increasing the likelihood of successfully interacting with the graphene or other two-dimensional material in order to define a hole. Finally, because the frontside layer and the graphene or other two-dimensional material are in continuous contact with one another, the geometric spread of the layer fragments during their transit to the graphene or other two-dimensional material is minimal, thereby limiting the hole size. Thus, the combination of enhanced chemical reactivity in the vicinity of the defects and the more efficient interaction of the layer fragments with the graphene or other two-dimensional material can result in the definition of a hole.

Figure 25:
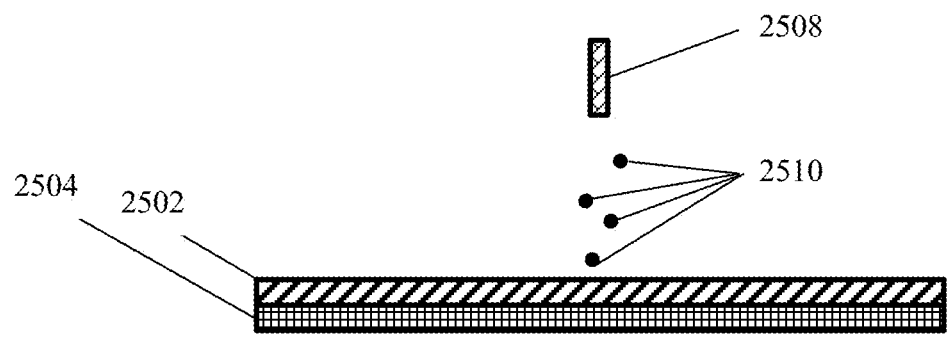
FIG. 25 and FIG. 26 show illustrative schematics of a frontside layer in continuous contact with graphene or another two-dimensional material.
Figure 26:
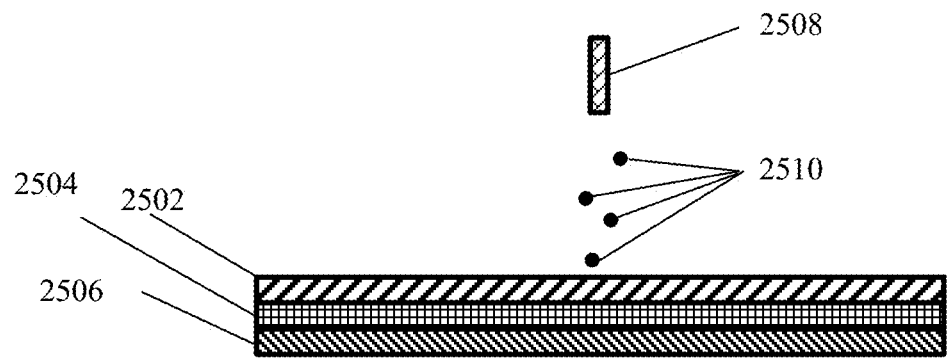

FIGS. 25 and 26 show illustrative schematics of frontside layer 2502 in continuous contact with graphene 2504 or another two-dimensional material. In FIG. 25, only frontside layer 2502 is present, and in FIG. 26, both frontside layer 2502 and backside layer 2506 are present. Ion source 2508 is configured to supply a dose of ions 2510 for perforating graphene 2504.

Figure 27A:
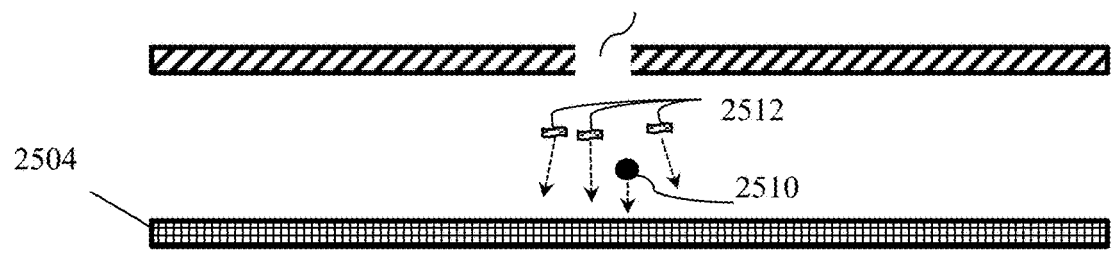
FIG. 27A, FIG. 27B and FIG. 27C show illustrative schematics demonstrating how the interaction of an ion with a frontside layer and with graphene or another two-dimensional material can define a hole in the graphene or other two-dimensional material.
Figure 27B:
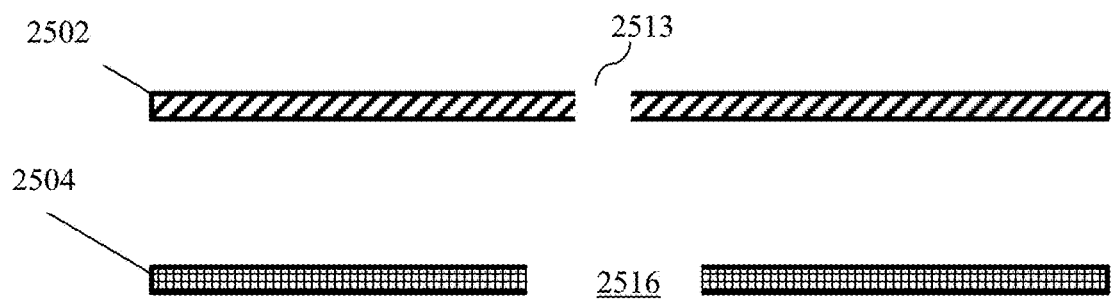
Figure 27C:
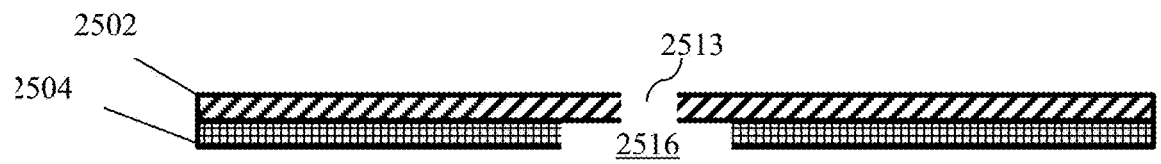

FIGS. 27A, 27B and 27C show illustrative schematics demonstrating how the interaction of an ion with a frontside layer and with graphene or another two-dimensional material can define a hole in the graphene or other two-dimensional material. In the interest of clarity of description and depiction, frontside layer 26 and graphene 28 are shown in an exploded view and in a spaced apart configuration in FIGS. 27A and 27B, rather than in their true configuration of being in continuous contact with one another. FIG. 27A shows frontside layer 2502 and graphene 2504 after ion 10 has impacted and passed through the frontside layer. Layer fragments 2512 are ejected from frontside layer 2502 and are scattered at thermal velocities/energies and/or hyperthermal velocities/energies toward graphene 2504. In an embodiment this scattering may be referred to as ballistic scattering. A defect 2513 is created in the frontside layer. A defect 2514 (not shown in FIG. 27A) may be introduced in graphene 2504 upon the passage of ion 10 through the planar structure of graphene 2504. Again, it is to be emphasized that frontside layer 2502 and graphene 2504 are, in fact, in continuous contact with one another, thereby minimizing the degree of ballistic scattering that takes place as layer fragments 2512 transit from frontside layer 2502 to graphene 2504. In an embodiment, layer fragments 2512 impact graphene 2504 in close proximity to defect 2514, where the chemical reactivity is enhanced. In an embodiment, layer fragments 2512 then result in expansion of defect 2514 to define hole 2516, as shown in FIG. 27B. FIG. 27C shows frontside layer 2502 and graphene 2504 in their true continuous contact configuration after the creation of hole 2516. As exemplified by FIGS. 27A-27C, the stages of hole nucleation (i.e., formation of a defect in the graphene by direct interaction of the ion) and hole growth (i.e., impact of layer fragments 2512 with graphene 2504) are separated, yet highly concerted processes. Therefore, holes 2516 of defined size and having a narrow size distribution can be obtained.

As shown in FIG. 27B, frontside layer 2502 can at least partially cover hole 2516 following its creation. In some embodiments, frontside layer 2502 can be removed following the definition of holes 2516 in order to increase the effective permeability of graphene 2504. Illustrative frontside layer removal techniques can include, for example, oxidation, solvent washes, heating, or any combination thereof. Oxidation techniques include, but are not limited to, ultraviolet-oxygen (UVO) treatment using reactive oxygen species. Depending on the composition of frontside layer 2502, one having ordinary skill in the art will be able to choose a suitable removal process.

In some embodiments, the at least one layer in continuous contact with the graphene or other two dimensional material can be a backside layer disposed on a side of the graphene or other two-dimensional material opposite the ion source. In an embodiment, the backside layer is a metal growth substrate upon which the graphene or other two-dimensional material is grown, or the backside layer can be a secondary substrate to which the graphene or other two-dimensional material has been transferred following growth. In an embodiment, the secondary substrate is polymeric, including porous polymeric membranes. In either case, the backside layer can have a thickness that is significantly greater than that of the graphene or other two-dimensional material. Accordingly, the backside layer can have a much higher stopping power for the energetic ions and/or neutralized ions than does the graphene or other two-dimensional material. Upon stopping the energetic ions, the backside layer can disperse an impact energy of the ions and/or neutralized ions with the backside layer into an area of the graphene or other two-dimensional material surrounding the defects created upon interacting the ions with the two-dimensional material and promoting the expansion of the defects into holes. In more specific embodiments, a backside layer promotes expansion of defects in a two-dimensional material into holes in a manner somewhat similar to that described above for a frontside layer, in which fragments are directed towards the two-dimensional material. The backside layer may also promote formation of defects in the two-dimensional material. For example, even when an ion or neutralized ion does not form a hole when passing through the two-dimensional material, impact of the ions and/or neutralized ions with the backside layer may cause a small region in the backside layer to rapidly heat and expand, opening a hole in the graphene or other two-dimensional material.

Figure 28A:
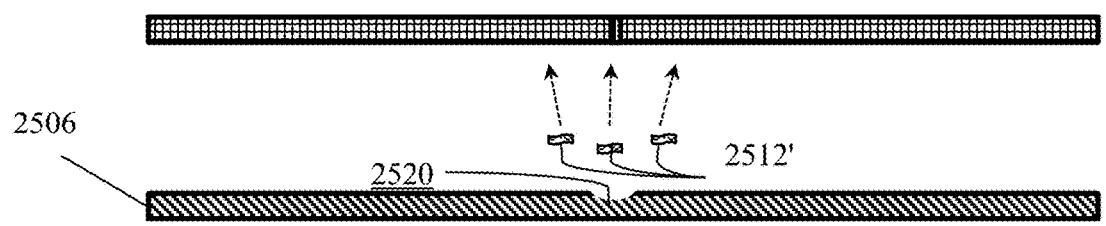
FIG. 28A, FIG. 28B and FIG. 28C show illustrative schematics demonstrating how the interaction of an ion with a backside layer and with graphene or another two-dimensional material can define a hole in the graphene or other two-dimensional material.
Figure 28B:
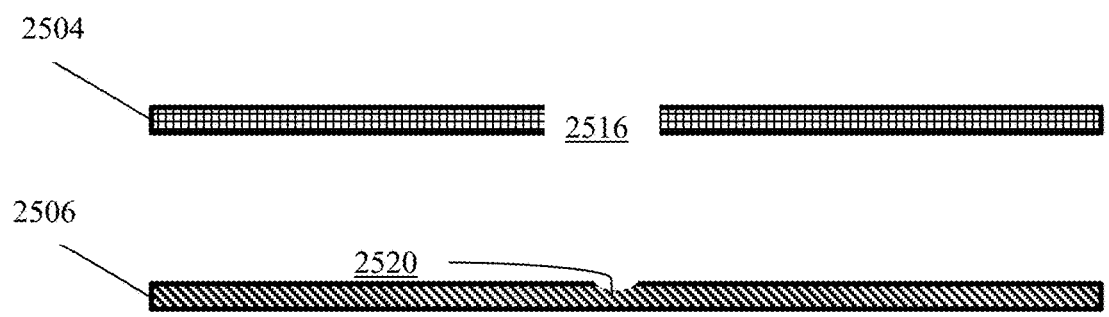
Figure 28C:
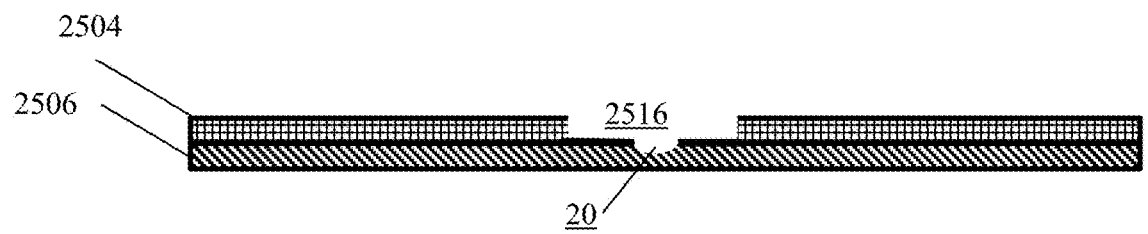

FIGS. 28A, 28B and 28C show illustrative schematics demonstrating how the interaction of an ion with a backside layer and with graphene or another two-dimensional material can define a hole in the graphene or other two-dimensional material. Again, in the interest of clarity of description and depiction, backside layer 2506 and graphene 2504 are shown in an exploded view and in a spaced apart configuration in FIGS. 28A and 28B, rather than in their true configuration of being in continuous contact with one another. FIG. 28A shows graphene 2504 or another two-dimensional material and backside layer 2506 immediately after an ion has passed through graphene 2504 and impacted backside layer 2506. Defect 2514 is generated in graphene 2504 upon passage of the ion therethrough. In the case of backside layer 2506, the ion embeds in impact region 20, thereby resulting in ejection of layer fragments 2512' therefrom. In FIG. 28A, impact region 20 is shown as a crater. Layer fragments 2512' can include those described above for frontside layer 2502. For example, when backside layer 2506 is the metal growth substrate upon which graphene 2504 or another two-dimensional material is grown, layer fragments 2512' can be metal atoms or metal ions sputtered from the metal growth substrate upon kinetic energy transfer from the ion to backside layer 2506. Layer fragments 2512' are ejected toward graphene 2504 at thermal velocities and again impact in close proximity to defect 2514 to result in its expansion into hole 2516, as depicted in FIG. 28B. In the configuration of FIGS. 28A and 28B, layer fragments 2512' impact graphene 2504 from its underside, rather than from its topside as in FIGS. 27A and 27B. Again, it is to be emphasized that backside layer 2506 and graphene 2504 are, in fact, in continuous contact with one another, thereby minimizing the degree of scattering that takes place as layer fragments 2512' transit from backside layer 2506 to graphene 2504. As shown, layer fragments 2512' impact graphene 2504 in close proximity to defect 2514 to where the chemical reactivity is enhanced. FIG. 28C shows backside layer 2506 and graphene 2504 in their true continuous contact configuration after the creation of hole 2516. As exemplified by FIGS. 28A-28C, the stages of hole nucleation (i.e., formation of defect 2514) and hole growth (i.e., impact of layer fragments 2512' with graphene 2504) are again separated, yet highly concerted processes. Because there is minimal geometric scattering as layer fragments 2512' transit between backside layer 2506 and graphene 2504, holes 2516 having a defined size and a narrow size distribution can be obtained.

Illustrative metal growth substrates upon which graphene, graphene-based materials and other two-dimensional materials can be grown and which can serve as the backside layer in some embodiments include various metal surfaces containing a transition metal. In the case of graphene, for example, copper or nickel can be particularly effective for promoting epitaxial graphene growth. In some embodiments, the metal growth substrate can be formed substantially entirely of a metal, such as a metal foil or a metal sheet. In other embodiments, the metal growth substrate can include a metal surface on a different subsurface material. For example, a ceramic substrate having a metal surface can be used as the metal growth substrate and backside layer in some embodiments.

Accordingly, in some embodiments, processes of some embodiments can include ejecting toward the two-dimensional material, such as graphene, a plurality of layer fragments from the backside layer upon interaction of the ions and/or neutralized ions therewith, and impacting the layer fragments with the two-dimensional material in an area of the two-dimensional material surrounding the defects and promoting expansion of the defects into holes. That is, the backside layer can promote energy transfer to the graphene or other two-dimensional material in the form of layer fragments having thermal velocities in order to promote the creation of holes in the graphene or other two-dimensional material.

In some embodiments, both a frontside layer and a backside layer can be in continuous contact with the graphene or other two-dimensional material as it is interacted with the ions and/or neutralized ions from the ion source. The layer fragments generated from both the frontside layer and the backside layer can work in concert with one another to expand the generated defects in the graphene or other two-dimensional material into a plurality of holes. For example, in some embodiments, layer fragments generated from a suitable frontside layer and metal atoms or metal ions generated from a backside metal growth substrate can impact graphene from both sides of its planar structure to promote the creation of holes therein. This can be particularly effective for perforating multi-layer two-dimensional materials, such as multi-layer graphene, for example by holding the particles in a local region.

Accordingly, in embodiments where both a frontside layer and a backside layer are present, processes of some embodiments can include ejecting toward the graphene or other two-dimensional material a plurality of layer fragments from the frontside layer upon interaction of the ions and/or neutralized ions therewith, ejecting toward the graphene or other two-dimensional material a plurality of layer fragments from the backside layer upon interaction of the ions and/or neutralized ions therewith, and impacting the layer fragments from both layers with the graphene or other two-dimensional material in an area surrounding the defects created upon interacting the ions and/or neutralized ions with the graphene or other two-dimensional material and promoting the expansion of the defects into holes.

In particular embodiments, processes of some embodiments can include exposing graphene on a metal growth substrate to an ion source, interacting a plurality of ions from the ion source with the graphene and with the metal growth substrate to introduce a plurality of defects in the graphene and an interaction of the ions and/or neutralized ions with the metal growth substrate ejecting toward the graphene a plurality of layer fragments including metal ions or metal atoms from the metal growth substrate, and expanding the defects in the graphene with the layer fragments to define a plurality of holes in the graphene. In an embodiment, the ion source provides to the graphene an ion dose ranging between about $1\times10^{11}$ ions/cm$^2$ and about $1\times10^{17}$ ions/cm$^2$ and having an ion energy ranging between about 0.75 keV and about 10 keV. The metal growth substrate is disposed on a side of the graphene opposite the ion source and constitutes a backside layer.

In some embodiments, the graphene can be coated with a frontside layer opposite the metal growth substrate that is disposed on the same side of the graphene as the ion source (see FIG. 26, for example). The frontside layer can be formed from various materials and can have a thickness ranging between about 1 nm and about 10 nm, for example. In some embodiments, the processes can further include removing the frontside layer after defining the plurality of holes in the graphene.

In other particular embodiments, processes of some embodiments can include exposing graphene to an ion source, the graphene having thereon a frontside layer disposed on the same side of the graphene as the ion source, interacting a plurality of ions and/or neutralized ions from the ion source with the graphene and with the frontside layer to introduce a plurality of defects in the graphene and an interaction of the ions and/or neutralized ions with the frontside layer ejecting toward the graphene a plurality of layer fragments, and expanding the defects in the graphene with the layer fragments to define a plurality of holes in the graphene. In an embodiment, the ion source provides to the graphene an ion dose ranging between about $1\times10^{11}$ ions/cm$^2$ and about $1\times10^{17}$ ions/cm$^2$ and having an ion energy ranging between about 0.75 keV and about 10 keV.

In still other particular embodiments, processes of some embodiments can include exposing graphene to an ion source, the graphene being present on a backside layer located on a side of the graphene opposite the ion source, interacting a plurality of ions and/or neutralized ions from the ion source with the graphene and with the backside layer to introduce a plurality of defects in the graphene and an interaction of the ions and/or neutralized ions with the backside layer dispersing an impact energy of the ions and/or neutralized ions with the backside layer into an area of the graphene surrounding the defects created upon interacting the ions with the graphene an promoting expansion of the defects into holes. In an embodiment, the ion source provides to the graphene an ion dose ranging between about $1\times10^{10}$ ions/cm$^2$ and about $1\times10^{17}$ ions/cm$^2$ and having an ion energy ranging between about 0.75 keV and about 10 keV.

In more specific particular embodiments, processes of some embodiments can include exposing graphene to an ion source, the graphene being present on a backside layer located on a side of the graphene opposite the ion source, interacting a plurality of ions and/or neutralized ions from the ion source with the graphene and with the backside layer to introduce a plurality of defects in the graphene and an interaction of the ions and/or neutralized ions with the backside layer ejecting toward the graphene a plurality of layer fragments, and expanding the defects in the graphene with the layer fragments to define a plurality of holes in the graphene. In an embodiment, the ion source provides to the graphene an ion dose ranging between about $1\times10^{10}$ ions/cm$^2$ and about $1\times10^{17}$ ions/cm$^2$ and having an ion energy ranging between about 0.75 keV and about 10 keV.

The perforated graphene, graphene-based materials and other two-dimensional materials described herein can be used in a variety of applications including filtration, electronics, barrier layers and films, gas barriers, and the like. Illustrative filtration applications in which the perforated graphene, graphene-based materials and other perforated two-dimensional materials can be used include, for example, reverse osmosis, molecular filtration, ultrafiltration and nanofiltration processes. When used in various filtration processes, the perforated graphene or other perforated two-dimensional material can be perforated and then transferred to a porous secondary substrate, where the perforated graphene or other perforated two-dimensional filtration serves as the active filtration membrane.

Hemodialysis and Hemofiltration Membranes Based Upon a Two-Dimensional Membrane Material and Methods Employing Same Some embodiments are directed to membranes comprising a perforated two-dimensional material disposed upon a porous support structure for use in blood dialysis and blood filtration applications. Such two-dimensional materials are selectively perforated to provide for selective removal of one or more components from the blood. In specific embodiments, such two-dimensional materials are selectively perforated to provide for selective removal of one or more selected undesirable components from blood while retaining one or more selected desirable components in the blood.

Some embodiments are directed, in part, to hemodialysis membranes and hemodialysis systems containing selectively perforated graphene or another selectively perforated two-dimensional material. Some embodiments are also directed, in part, to methods for performing a hemodialysis treatment using a hemodialysis system containing such perforated graphene or another such perforated two-dimensional material. Methods herein include hemodialysis cross flow configurations. Methods herein include single-pass methods in which used dialysate is not recirculated and multi-pass systems in which used dialysate is mixed with fresh dialysate and reused.

Some embodiments are directed, in part, to blood filtration membranes and blood filtration systems containing selectively perforated graphene or another selectively perforated two-dimensional material. Some embodiments are also directed, in part, to methods for performing a hemodialysis treatment using a hemodialysis system containing such perforated graphene or another such perforated two-dimensional material Graphene has garnered widespread interest for use in a number of applications due to its favorable mechanical and electronic properties. Graphene represents an atomically thin layer of carbon (or few carbon layers) in which the carbon atoms reside as closely spaced atoms at regular lattice positions. The regular lattice positions can have a plurality of defects present therein, which can occur natively or be intentionally introduced to the graphene basal plane. Such defects will also be equivalently referred to herein as "apertures," "perforations," or "holes." The term "perforated graphene" will be used herein to denote a graphene sheet with defects in its basal plane, regardless of whether the defects are natively present or intentionally produced. Aside from such apertures, graphene and other two-dimensional materials (e.g., graphene oxide and the like) can represent an impermeable layer to many substances. Therefore, if they are sized properly, the apertures in the impermeable layer can be useful in retaining entities that are larger than the effective pore size. In this regard, a number of techniques have been developed for introducing a plurality of perforations in graphene and other two-dimensional materials, where the perforations have a desired size, number and chemistry about the perimeter of the perforations. Chemical modification of the apertures can allow entities having particular chemical characteristics to be preferentially retained or rejected as well.

Two-dimensional materials are, most generally, those which are atomically thin, with thickness from single-layer sub-nanometer thickness to a few nanometers, and which generally have a high surface area. Two-dimensional materials include metal chalogenides (e.g., transition metal dichalogenides), transition metal oxides, hexagonal boron nitride, graphene, silicene and germanene (see: Xu et al. (2013) "Graphene-like Two-Dimensional Materials) Chemical Reviews 113:3766-3798). Graphene represents a form of carbon in which the carbon atoms reside within a single atomically thin sheet or a few layered sheets (e.g., about 20 or less) of fused six-membered rings forming an extended sp2-hybridized carbon planar lattice. In its various forms, graphene has garnered widespread interest for use in a number of applications, primarily due to its favorable combination of high electrical and thermal conductivity values, good in-plane mechanical strength, and unique optical and electronic properties. Other two-dimensional materials having a thickness of a few nanometers or less and an extended planar lattice are also of interest for various applications. In an embodiment, a two dimensional material has a thickness of 0.3 to 1.2 nm. In other embodiments, a two dimensional material has a thickness of 0.3 to 3 nm.

In various embodiments, the two-dimensional material comprises a sheet of a graphene-based material. In an embodiment, the sheet of graphene-based material is a sheet of single- or multi-layer graphene or a sheet comprising a plurality of interconnected single- or multi-layer graphene domains. In embodiments, the multilayer graphene domains have 2 to 5 layers or 2 to 10 layers. In an embodiment, the layer comprising the sheet of graphene-based material further comprises non-graphenic carbon-based material located on the surface of the sheet of graphene-based material. In an embodiment, the amount of non-graphenic carbon-based material is less than the amount of graphene. In embodiments, the amount of graphene in the graphene-based material is from 60% to 95% or from 75% to 100%.

The technique used for forming the graphene or graphene-based material in the embodiments described herein is not believed to be particularly limited. For example, in some embodiments CVD graphene or graphene-based material can be used. In various embodiments, the CVD graphene or graphene-based material can be liberated from its growth substrate (e.g., Cu) and transferred to a polymer backing. In some embodiments, the growth substrate may be corrugated before or after the graphene deposition process to produce a graphene or graphene-based material with high surface area. In some embodiments, a growth substrate may be formed as a cylinder to form a sleeve of graphene or graphene-based material, thereby reducing the number of seams that must be sealed to form the enclosure.

The present inventors recognized that many of the techniques used to introduce perforations into graphene-based material and other two-dimensional materials produce perforations having pore sizes similar to those present in conventional hemodialysis membranes. Thus, they can be used for separating impurities having comparable size to those separated using conventional hemodialysis membranes. However, since single-layer or even multi-layer graphene are much thinner than conventional hemodialysis membranes, a much greater transfer rate can be realized, as expressed with the following formula.

Hence, very thin graphene membranes allow for a much greater transport rate to be realized, which can be least 100 times faster than in conventional hemodialysis membranes. In an embodiment, the graphene membranes can be used as a drop-in replacement for conventional hemodialysis membranes.

In addition to the increased transport rate, the size selectivity can advantageously allow decreased collateral metabolite loss to occur during dialysis. Further, the smoothness of the graphene membrane can allow for a lower anticoagulant load to be used during a dialysis procedure, and a reduced incidence of clotting can be realized. Finally, as a result of the foregoing, hemodialysis systems with a decreased footprint size and lower power requirements can be realized. Decreased patient treatment times can ultimately result. Any of these factors can increase profitability of hemodialysis centers.

Likewise, the techniques for introducing perforations to the graphene or graphene-based material are also not believed to be particularly limited, other than being chosen to produce perforations within a desired size range. Perforations are sized as described herein to provide desired selective permeability of a species (atom, molecule, protein, virus, cell, etc.) for a given application. Selective permeability relates to the propensity of a porous material or a perforated two-dimensional material to allow passage (or transport) of one or more species more readily or faster than other species. Selective permeability allows separation of species which exhibit different passage or transport rates. In two-dimensional materials selective permeability correlates to the dimension or size (e.g., diameter) of apertures and the relative effective size of the species. Selective permeability of the perforations in two-dimensional materials, such as graphene-based materials, can also depend on functionalization of perforations (if any) and the specific species that are to be separated. Separation of two or more species in a mixture includes a change in the ratio(s) (weight or molar ratio) of the two or more species in the mixture after passage of the mixture through a perforated two-dimensional material.

Graphene-based materials include, but are not limited to, single layer graphene, multilayer graphene or interconnected single or multilayer graphene domains and combinations thereof. In an embodiment, graphene-based materials also include materials which have been formed by stacking single layer or multilayer graphene sheets. In embodiments, multilayer graphene includes 2 to 20 layers, 2 to 10 layers or 2 to 5 layers. In embodiments, graphene is the dominant material in a graphene-based material. For example, a graphene-based material comprises at least 30% graphene, or at least 40% graphene, or at least 50% graphene, or at least 60% graphene, or at least 70% graphene, or at least 80% graphene, or at least 90% graphene, or at least 95% graphene. In embodiments, a graphene-based material comprises a range of graphene selected from 30% to 95%, from 40% to 80%, from 50% to 70%, from 60% to 95% or from 75% to 100%.

As used herein, a "domain" refers to a region of a material where atoms are uniformly ordered into a crystal lattice. A domain is uniform within its boundaries, but different from a neighboring region. For example, a single crystalline material has a single domain of ordered atoms. In an embodiment, at least some of the graphene domains are nanocrystals, having domain size from 1 to 100 nm or 10 to 100 nm. In an embodiment, at least some of the graphene domains have a domain size greater than 100 nm to 1 micron, or from 200 nm to 800 nm, or from 300 nm to 500 nm. "Grain boundaries" formed by crystallographic defects at edges of each domain differentiate between neighboring crystal lattices. In some embodiments, a first crystal lattice may be rotated relative to a second crystal lattice, by rotation about an axis perpendicular to the plane of a sheet, such that the two lattices differ in "crystal lattice orientation".

In an embodiment, the sheet of graphene-based material comprises a sheet of single layer or multilayer graphene or a combination thereof. In an embodiment, the sheet of graphene-based material is a sheet of single layer or multilayer graphene or a combination thereof. In another embodiment, the sheet of graphene-based material is a sheet comprising a plurality of interconnected single or multilayer graphene domains. In an embodiment, the interconnected domains are covalently bonded together to form the sheet. When the domains in a sheet differ in crystal lattice orientation, the sheet is polycrystalline.

In embodiments, the thickness of the sheet of graphene-based material is from 0.34 to 10 nm, from 0.34 to 5 nm, or from 0.34 to 3 nm. In an embodiment, a sheet of graphene-based material comprises intrinsic defects. Intrinsic defects are those resulting from preparation of the graphene-based material in contrast to perforations which are selectively introduced into a sheet of graphene-based material or a sheet of graphene. Such intrinsic defects include, but are not limited to, lattice anomalies, pores, tears, cracks or wrinkles. Lattice anomalies can include, but are not limited to, carbon rings with other than 6 members (e.g. 5, 7 or 9 membered rings), vacancies, interstitial defects (including incorporation of non-carbon atoms in the lattice), and grain boundaries.

In an embodiment, the layer comprising the sheet of graphene-based material further comprises non-graphenic carbon-based material located on the surface of the sheet of graphene-based material. In an embodiment, the non-graphenic carbon-based material does not possess long range order and may be classified as amorphous. In embodiments, the non-graphenic carbon-based material further comprises elements other than carbon and/or hydrocarbons. Non-carbon elements which may be incorporated in the non-graphenic carbon include, but are not limited to, hydrogen, oxygen, silicon, copper and iron. In embodiments, the non-graphenic carbon-based material comprises hydrocarbons. In embodiments, carbon is the dominant material in non-graphenic carbon-based material. For example, a non-graphenic carbon-based material comprises at least 30% carbon, or at least 40% carbon, or at least 50% carbon, or at least 60% carbon, or at least 70% carbon, or at least 80% carbon, or at least 90% carbon, or at least 95% carbon. In embodiments, a non-graphenic carbon-based material comprises a range of carbon selected from 30% to 95%, or from 40% to 80%, or from 50% to 70%.

Such nanomaterials in which pores are intentionally created will be referred to herein as "perforated graphene", "perforated graphene-based materials" or "perforated two-dimensional materials." Some embodiments are also directed, in part, to perforated graphene, perforated graphene-based materials and other perforated two-dimensional materials containing a plurality of holes of size (or size range) appropriate for a given enclosure application. The size distribution of holes may be narrow, e.g., limited to a 1-10% deviation in size or a 1-20% deviation in size. In an embodiment, the characteristic dimension of the holes is selected for the application. For circular holes, the characteristic dimension is the diameter of the hole. In embodiments relevant to non-circular pores, the characteristic dimension can be taken as the largest distance spanning the hole, the smallest distance spanning the hole, the average of the largest and smallest distance spanning the hole, or an equivalent diameter based on the in-plane area of the pore. As used herein, perforated graphene-based materials include materials in which non-carbon atoms have been incorporated at the edges of the pores.

In various embodiments, the two-dimensional material comprises graphene, molybdenum disulfide, or boron nitride. In more particular embodiments, the two-dimensional material can be graphene. Graphene according to some embodiments can include single-layer graphene, multi-layer graphene, or any combination thereof. Other nanomaterials having an extended two-dimensional molecular structure can also constitute the two-dimensional material in some embodiments. For example, molybdenum sulfide is a representative chalcogenide having a two-dimensional molecular structure, and other various chalcogenides can constitute the two-dimensional material in some embodiments. Choice of a suitable two-dimensional material for a particular application can be determined by a number of factors, including the chemical and physical environment into which the graphene or other two-dimensional material is to be terminally deployed. For application in some embodiments, materials employed in making an enclosure are preferably biocompatible or can be made biocompatible.

The process of forming holes in graphene and other two-dimensional materials will be referred to herein as "perforation," and such nanomaterials will be referred to herein as being "perforated." In a graphene sheet an interstitial aperture is formed by each six-carbon atom ring structure in the sheet and this interstitial aperture is less than one nanometer across. In particular, this interstitial aperture is believed to be about 0.3 nanometers across its longest dimension (the center to center distance between carbon atoms being about 0.28 nm and the aperture being somewhat smaller than this distance). Perforation of sheets comprising two-dimensional network structures typically refers to formation of holes larger than the interstitial apertures in the network structure.

Due to the atomic-level thinness of graphene and other two-dimensional materials, it can be possible to achieve high liquid throughput fluxes during separation or filtration processes, even with holes that are in the ranges of 1-200 nm, 1-100 nm, 1-50 nm, or 1-20 nm.

Chemical techniques can be used to create holes in graphene and other two-dimensional materials. Exposure of graphene or another two-dimensional material to ozone or atmospheric pressure plasma (e.g., an oxygen/argon or nitrogen/argon plasma) can effect perforation. Other techniques, such as ion bombardment, can also be used to remove matter from the planar structure of two-dimensional materials in order to create holes. All such methods can be applied for preparation of perforated two-dimensional materials for use herein dependent upon the hole sizes or range of hole sizes desired for a given application. The terms holes, pores, apertures and perforations are used interchangeably herein.

In various embodiments of some embodiments, the holes produced in the graphene-based material or other two-dimensional material can range from about 0.3 nm to about 50 nm in size. In a more specific embodiment, hole sizes can range from 1 nm to 50 nm. In a more specific embodiment, hole sizes can range from 1 nm to 10 nm. In a more specific embodiment, hole sizes can range from 5 nm to 10 nm. In a more specific embodiment, hole sizes can range from 1 nm to 5 nm. In a more specific embodiment, the holes can range from about 0.5 nm to about 2.5 nm in size. In an additional embodiment, the hole size is from 0.3 to 0.5 nm. In a further embodiment, the hole size is from 0.5 to 10 nm. In an additional embodiment, the hole size is from 5 nm to 20 nm. In a further embodiment, the hole size is from 0.7 nm to 1.2 nm. In an additional embodiment, the hole size is from 10 nm to 50 nm.

Figure 31:
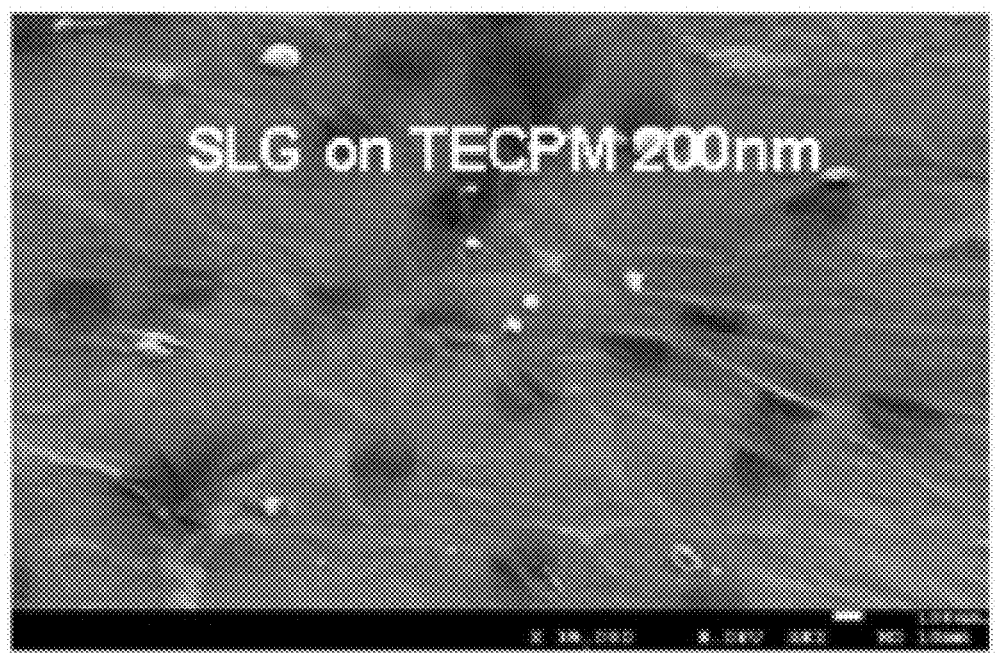
FIG. 31 shows an illustrative scanning electron microscope (SEM) image of perforated single-layer graphene-based material on a track-etched polycarbonate support structure.
Figure 32A:
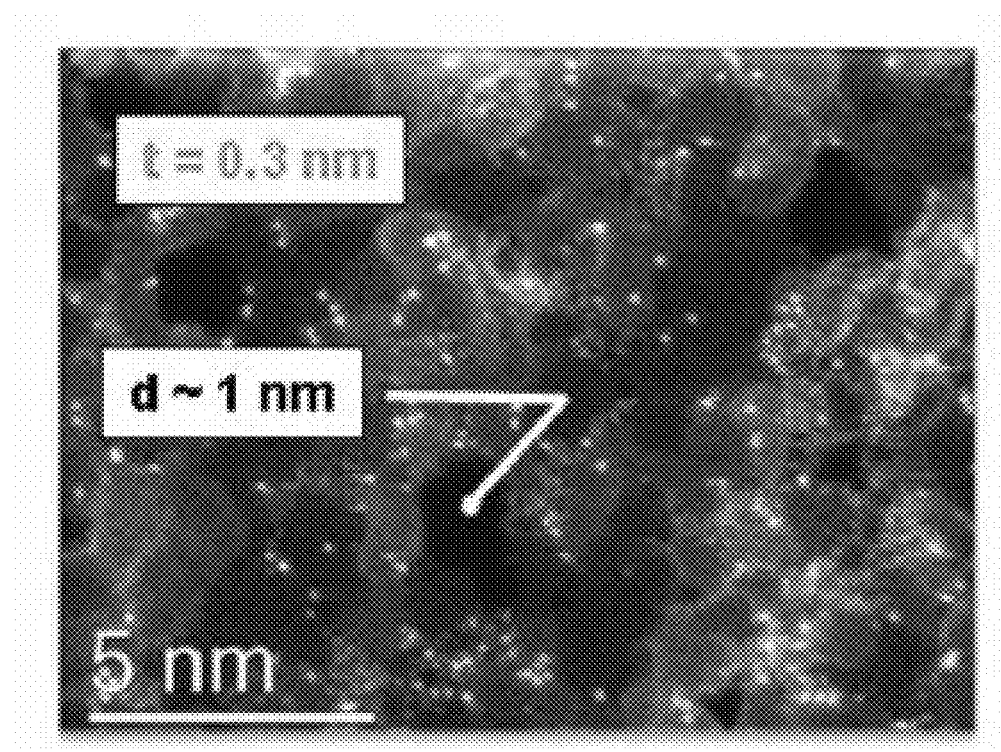
FIGS. 32A-E show images of single layer graphene (nominal thickness of about 0.3 nm) and pores therein.
Figure 32B:
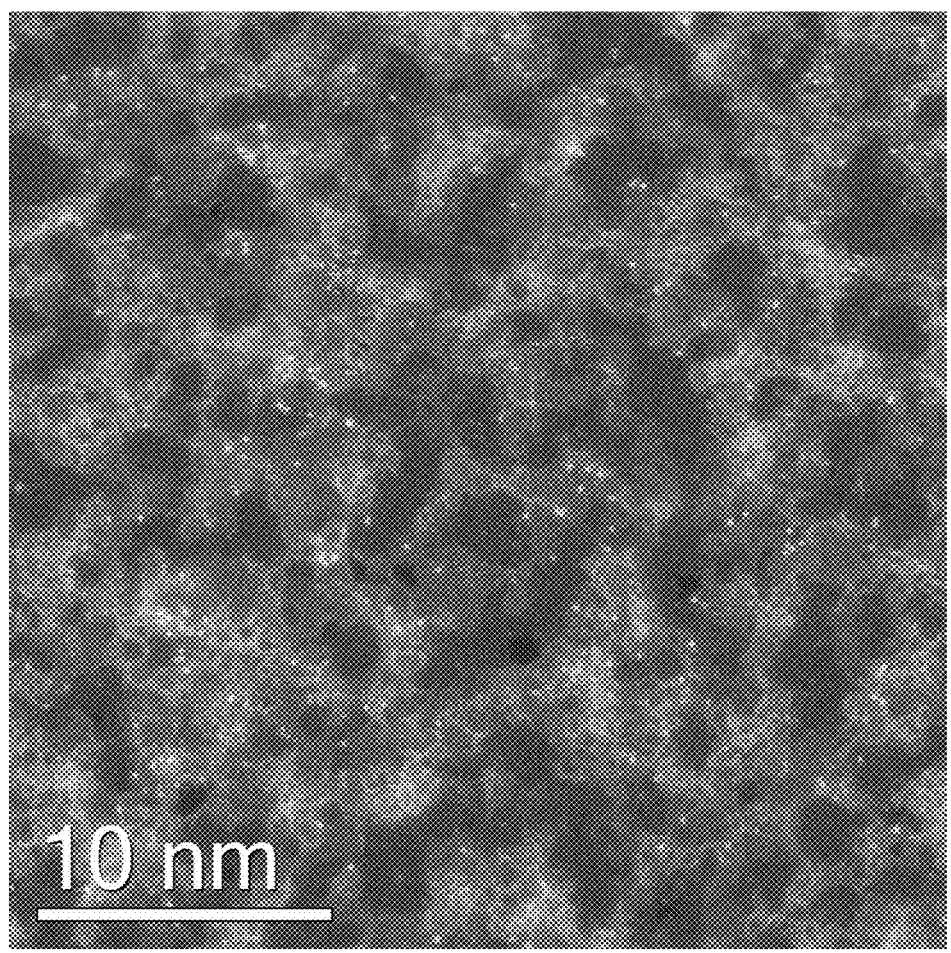
Figure 32C:
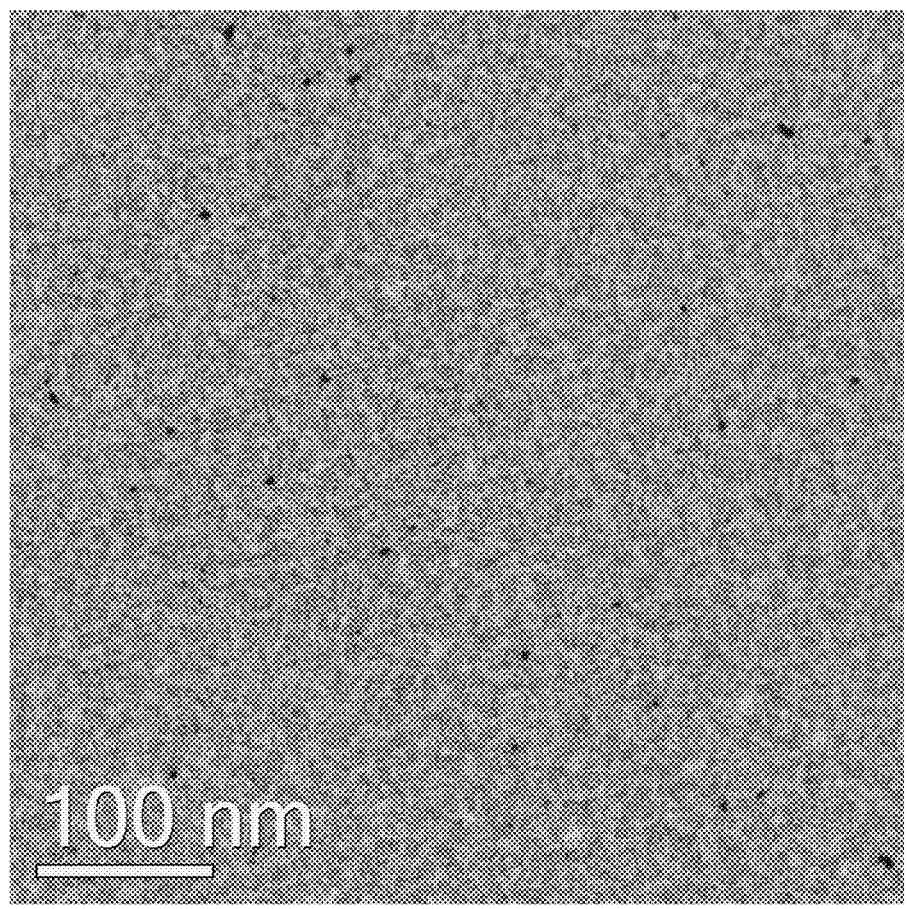
Figure 32D:
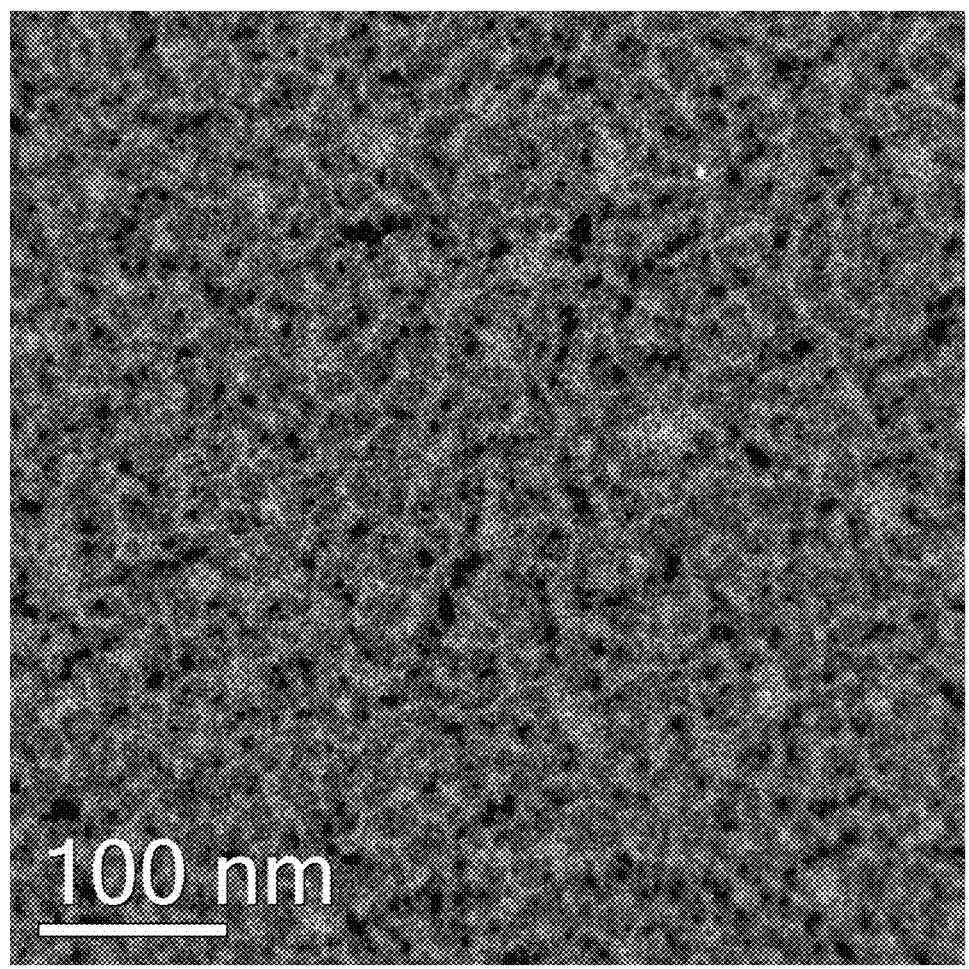

FIG. 31 shows an illustrative SEM image of perforated single-layer graphene on a track-etched polycarbonate support structure. Such configurations can be used as a hemodialysis membrane in various embodiments of some embodiments. In general, any porous support structure that is suitably biocompatible with blood can be used as a support for the perforated graphene in the various embodiments of the membranes described herein. FIG. 32A shows a high magnification STEM image of the single-layer graphene and the pores therein. FIGS. 32B-32D are micrographs of single-layer graphene exhibiting different pore dimension ranges (or average pore dimension) and different pore densities. FIG. 32B illustrates CDV graphene-based material perforated with ion beam (Xe, 500V accelerating voltage, (60 nA·s=3.75×1013 ions/cm2), neutralizer used), while suspended with background gas (air at $1\times10^{-4}$ Torr). FIG. 32C illustrates CVD graphene-based material perforated with ion beam (Xe 500V, 60 nA·s fluence (52 nA flux for 1.14 seconds), no neutralizer used) while suspended with background gas (air at $1\times10^{-4}$ Torr). FIG. 32D illustrates CDV graphene-based material perforated with ion beam (high-fluence (2000 nA·s=$1.25\times10^{15}$ ions/cm2), low energy (20V accelerating voltage) Xe ions) while suspended.

Methods for perforating two-dimensional materials, including graphene-based materials and graphene have been described in the art and include among others, irradiation with ions, bombardment with particles, etching processes and focus ion beam drilling. Methods which allowing formation of pores or perforations of a selected size (dimension) are preferred. Pores may have any useful shape and may be substantially round or may be elongated, e.g., slit-shaped. The terms size and dimension of a pore refer to the widest dimension of the pore which depend upon the shape of the pore. The widest dimension of a round pore is the diameter of the round pore. In preferred embodiments, pore dimensions in dialysis membranes and filters range from about 1 nm to about 30 nm, or from about 1 nm to about 20 nm, or from about 1 nm to about 10 nm or from 1 nm to about 7 nm. In more specific embodiments, pores dimensions in the membranes and filters herein range up to 7 nm.

Figure 32E:
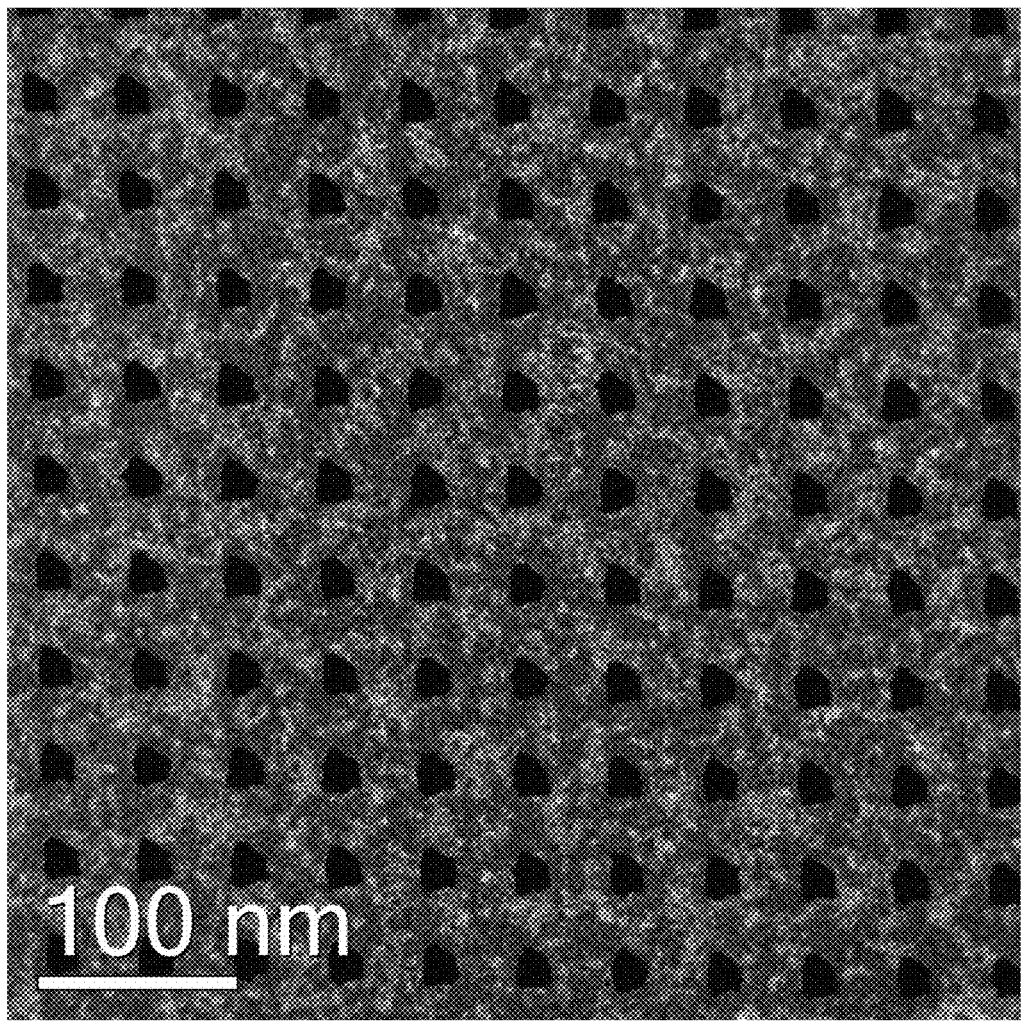

In an embodiment, the membranes herein are useful in filtering applications where high sheer is applied to reduce fouling FIG. 32E illustrates pores formed using focused ion beam drilling where the average pore dimension is 20 nm. Few-layer graphene (up to about 20 graphene layers) can also be used in various embodiments of some embodiments. Exemplary dimensions of the apertures in the graphene can be about 30 nm or less in size, 20 nm or less in size 10 nm or less in size, 7 nm or less in size, 5 nm or less in size, about 2 nm or less in size, or about 1 nm or less in size.

Figure 33:
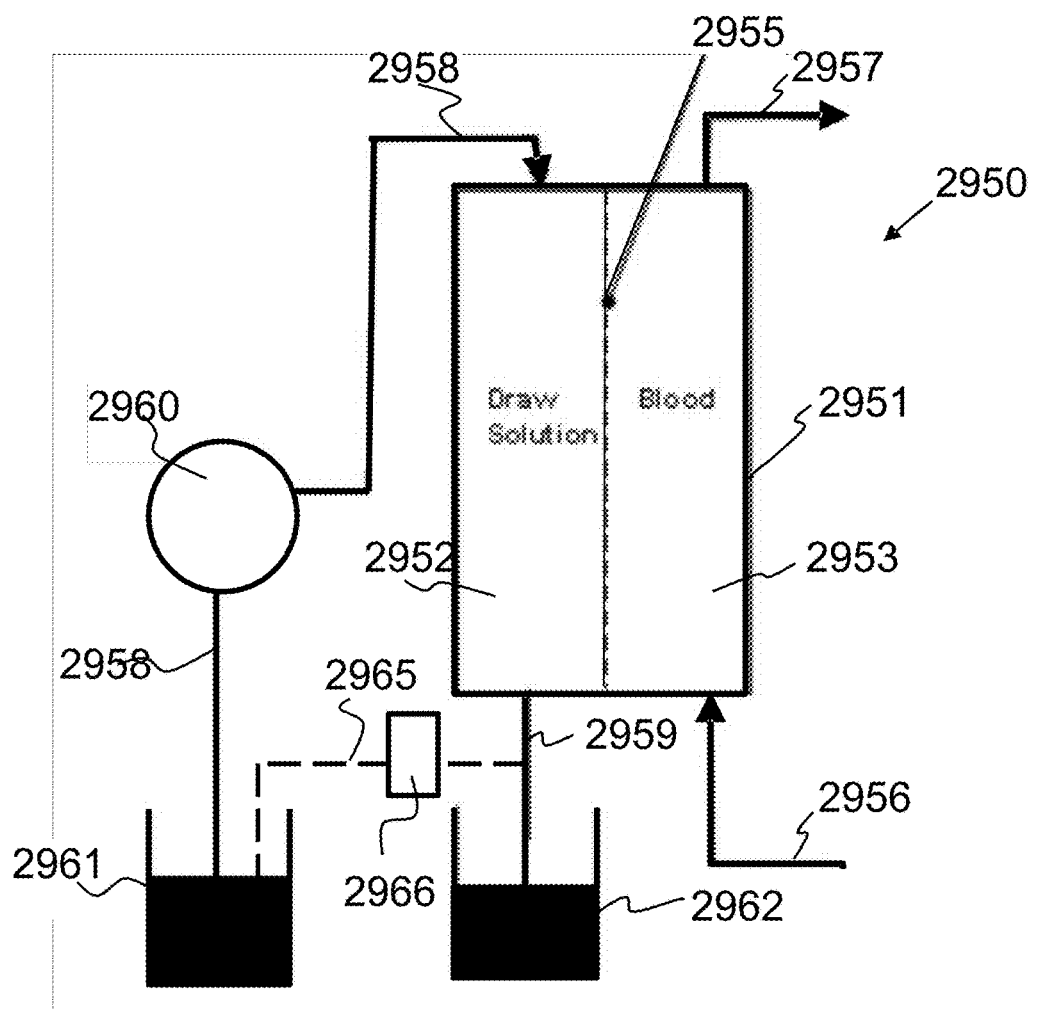
FIG. 33 shows an illustrative hemodialysis system containing a graphene-based membrane (55) and a two-chamber cross-flow vessel (51). This figure also illustrates an optional multiple pass hemodialysis configuration, implemented via optional conduit (65) in which used dialysate is mixed with fresh dialysate to decrease water use.

In accordance with some embodiments, a perforated graphene membrane mounted on a suitable bio-compatible support structure can be configured, for example, in a two chamber cross-flow vessel in a similar manner to today's polymer hemodialysis membranes. FIG. 33 shows an illustrative hemodialysis system containing a graphene-based membrane within a two-chamber cross-flow vessel. In this exemplary configuration (2950), a two-chamber crossflow vessel (2951) having a first chamber (2952) for flow of draw solution (e.g., dialysate) and a second chamber (2953) for flow of blood is provided with a selectively perforated membrane of graphene-based material (2955). A planar or flat sheet membrane configuration is shown. It will be appreciated that alternative membrane configurations can be employed, such as spiral wound membrane configuration. In the membrane (2955), the perforated graphene material is supported on a biocompatible porous polymer. The membrane is appropriately mounted and sealed within the vessel (2951) employing any conventional method that provides an appropriate leak-proof seal. For example, the membrane can be mounted between two biocompatible mating frames with appropriate biocompatible gaskets. Alternatively, the membrane can be mounted and sealed using a biocompatible adhesive.

Figure 29:
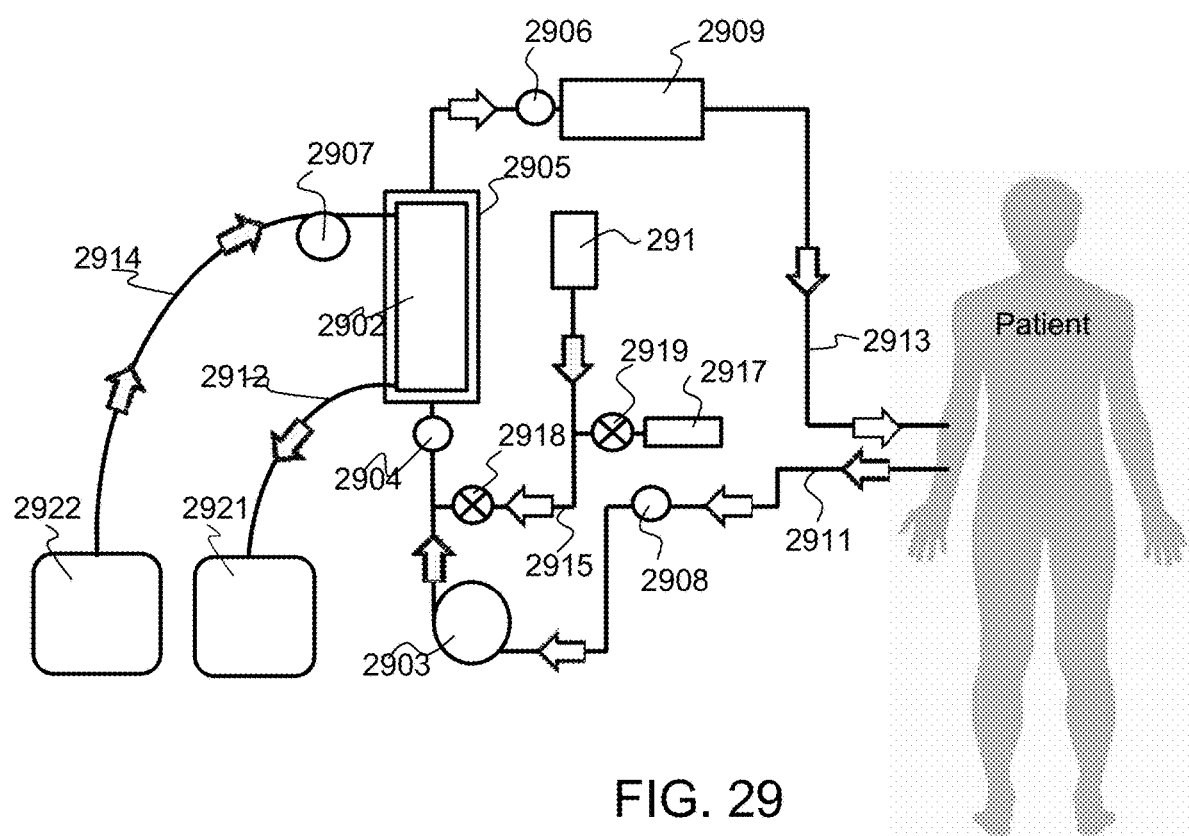
FIG. 29 shows an illustrative schematic of a conventional hemodialysis system and technique.
Figure 30:
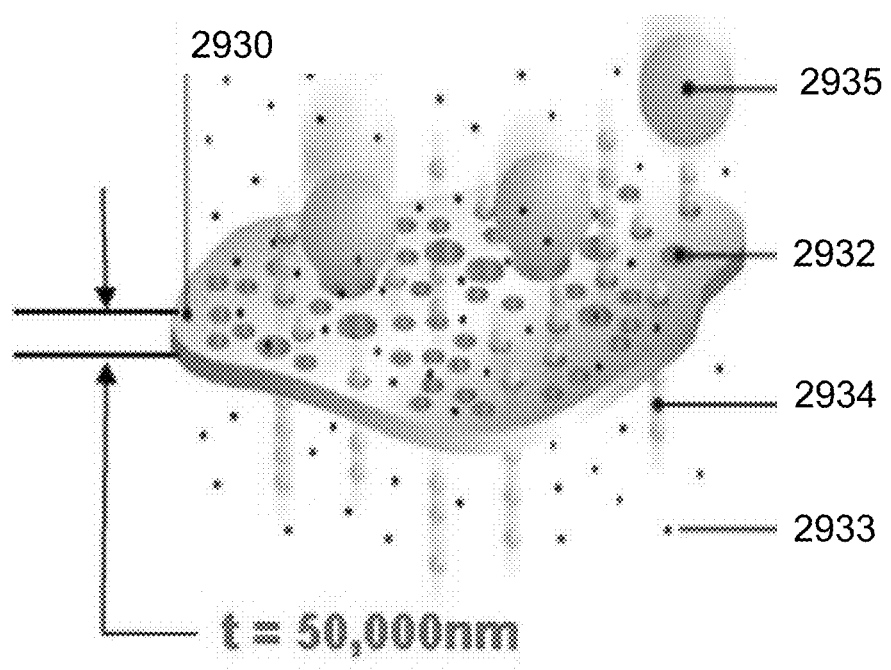
FIG. 30 shows an expanded schematic of a conventional hemodialysis membrane. In this schematic a dialysis membrane is illustrated to have pores of selected dimension (diameter of for example about 2.4 nm) which allows passage of ions, such as Na+; small molecules, such as urea, but does not allow passage of globular macromolecules, such as serum albumin. Conventional hemodialysis membranes have thickness (t) in the range of 50 micron.

In general, contaminated blood entering via conduit 2956 moves across a first surface of the graphene membrane (2955), controlled transport channels in its surface (nominally 1 atom thick and defined by the pore sizes of the perforations) allow a high flow rate of contaminants to be removed very efficiently from the blood and transported across the membrane into the other side of the chamber (2952) where a suitable draw solution (such as a dialysate) entering via conduit 2958, solubilizes or entrains the contaminants and carries them away for disposal via conduit 2959. Cleaned blood exits the system via conduit 2957 and as shown in FIG. 29 can be returned to the patient via an intervening air trap. Multi-layer perforated graphene material as well as other two-dimensional materials can be used in a similar manner. Dialysate is passed through the system employing a pump (2960). A blood pump (not shown) can be used (as illustrated in FIG. 29) for passage of blood through chamber 2953. Flow pressure in the system can be monitored as illustrated in FIG. 29. A fresh dialysate receptacle (2961) and a waste dialysate receptacle can be provided (2962).

In a related multi-pass configuration, used dialysate exiting via conduit 2959 can in whole or in part be transferred via conduit 2965 to be mixed with fresh dialysate for recirculation through the system. Recirculation of dialysate decreases the volume of dialysate needed. In an embodiment in a multi-pass configuration, the used dialysate, such as that exiting via conduit 2959 can be filtered using a membrane as described herein having selected pore size to remove/reduce the levels of undesired contaminant in the used dialysate.

It is known in the art of hemodialysis that it can be important to employ dialysate with minimum undesired components. Thus filtering devices employing membranes of some embodiments which comprises selectively perforated two-dimensional materials, such as graphene, can also be employed in the preparation of dialysate or be employed to pre-filter dialysate prior to introduction into a dialyzer.

Alternate fluidic arrangements that optimize the transformational transport across the graphene membrane can also be used. Another embodiment with a sequence of concatenated filter chambers can alleviate the need for a diffusively active draw solution.

Regardless of the utilized membrane configuration, as a direct result of the increased transport efficiency, the patient treatment time can be greatly reduced, the level of currently infused anti-coagulants (such as heparin) can be greatly reduced because of the graphene surface neutrality and smoothness (minimizing stirring and agitation that can trigger the clotting sequence), and the rate of auxiliary metabolite removal can be carefully controlled so as to minimize depletion of beneficial electrolytes with simultaneous removal of undesired contaminants. Use of the membranes of some embodiments has the potential to decrease complement activation which can lead to allergic reactions during treatment and may also lead to acute intradialytic pulmonary hypertension, chronic low-grade systemic inflammation and leukocyte dysfunction.

In some embodiments, the graphene or other two-dimensional material can be functionalized. Particularly, the perimeter of the apertures within the graphene can be functionalized. Suitable techniques for functionalizing graphene will be familiar to one having ordinary skill in the art. Moreover, given the benefit of the present embodiments and an understanding consistent with one having ordinary skill in the art, a skilled artisan will be able to choose a suitable functionality for producing a desired interaction with an entity in a fluid, such as a biological fluid. For example, the apertures in a graphene can be functionalized such that they interact preferentially with a protein or class of proteins in deference to other biological entities of similar size, thereby allowing separations based upon chemical characteristics to take place. In some embodiments, pores of a given two-dimensional material are functionalized with a chemical species that is positively charge at physiologic pH (e. g., carries one or more amine groups). In some embodiments, pores of a given two-dimensional material are functionalized with a chemical species that is positively negatively charged at physiologic pH (e. g., carries one or more carboxyl or sulfonate groups). In some embodiments, pores of a given two-dimensional material are functionalized with a chemical species that is hydrophobic and in other embodiments pores of a given two-dimensional material are functionalized with a chemical species that is hydrophilic.

In some embodiments, the graphene or other two-dimensional material can be functionalized with a chemical entity so that the functionalization interacts preferentially with a particular type of biological entity (e.g., by a chemical interaction). In some or other embodiments, the graphene or other two-dimensional material can be functionalized such that it interacts electrically with a biological entity (e.g., by a preferential electrostatic interaction). Selective interactions based upon biological recognition are also possible.

Membranes herein include a perforated two-dimensional material supported on a porous substrate. The porous material is preferably biocompatible and in some embodiments is preferably suitable for implantation in a human or animal body. The porous substrate can be a polymer, ceramic or metal. Suitable materials include among others, poly(methyl methacrylate) (PMMA), polyesters, polyamides, polyimides, polyethylene, polypropylene, polytetrafluoroethylene (PTFE), polyvinylidene fluoride (PVDF), polycarbonate, polyetherether-ketone polymers, i.e., PEEK™ polymers (Trademark Victrex, USA, Inc.) and particularly polyaryletheretherketone, polyvinyl chloride (PVC), and mixtures, copolymers and block copolymers thereof. Additionally, non-polymeric substrates such as Si, SiN, anodized alumina, porous ceramics, or sintered metals can be employed. In specific embodiments, the substrate is a biocompatible polymer. In an embodiment, suitable polymers for forming a porous or permeable fibrous layer are biocompatible, bio-inert and/or medical grade materials. In specific embodiments, the substrate is a track-etched polymer. In specific embodiments, the substrate is track-etched polycarbonate.

In an embodiment, the support can itself have a porous structure wherein the pores are larger than those of the two-dimensional material. In an embodiment, the support structure is entirely porous. In embodiments, the support structure is at least in part non-porous.

In embodiments herein the two-dimensional material is a graphene-based material. In embodiments of herein, the two-dimensional material is graphene.

In embodiments herein at least a portion of the holes in the two-dimensional materials of the membranes are functionalized.

In embodiments herein at least a portion of the two-dimensional material is conductive and a voltage can be applied to at least a portion of the conductive two-dimensional material. The voltage can be an AC or DC voltage. The voltage can be applied from a source external to the membrane. In an embodiment, a membrane herein further comprises connectors and leads for application of a voltage from an external source to the two-dimensional material. Application of an electrical charge to a conductive membrane herein can additionally facilitate selective or targeted removal of components from blood, dialysate, and/or water. Additionally, the conductive properties of graphene-based or other two-dimensional membranes can allow for electrification to take place from an external source. In exemplary embodiments, an AC or DC voltage can be applied to conductive two-dimensional materials of the enclosure. The conductivity properties of graphene-based materials and graphene can provide additional gating to charged molecules. Electrification can occur permanently or only for a portion of the time to affect gating. Directional gating of charged molecules can be directed not only through the pores (or restrict travel through pores), but also to the surface of the graphene to adsorb or bind Membranes herein can also be employed in blood filtration applications. In such applications, blood is passed through one or more or preferably two or more membranes in sequence to selectively remove components from the blood by size. For a membrane of given pore dimension, components of sufficiently smaller dimension compared to the pores will pass through the pores of the membrane while components of sufficiently larger dimension compared to the pores will not. Thus, filtration of selected blood components can be accomplished by passage of the blood through one or more membranes with selected pore dimensions.

Figure 34:
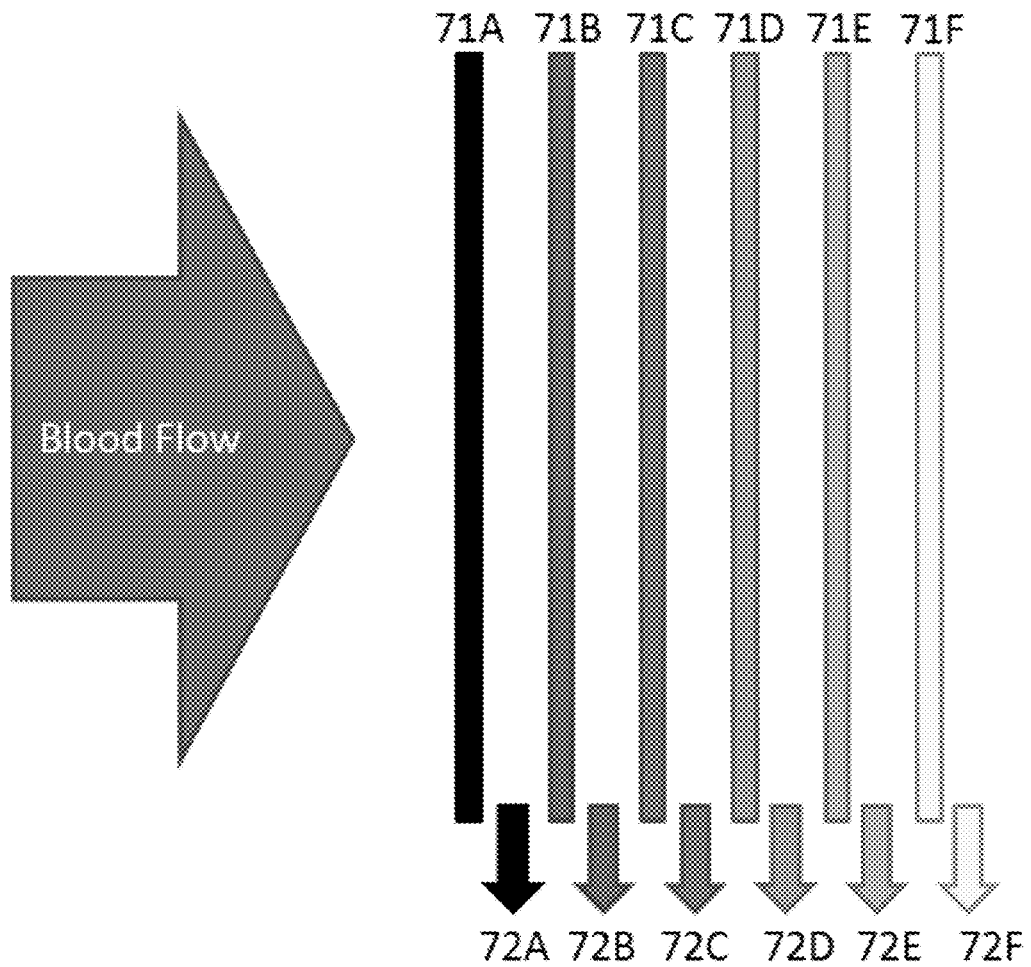
FIG. 34 shows an illustrative blood filtration configuration comprising two or more (6 are shown) graphene-based membranes (71A-71F) each of which have different pore dimensions, for example, where average pore dimension increases from 71A to 71F. Passage of blood through the filter configuration generates two or more flow streams (6 are shown, 72A-72F) containing size separated components dependent upon the pore dimensions of the filters. For example, where average pore dimension increases from 71A to 71F, the flow streams from 72A-72F will contain components of decreasing size.

An exemplary filtration configuration is illustrated in FIG. 34. In this configuration, blood is passed sequentially through a plurality of membranes at least two of which have different pore dimensions or pore densities. Preferably, at least two of the plurality of membranes have different pore dimensions. In the illustrated embodiment, six membranes are provided (71A-71F). Preferably, each of the membranes in the filtration configuration has different pore dimension.

In a specific embodiment, the pore size dimension of the membranes decreases in the direction of blood flow. Passage of blood sequentially through the membranes generates flows (72A-72F are shown) which contain blood components separated by size. The separated flows can be individually collected, individually discarded or two or more of the flows can be combined for any appropriate use.

As discussed above, hemodialysis and hemofiltration are employed to remove toxic substances such as creatinine and urea from the blood typically to replace or supplement such function of the kidneys. The term "removed" is used herein to encompass a decrease in level of the component after dialysis or filtration. It is noted that the term removed includes decreasing the level of toxic species in the blood to non-toxic levels or to with the range of concentrations found in those whose individuals who have normal kidney function. During hemodialysis and hemofiltration, it is undesirable, as is known in the art, to remove or significantly lower the concentration of certain components below their normal concentration range in individuals with normal kidney function. One such component is serum albumin the removal of too much of which can be detrimental to an individual. It is generally known in the art which blood components should be removed and which should be retained to in general achieve component levels that are within the normal concentration level of the components in the blood. In some cases, hemodialysis and hemofiltration are performed continuously in an attempt to maintain levels of toxic species in the blood at concentrations the same as those in individuals with normal kidney function. In many cases however, hemodialysis and hemofiltration are performed intermittently (e.g., on a set schedule) to lower levels of toxic species in the blood to normal or below normal levels. During the time between treatments, the levels of toxic species can build up in the blood.

The membranes of some embodiments formed by introduction of pores of selective dimension into sheets or layers of two-dimensional material are particularly suited to targeted removal of components based on size. As illustrated in FIGS. 32A-32E, methods are available in the art for introduction of pores of different dimensions which allow for such targeted removal. For example, two-dimensional material having average pore dimension or size of 20 nm will allow passage of water, ions and most small molecules (molecular weight of 500 or less) and will also allow passage of many proteins. Two-dimensional materials having average pore size of 7 nm will allow a passage of water, ions and most small molecules (molecular weight of 500 or less), but will not allow passage of many protein species, such as serum albumin. Two-dimensional materials having average pore size of about 1 nm will allow passage of water and atomic ions generally, but will not allow passage of many molecular components. Choice of pore dimensions in a given membrane allows targeted removal of components from a liquid, such a blood.

Although some embodiments provided herein are primarily directed to hemodialysis membranes and blood filtration membranes formed from graphene materials it is to be recognized that graphene oxide (GO) and reduced graphene oxide (rGO) can also be used in alternative embodiments. It will be appreciated that filtration devices containing membranes and membranes herein may be prepared from combinations of two-dimensional materials. Other perforated two-dimensional materials can also be used as well. In addition to in vivo hemodialysis and hemofiltration techniques, ex vivo dialysis and filtration techniques are also contemplated as well.

Methods for treating a patient using the disclosed membranes are also contemplated herein. These treatment methods are performed using the disclosed membranes in a manner similar to that used with conventional hemodialysis or hemofiltration techniques. In brief, the methods involve contacting blood from a patient with a graphene-based hemodialysis or hemofiltration membrane (or membrane configuration, as illustrated in FIG. 34) in order to remove one or more contaminants therefrom. Contaminants removed from the blood by hemodialysis can then be removed in a dialysis fluid or those removed by filtration in a separated flow can be removed or collected as desired. The purified blood can then be recirculated to the patient. In an embodiment, hemodialysis methods herein are combined with blood filtration methods herein. In an embodiment, conventional hemodialysis methods herein are combined with blood filtration methods herein. Hemodialysis membranes and blood filtration membranes herein can also be employed in implantable devices, such as art-contemplated artificial kidneys and bio-artificial kidneys.

The membranes herein can further be employed for peritoneal dialysis and in renal assist devices. Peritoneal dialysis is also employed to remove waste products from blood when normal kidney function is lost or impaired. Blood vessels in the abdominal lining (the peritoneum) replace the function of the kidneys when a dialysate is flowed into and out of the peritoneal space. Membranes herein can be employed for filtration of dialysate in peritoneal dialysis. Renal assist devices include wearable and implantable devices for hemodialysis and peritoneal dialysis. Membranes herein can be employed to implement such devices as dialysis membranes and/or filtration devices. Certain renal assist devices (e.g., bio-artificial kidneys) include biological cells for carrying out certain metabolic functions. For example, an implantable artificial kidney can include a bio-cartridge of renal tubule cells which, mimic the metabolic and water-balance function of the kidneys. Two-dimensional materials, particularly graphene-based materials can be employed as selectively permeable enclosures to retain such cells and to allow selective entry of components into the enclosure and selective exit of components from the enclosure. Such enclosures can for example be employed in artificial kidney which contain a bio-cartridge. Such enclosure are described for example in U.S. application Ser. No. 14/656,190.

Ex vivo dialysis techniques can be conducted similarly. Such dialysis techniques can be conducted upon a biological fluid, such as blood, or upon other dialyzable fluids in need of contaminant removal therefrom.

Although some embodiments have been described with reference to the disclosed embodiments, those skilled in the art will readily appreciate that these only illustrative of some embodiments. It should be understood that various modifications can be made without departing from the spirit of the disclosure. Some embodiments can be modified to incorporate any number of variations, alterations, substitutions or equivalent arrangements not heretofore described, but which are commensurate with the spirit and scope of the embodiments. Additionally, while various embodiments of the disclosure have been described, it is to be understood that aspects of the disclosure may include only some of the described embodiments. Accordingly, the disclosure is not to be seen as limited by the foregoing description.

Every formulation or combination of components described or exemplified can be used to practice the embodiments, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials and synthetic methods other than those specifically exemplified can be employed in the practice of the embodiments without resort to undue experimentation. All art-known functional equivalents, of any such methods, device elements, starting materials and synthetic methods are intended to be included in this disclosure. Whenever a range is given in the specification, for example, a temperature range, a time range, or a composition range, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The embodiments illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

In general the terms and phrases used herein have their art-recognized meaning, which can be found by reference to standard texts, journal references and contexts known to those skilled in the art. The preceding definitions are provided to clarify their specific use in the context of the disclosure.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the disclosure pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

What is claimed is:

1. A process for forming a blood filtration device, comprising:

exposing a multilayered material to ions provided by an ion source, the multilayered material comprising a first layer comprising a two-dimensional first material and a second layer of a second material in contact with the first layer, wherein the ions have an ion energy ranging from 1.0 keV to 10 keV, and a flux from 0.1 nA/mm$^2$ to 100 nA/mm$^2$; and producing a perforated two-dimensional material by producing a plurality of through-holes in the two-dimensional first material by interacting the ions with the two-dimensional first material and with the second material;

forming at least two of a composite membrane comprising a porous substrate having a plurality of pores and a sheet of the perforated two-dimensional material disposed on a surface of the porous substrate and defining a top surface of the composite membrane, wherein the sheet of the perforated two-dimensional material covers at least a portion of the plurality of pores of the porous substrate and wherein at least one pore of the substrate is not covered by the sheet of the perforated two-dimensional material;

introducing one or more occluding moieties at least partially into the at least one uncovered pore to occlude the at least one uncovered pore;

incorporating at least two of the composite membranes to form the blood filtration device;

forming a cross-linked graphene platelet polymer membrane by reacting an epoxide-functionalized graphene platelet with a (meth)acrylate- or (meth)acrylamide-functionalized cross-linker; and incorporating the cross-linked graphene platelet polymer membrane, having a plurality of cross-linked graphene platelets, into the blood filtration device, wherein the plurality of cross-linked graphene platelets have a graphene portion and a cross-linking portion, the cross-linking portion containing a 4- to 10-atom link.

2. The method of claim 1, wherein the perforated two-dimensional material is graphene-based material.

3. The method of claim 2, wherein the graphene-based material is single-layer graphene.

4. The method of claim 2, wherein the perforated two-dimensional material is graphene oxide.

5. The method of claim 1, wherein the one or more occluding moieties are particles sized for at least partial introduction into the at least one uncovered pore, but which cannot exit the at least one uncovered pore.

6. The method of claim 5, wherein the particles are deformable or swellable.

7. The method of claim 5, further comprising:
applying pressure or energy to the particles after the particles are at least partially introduced into the at least uncovered pore,
wherein the particles are deformable.

8. The method of claim 7, wherein heat or light of a selected wavelength is applied to the particles.

9. The method of claim 7, wherein an electron or ion beam is applied to the particles.

10. The method of claim 1, wherein the at least two composite membranes are a hemodialysis membrane.

11. A method of removing contaminants from blood of a patient, comprising:
exposing the blood to the hemodialysis membrane of the blood filtration device formed by the method of claim 10;
removing at least one contaminant from the blood with the hemodialysis membrane; and
recirculating purified blood to the patient.

12. The method of claim 1, wherein the sheet of the perforated two-dimensional material is primed, activated, or functionalized to bind or react with the occluding moieties.

13. The method of claim 1, wherein the one or more occluding moieties are selected from the group consisting of oligomers, uncured polymers, uncross-linked polymers, hydrogels, proteins, zeolites, metal-organic framework materials, or thin film solution membranes.

14. The method of claim 1, wherein the one or more occluding moieties are selected from the group consisting of polyhedral oligomeric silsesquioxanes, fullerenes, dendrites, dextran, micelles or other lipid aggregates, micro-gel particles, silica particles covered with polyethylene glycol, and hydroxycellulose.

15. The method of claim 1, wherein the one or more occluding moieties are fluorescently tagged.

* * * * *